(12) United States Patent
Moore et al.

(10) Patent No.: US 8,003,318 B2
(45) Date of Patent: Aug. 23, 2011

(54) POLYMORPHISMS IN GROWTH HORMONE RECEPTOR, GHRELIN, LEPTIN, NEUROPEPTIDE Y, AND UNCOUPLING PROTEIN 2 GENES AND THEIR ASSOCIATIONS WITH MEASURES OF PERFORMANCE AND CARCASS MERIT IN BEEF CATTLE

(75) Inventors: Stephen Moore, Edmonton (CA); Donald Joshua Nkrumah, Edmonton (CA); Esther Laura Sherman, Edmonton (CA)

(73) Assignee: The Governors of the University of Alberta (CA)

( * ) Notice: Subject to any disclaimer, the term of this patent is extended or adjusted under 35 U.S.C. 154(b) by 998 days.

(21) Appl. No.: 11/653,790

(22) Filed: Jan. 16, 2007

(65) Prior Publication Data

US 2007/0212713 A1    Sep. 13, 2007

Related U.S. Application Data

(60) Provisional application No. 60/758,616, filed on Jan. 13, 2006, provisional application No. 60/836,777, filed on Aug. 10, 2006.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| | | | | |
|---|---|---|---|---|
| 6,287,254 | B1 * | 9/2001 | Dodds | 600/300 |
| 7,157,231 | B2 * | 1/2007 | Mitsuhashi et al. | 435/6 |
| 2004/0254104 | A1 * | 12/2004 | Blott et al. | 514/12 |
| 2005/0065736 | A1 * | 3/2005 | Bauck et al. | 702/20 |

FOREIGN PATENT DOCUMENTS

WO    WO 2005/112544 A2    12/2005

OTHER PUBLICATIONS

GenBank Accession No. AY643807 GI 49354915 Jul. 3, 2004.*
Adkins, Ronald et al. Molecular evolution of growth hormone and receptor in the guinea pig a mammal unresponsive to growth hormone. 2000 Gene vol. 246 pp. 357-363.*
Sorensen, P et al. Polymorphism in the bovine growth hormone gene affects endocrine release in dairy cows. 2002 Americn Dairy Science Assoication. vol. 85 pp. 1887-1893.*
Buchanan et al., Association of a missense mutation in the bovine leptin gene with carcass fat content and leptin mRNA levels. Genet Sel Evol. Jan.-Feb. 2002:34(1):105-16.
Lagonigro et al., A new mutation in the coding region of the bovine leptin gene associated with feed intake. Anim Genet. Oct. 2003:34(5):371-4.
Liefers et al., Associations between leptin gene polymorphisms and production, live weight, energy balance, feed intake, and fertility in Holstein heifers. J Dairy Sci. Jun. 2002:85(6):1633-8.
Liefers et al., Association of leptin gene polymorphisms with serum leptin concentration in dairy cows. Mamm Genome. Sep. 2003; 14(9):657-63.
Nkrumah et al., Polymorphisms in the bovine leptin promoter associated with serum leptin concentration, growth, feed intake, feeding behavior, and measures of carcass merit. J Anim Sci. Jan. 2005:83(1):20-8.
Schenkel et al., Association of single nucleotide polymorphisms in the leptin gene with carcass and meat quality traits of beef cattle. J Anim Sci. Sep. 2005;83(9):2009-20.
Maj, A. et al. Polymorphism in the 5'-noncoding region of the bovine growth.hormone receptor gene and its association with meat production traits in cattle. Animal Research. Nov. 2004, vo!. 53 pp. 503-514.
GenBank Accession AY643807. Bos taurus growth hormone receptor gene, exon 4 and partial cds. Jul. 2004.
Sherman et al. Polymorphisms in the GHR, NPY, Ghrelin, and UCP2 Genes and their Associations With Measures ofPerfonnance and Carcass Merit in Beef Cattle. Plant and Animal Genomes XIV Conference Jan. 14, 2006 (Poster).
Nkrumah et al. Polymorphisms in the leptiu gene and their associations with perfornnance, feed efficiency, and carcass merit ofbeef cattle. Proceedings of the 8th World Congress on Genetics Applied to Livestock Production [online], Aug. 2006 [retrieved on Jan. 5, 2008].
Maj A. et al. Molecular evolution of coding and non-coding sequences of the growth Hormone Receptor (GHR) gene in the family Bovidae. Folia biologica. Jun. 2006, vol. 54 pp. 31-36.

* cited by examiner

*Primary Examiner* — Amanda Shaw
(74) *Attorney, Agent, or Firm* — Judy Jarecki-Black; Chad Kitchen; Merial Limited

(57) ABSTRACT

The physiological regulation of intake, growth and energy partitioning in animals is under the control of multiple genes, which may be important candidates for unraveling the genetic variation in economically relevant traits in beef production. The present invention relates to the identification of a single nucleotide polymorphisms (SNPs) within the bovine genes encoding growth hormone receptor (GHR), ghrelin, leptin, neuropeptide Y (NPY), and Uncoupling Protein 2 (UCP2) and their association with economically relevant traits in beef production. The invention further encompasses methods and systems, including network-based processes, to manage the SNP data and other data relating to specific animals and herds of animals, veterinary care, diagnostic and quality control data and management of livestock which, based on genotyping, have predictable meat quality traits, husbandry conditions, animal welfare, food safety information, audit of existing processes and data from field locations.

2 Claims, 13 Drawing Sheets

```
  1 tagaagtggt tgctcttgat cactttaaat gtgtgtctca ttaggaccat ccattaccct
 61 cctgatttca tgacttgtct tgtcttttta ctctgcagat tcttctggga atcctaaatt
121 caccaagtgc cgttcacctg aactggagac tttctcatgt cactggacag atggggctaa
181 tcacagttta cagagcccag gatctgtaca gatgttctat atcagaaggt atgggcttca
241 tgcttttctg atttctctcc atgaattttc tgatgaaaat ccattgagtg tcatgcagta
301 gtgggaatgg aaataatctt ctttggtgat ctaaatgcat tcacccattc attcatttaa
361 atatattagt taagcccctta ctatatgttg gg
```

(SEQ ID NO: 1)

FIG. 1

```
   1 gaattcaaca attctattta tcaagaaatc tcccacaaat atactcacac tgtgctccaa
  61 taagtacttt tgagtctatt aattaacaac attatgtatc taacattatg gttagattga
 121 ttatggtgca tctgtgaaat gaaacatacg ctgactctaa aatgattggc acaatcctgt
 181 gtattggtaa gaaattgtat tctagatata ctaggtgaaa gaagtgagat taataatggt
 241 taaaattggg caatggtaca tggacatttg taatgccatt tttccttata agtgtattgt
 301 ggagatttaa attttccaa aaaaaaaat gtggaggcag ggggcaagaa cattagtgtg
 361 aataatatga cattatttaa atgcccttaa atatatattt tttaattaat ttatttattt
 421 tttctatgct gggtcttcat tgcaatgtgc aagcttctca ctgtggcagc ttctcctgtt
 481 gtggagcata ggctccaggt gcccagggac tcagcggttg caacacacag gctctagagc
 541 ttgggctcgg gagccgtgtc acacggcctt tgttgctccc agcatgtgga atcttcctca
 601 accagggacc gatcccgcgt ccctgcactg gcaggcggat tctcatccac tgtaccacca
 661 aggaaggcct gcacactttt ttttttaagg aaatggatat atgaaggaca gaaaaagaat
 721 atccatggaa ggatacacca taaactgaga agaacaacta cttctaggga aaaaaggact
 781 ggggagagac tgagttttca tatctttgtt cctttttgaat tttaagaaaa ataatacatt
 841 attctaacac aacattgtaa agcaattata cttcaataaa aaattaaaag taaaaatact
 901 ttattatata ataatatata attataatat aatataaaca ttcagttcag ttcagttcac
 961 ttcagtcgct cagtcgtgtc cgactctttt cgaccccatg aatcgcagca caccaggcct
1021 ccctgtccat caccaactcc cggagttcac ccagactcat agtaatatat aataatttat
1081 tttaaaataa ttattaatca acacgaaatg taaaaaatag gtaggtgatg ggtagatagg
1141 cagacgggca gtccacacac tcacatgtgg tctcaagtgc tacttggtgt tcaggcaata
1201 actctggtcc caatctgacc tctgacccctt aaaaggtga tggtaagaca agtaacctga
1261 ggctgccagg gcccctgcct atgagctaag actctgctta gaaccaagtt acaaagatgt
1321 tgcagacaag aaaaatttgg tcgtagtgga tgctactgcc tctatttgaa aaacaacaca
1381 aacatttccg gggggggggg gaggcggaga ggaggaaaga ttttcttcaa aatgtaattt
1441 cattgtagac acttctttaa aagaaacatt tcttttatttg acagttccag gccttagttt
1501 cagcaggcag gatgtttagt cgcagcatga gaactcttag ctgcggcatg cgggacccag
1561 ttcagttccc tgaccagata tcgaacctgg ggccctgca tttggaagca gggagtctta
1621 gccactggac caccagggaa gtccctgta gatgttttta tgaaaagcag aaaagcacaa
1681 agaagagctt aaagattcct gatcctactc ccaatagtga taatgtatat tttggtgtga
1741 gagtgtgtgt attgattgga atgtgtgtga tcagaaaaca cataccattt tataatccgt
1801 tctttccagc tcacaaaata aagttatttt cctacatcat taaatattac tttacaacat
1861 aattttaat gtgtgcatat tgctgctatg tgattttcaa taacttacta atttcctatg
1921 ctgaacattt agttgttgtc caacctttt agtggccatg taattataaa tcatggtcaa
1981 tgctaacaat ttctgacctc acaaacatat agtacaatat ccttcctttc ttcaatagat
2041 aattattaaa agcaaaacaa ccaggctcaa acaaagcaat tataaaatat cttttaaaaag
2101 acattgggta aaattcaaat gcagactagc tcatgatgtt aaagaattac tcttgtgtgg
2161 taatggtctt gtgatagaga tagaaatgct tccttatttt tcagataaac acttaagtat
2221 ttaaggatga aacgccctga tgtttgtaat ttgctttaga atatttagc caaaagaatt
2281 aatgatgcaa atatgcaaaa agagtacgtt aaacctaaat ttgcgatttt catttaaaaa
2341 tatatcttaa aaatgaaaat cttcgtgcaa cgcacgggc tatcaatgtg ggatacagat
2401 gtgaacaaaa cggacccgtg tgggactcgg cggagcacac agattttgcg ggagcacgtt
2461 cccgttagga agtctctgat gcaatacgac cggtgccctt caggacctgt gagactgact
2521 ttccttaccc ctccacacca tcatcaaggc aggtgtgatt ttccaggcca ggcctacggc
2581 cgggtttccc cgggggccca gagccgtcgg gtcttgccgc ccagcggagc tggctgctcc
2641 ggcctcactg tcggggcgcc accgccccca gccggctcag aggaacccct caccgccacc
2701 ctgtcccagg cggccttttcc ccgaggcccg agggtcagat cctgggcccg cctcgaggat
2761 ttctcacacc tgcccagcca ccccagcttt tcaggtgat accggagggt gggcgtgggg
2821 ctcctggcgc atccgagtcc ctccctggag tccccgaccg cggccgcccg gcccgacgct
2881 gccccgccgc cccgcagggc gggagccggc gctgcgggtg cgccccggcc agccgggcag
2941 ttgcgcaagt tgtgcttcgg cggctataag aggggcgggc aggcatggag ccccggaggg
3001 atcgaggaat cgcggcgcca gcagcggcga ggtaagtgcc cggctctctc ct
```

(SEQ ID NO: 2)

FIG. 2

```
  1 gaggcaaagg gcagggtggt ttgggaaggg cagaaagata ggagcccagg agaccagctt
 61 ggaaacatgg tggtcacgtg ggcacaagaa gtaagggccc agggaggatg gtgtggaagc
121 gggggaggaa gcacctctac gctctaggga aaggcggagt caggggagct ctgaggagct
181 gccctctctc ccactgagct cttgctctcc ccttcctcct gcatagcagt ccgtctcctc
241 caaacagagg gtcactggtt tggacttcat ccctgggctc caccctctcc tgagtttgtc
301 caagatggac cagacattgg cgatctacca acagatcctc accagtctgc cttccagaaa
361 tgtggtccaa atatccaatg acctggagaa cctccgggac cttctccacc tgctggccgc
421 ctccaagagc tgcccttgc cgcaggtcag ggccctggag agcttggaga gcttgggcgt
481 tgtcctggaa gcttccctct actccaccga ggtggtggcc ctgagccggc tgcagggtc
541 actacaggac atgttgcggc agctggacct cagtcccggg tgctgaagcc ttgaaggcct
601 ctcttcccaa agtccaggga agaaacctga gcttctggct gtccacagga aagagagcc
661 tatgtgggca tcctttatgc aggccagcgg gccatttctc tctcgctcct ctcagctgct
721 cttccaaagg cagaaaactg cgaggcagga aaccaaagat ataaatacag attccacgcc
781 caccgg
```

(SEQ ID NO: 3)

FIG. 3

GTCCAGGGCCCCAGCTTTTAGGGGACGGGCCGAAGTGGCACAGTCCAACTCTGGGCCGCTCC
TCTCGCCGTTACAGCACATCTCCTCCGCCCCTGTGGAAGGGAAGCCAAACCGGAGGGCAA
CGGGAGGAGAGCAGACACAGTTGAGGTTTTTTTGGTGGTTTTTCTTTTTTTGGCTACACTGT
A
AAGCGTGGGGATCTTAAGTTCCCCA [A/G] CCAGGGATCAAACCCGTGCCCCTGTAGTGGAA
GC
ATGGAGTCTTAACCAGTGGACCGCCAGGGAAGTCCCGGACACAGCTCTTTGACTTGACCTCT
T
GCGTTTCAGAAACCCTGGCTAACGAGTGAGTGGCC (SEQ ID NO: 4)

FIG. 4

```
   1 atgctgggta gcaagcgact ggggttgtcc ggactgaccc tcgccctgtc cctgctcgtg
  61 tgcctgggcg ccctggccga ggcgtacccc tccaagcctg caaccccgg cgaggacgct
 121 ccggcggagg acttggccag atactactca gcgctgcgac actacatcaa tctcatcacc
 181 aggcagaggt aggtgggctg cgcgggactc acgactccgg gagcgcccca cttgcacacc
 241 cggagatcat gggcatcttg aaggacaagg tcttttttctt tttmtttttt gtatcccagg
 301 gccagacaac atcaggcaca tactcagctc tcagtaaatg tttgcacagg gagcaactac
 361 ctcggccact actgtcacaa atcctgatc cccagactca ggtcctccag tctggggggtc
 421 tgactggcca tttcctctca cccatccctt tgtcttttt gttcttagag cagtcggggg
 481 actgtttgga aacctggata ggaaagtacc cagtgaaagg ggtcaggagg gcgctgggag
 541 gtggctatta gctgagaggg ctgcagggta tctagaaaaa taacagcaca agctagggag
 601 gaaacagctg ggtcaccaaa gacattgcca gatttttcag cctgcccaga ctgaagtgaa
 661 aagcatcta gaactatttc ccccgtacag tgttttattt cggtctgaac cccttacctg
 721 aaaatcctgc tcctaataag tagagattta gcatgaaaac attagtctaa aatgctgaga
 781 cttttcccat ttcatagcag gtgagttcgg aaaagaaaat gcccacttgg tgcttttttta
 841 aggagaaact acaatgatc tgttcacttt aggatgaatc cagggattac atgtactttg
 901 agaaattgtc atctttattc tgaaccccta gaaagctaaa atgaaaggcc acatttcatt
 961 ctcaacatca aatcttaagc aagaaatcaa atccaaacta ttttagaagt aacataggat
1021 ttaaaatttg tttccaaaat taattcatct tagttttgaa tcattcaatt tttaaaatta
1081 ctgagatcaa atgtccttaa taagctgaaa acaatgagct ttattactga gatcaaatgc
1141 ccttaacaag ctgaaaacaa tgagcttttt acaaagttta atgttattta acatatttat
1201 gttttaaag tattgttttt tctttgctgt tttactatat ttcaaggaat agttggaaag
1261 aatttaaagt ggggaaaaat ttgtattaaa gaaaactcta actttgatga aactttctgt
1321 ttcatcaaaa agcttttaaa gaaccaattt atatgaaatt agaaatatat gaaaatgcta
1381 gaattaaata gcattggttt atgatccctg aagtctgata cttttcatta gtgaaaagca
1441 agaatgtctt atatcttaat agaccttcag aaagttaatt gcttcatatt cttcttatg
1501 catcataaag accagagaaa aaactgtaca aattgttttt ttttcccct aggaaagact
1561 ttgttagtta tttagcctgt taattatagc atataatggg aacttagttt tacaaagatg
1621 attgatataa acctttacta ttgggtaaag ctttggcatt tcaaaatgtt ttccagtcta
1681 ttaccttgtc cagcttttga aggggagtat aaattatccc cccagttttc cagatccatg
1741 aaattaagga catttcatgg aaaccttttt taggggggtga ttaaattgga gccctcctct
1801 tgatctctgg atgttgtcac tactatcagc acttagagtg atcttcaata cctttgagga
1861 ggagaaaata agggaaaggg ctaatattca ggttagcaag tgttcctgaa gcagtttcct
1921 atctcctttt catataagtt ccttcttaga aacactcaga ggctcataat ctgcacccat
1981 cacctccatt ctatactctc atcatcttcc caccacacac atccactcat ctgcacattt
2041 gtattttga aaattacgtt tatacacata catttttaatt tggtatagat ggtactgtga
2101 tattctcttt cctcccttt tctacttggt tcatgttcta aagctatata ctcctcgttc
2161 attgcttcca aaggtggcat catttattct agagcataga tctaccgcat tttatttta
2221 cagtcatcta tatcagtggt tctcaactgg ggttgacttt atgctcccca agacattggg
2281 caatatctgg agacgttttc agttgtcata atggtgggat ggggtggggt ggggtggggt
2341 ggcatggggg ctactactgg catctagtga gtagaggcca ggacgctgc tgaacatctg
2401 cggtccctag gacagccctt gacaataaag aattatccag ctcaaaatgt gcacagtgcc
2461 aagactgaga aactcagccc tggactagag ttttcttcctc ctagtctcat tgttatcatc
2521 tggggaactt ttagaatata ctgatgctga gccgcacccc tgaggagtta atcagaatc
2581 tcccagaagg tgggacatgg gcttttaaaa acccccaggg gtgattctaa catctagcca
2641 ggtttgattt tcctagagat gctatctttg aagataaag cattgtcaag aagaaggata
2701 atccagaatt aattcgagat gggagaacag tcattgatgc tgctctggt acctactact
2761 ttctgactac aaattctgct attgcagact taagttctct aatggtaaat tggagaaaat
2821 attccagt tctttaattc actgcagcat gatgaaaata aacgagttaa ggttgcccaa
2881 gagttttagg attagtaaaa tcaactgatg gacagaataa atacatataa attgctgcct
2941 acagtctgat atcacaacac cagaaaatct tgaggaaat ctcgcaaatg atggggcga
3001 gagagttggc tttgcttttg tattccttga gyccctgcaa aggagcaata ataggaacgt
3061 tttcctccaa atttagattt aattgtgctt gataggcagc tagcatatac tctctatcag
```

FIG. 5A

```
3121 ctttattcca cctgttttat ctgatatcta atcaatccac cagtagacta ttttttatt
3181 tgtgaaaaaa agcagctact gatgtccaat gctcttttg agaaagggaa aaatagtgtc
3241 ttcaaaaaaa tacaacttgg tgtagatttc tcagctcctt tggcagagag agagagacag
3301 acaaacagac catgtcctca ctcacctggg gccagcagca tatactaccc tggcaggaaa
3361 acataacctt gaatccatat attgttctac ccatacctg ctatgggaga aaagagacta
3421 cccataccct gctatgggag aaagagacc aagaacattt ctatggacca gtaggtttcc
3481 ttcatatttt cagggcagtt taaaatcatg ttaggagaga agactttag cttttggcac
3541 cccaaataaa catggaaaat ataggactca gaatctgttg gtagctgtga gaatggatgc
3601 atttcagcag cagtaatgtg cattttgta tatcactctg ttgctttcag agcattgtga
3661 cttacagtgg atattcatca agattctaat ttaagcagga gttatgattt tgttgatgtt
3721 ttatatttaa taccacaaat cttctttc taaaggtgtt tatggtttct ccaaacttgc
3781 cttaaaggac ttttactccc ccaacccatt tttttcttcc agatacggga aacgatctag
3841 ccccgagacc ctgatttcag acctcttgat gagagaaagc acgggaaaca ttcccagaac
3901 taggtatgaa aagacttagt gggaacactg ttgcagagct caaggtggtc agggaagga
3961 aatcagagag gactgctgga agaaggtgtt gggatgggt cctccagacc aggtaagatt
4021 tggacagaaa gagtgatggg gaacagagca tggaggacct ttctcttcac atactcattt
4081 acaaatctct gaacttgtgg gataatattt tctgattcaa cttaatttga tgctcctttg
4141 aaattttcaa atataaatga tttttgcctc aaaaattact ctatagaaaa tttctgattg
4201 acttagattg gggaagcata gggtatgccc taatatctac attgaaataa ccaactgtct
4261 gtctttggct gaggtaatct ttagttctta tagtctacgc agaggattta cacatccttg
4321 gaaatgttcc ctcctggctt cactccagtc acactggttt tacaagaagc tgtagataaa
4381 tcaaggggtg ctcctgttta cttttgact tatttagtt catctgatgt cacattgtaa
4441 tttatcacat tcagtgaatg agcattgaac aacatgttat cttagggct tgcttggaaa
4501 cttggggctt tcttggagtg tggagctgcc tcaggacagg tgccctctaa tatctaggtg
4561 tcaaacattg ggctggggtc attctaggta aagactgaaa gtgaaaagac gcctgctcct
4621 cctccttttc catagctggc tctcctgtcc caggcccact gtcccttccc ccagtaagat
4681 ggcctgtcta ccttaaaccc agagctctac aacatcaaga accaagctcc ccagaagagg
4741 tcactagaac acttgctcag tgcatgtgac tggcttgtca ctcttcattg ggttctccct
4801 ctgttctctt gtgcaatggc caggcagtgg gaaggtgcaa gtctagagtt gtcaggtttg
4861 ttttctctga aggacacaca atttggattg gaataaaact cagtgctctt gtccctggtg
4921 gcactagcag acttgaacag caaatgcaag ggaagcaggt ggaaaactca taaaggtggt
4981 tttaaaatac taagcaatac atgctttaat gtttcattaa taggcatatg atgtttgtca
5041 cagtaataag tttaggatat gctatatcta ctcaagatta gaaatatgat catccagacc
5101 aacctacagc cttaacgctg ttctttgttt tgtggcccaa agtcacatgg ctggtgaatg
5161 aaatagagtt aattgtactc tgattgacag cttaatcat gtgcacttag aaggagacaa
5221 aacctgacag ccttaaaatt gctgtgaatg tgatttatt caaaagggtt ctttatagtc
5281 tattaaacag catcttacta tataaaaagc cttgcaggaa aacacaggaa gcatattcag
5341 agttgaataa caataacttt cttttacag tttcatgtga ttcctatagt tttgatcttc
5401 agaaatattg cagagttctt tggcttcttt gataaatacc gagccttta aatattccct
5461 ctgagatttg cctgagactc ccgttaacat gagagaagct actcagctgg gtctctgtac
5521 attatgccac tgtctcccac tctgatattc tacatggtct tctatttaga atgccagcag
5581 cctttcaac agtttctgat catctttaag ttctgagctg gatgtatcac ccttgcaagc
5641 ctcccaggaa gttagaagct tctcttacgt gctttgcttt tgtgtttga caggctggaa
5701 gacccttcta tgtggtgatg ggaaatgaaa cttgctctcc agtctctgcc tctttttcag
5761 ccccatttc atcctgtaaa actagagtct gc
```

(SEQ ID NO: 5)

FIG. 5B

```
   1 ctacctctct gcaagccccg ccggccgcgc gttcggaccg agtatcgtct gcgctccgtg
  61 gacgcgccct ccgtccgccg accgacagaa ctgcctatac ccgcctgttc tccttgcggc
 121 ccggacacat agtatgacca ttagatattt cgtctaccaa ccattttcca tggaaaacca
 181 aagggaccag gccatgatag ccactggcag ctttgaagaa cgggacatct ttagagaagc
 241 ttgaccttga agacctcagc gtgggaccta acacagccgg tctccggcag agttcctctg
 301 tctcgtcttg ttgctgacag aaggtgcccc cttctccagt ttttgttcat ctcctgggag
 361 gttgcaggaa tcgtcattat ggttgggttc aaggccacag atgtgccccc tacagccact
 421 gtgaagttcc tgggggcagg cacagctgcc tgcattgcgg acctcatcac ctttcccctg
 481 gatactgcta aagtccggct acagatccaa ggagaaaggc aggggccaat gcaggctgcg
 541 gccagtgccc agtaccgcgg ggtgctgggc accatcctga ccatggtgcg caccgagggc
 601 ccccgcagcc tctacagcgg gctggtcgcc ggcctgcagc gccagatgag cttcgcctcc
 661 gtccgcatcg gcctctacga ctccgtcaag cagttctaca ccaagggctc tgagcatgct
 721 ggcatcggga gtcgcctcct ggcaggcagc accaccggtg ccttggccgt ggccgtggcc
 781 cagccaacgg atgtggtgaa ggtccggttc caagcacagg cccgagctgg agctggccgg
 841 aggtaccaga gcactgttga ggcctacaaa accattgccc gagaggaggg gtttcgggga
 901 ctctggaaag ggacatctcc caatgtcgct cgcaatgcca ttgtcaactg tgctgagctg
 961 gtgacctacg acctcatcaa ggacactctc ctgaaggccc acctaatgac agacgacctc
1021 ccttgccact ttacttctgc cttcggggcg ggcttctgca ccaccgtcat cgcctcccct
1081 gtcgacgtgg tcaagacgag atacatgaac tctgccctgg gccagtacag cagcgctggc
1141 cactgcgccc tcaccatgct ccagaaggag ggacccaag ccttctacaa agggttcatg
1201 ccctcctttc tccgcttggg atcctggaac gtggtgatgt tcgtcaccta cgagcagctg
1261 aagaggaccc tcatggctgc ccgcgcttcc cgggaggctc ccttctgagc agctgctgac
1321 ctgatcagcg ttggctctgg ctgcagcctg gccctgcttc cttttccttc ctccccttct
1381 cccccttccct ctctccccat ccctctcttc tgctccctct cccaccacct cccttccccc
1441 tccccacgtt ctcaccccett agctccctgt agcctctcac agtccaggtg gacttgaccc
1501 cagctgacac tgtgggagagc ctggcatcag ccaggatctc aagcccccag tccctagaa
1561 agccctcagc ttgactcttc ttcctgcccc cgagcccaac tagcacgtca cccataaaac
1621 aagctcaacc ttggtgtc
```

(SEQ ID NO: 6)

FIG. 6

```
GAATGGGTTTCACGGCACAGATGTGCCCCCTACAGCCACTGTGAAGTTCCTGGGGGCAGG
CACAGCTGCCTGCATTGCTGACCTCATCACCTTTCCCCTGGATACTGCTAAAGTCCGGCT
ACAGGTGAGTGAATGAAGCCTGCATTTCTGAGCGTAGCTAGTCCACTCCCTCCCCAGGAC
ACAGACTCTTCAAGGGCCAGTGGGGTTTTGGG [C/G] ACCATAAATTTTAGAGCACAGGGATGG
CAGGAGATGGGGAGGGCAACCACCTGCCTTGGCCTTGCAGATCCAAGGAGAAAGGCAGGG
GCCAATGCAGGCTGCGGCCAGTGCCCAGTACCGCGGGGTGCTGGGCACCATCCTGACCAT
GGTGCGCACCGAGGGCCCCCGCAGCCTCTACAGCGGGCTGGTCGCCGGCCTGCAGCGCCA
GATGAGCTTCGCCTCCGTCCGCATCGGCATCTACGACTCCGTCAAGCAGTACTAACAGGG
GAA
```

(SEQ ID NO: 7)

FIG. 7

SEQUENCE LISTING

```
<160> NUMBER OF SEQ ID NOS: 7

<210> SEQ ID NO 1
<211> LENGTH: 392
<212> TYPE: DNA
<213> ORGANISM: Bos taurus

<400> SEQUENCE: 1
tagaagtggt tgctcttgat cactttaaat gtgtgtctca ttaggaccat ccattaccct      60
cctgatttca tgacttgtct tgtcttttta ctctgcagat tcttctggga atcctaaatt     120
caccaagtgc cgttcacctg aactggagac tttctcatgt cactggacag atggggctaa    180
```

| | |
|---|---|
| tcacagttta cagagcccag gatctgtaca gatgttctat atcagaaggt atgggcttca | 240 |
| tgcttttctg atttctctcc atgaattttc tgatgaaaat ccattgagtg tcatgcagta | 300 |
| gtgggaatgg aaataatctt ctttggtgat ctaaatgcat tcacccattc attcatttaa | 360 |
| atatattagt taagccctta ctatatgttg gg | 392 |

<210> SEQ ID NO 2
<211> LENGTH: 3052
<212> TYPE: DNA
<213> ORGANISM: Bos taurus

<400> SEQUENCE: 2

| | |
|---|---|
| gaattcaaca attctattta tcaagaaatc tcccacaaat atactcacac tgtgctccaa | 60 |
| taagtacttt tgagtctatt aattaacaac attatgtatc taacattatg gttagattga | 120 |
| ttatggtgca tctgtgaaat gaaacatacg ctgactctaa aatgattggc acaatcctgt | 180 |
| gtattggtaa gaaattgtat tctagatata ctaggtgaaa gaagtgagat taataatggt | 240 |
| taaaattggg caatggtaca tggacatttg taatgccatt tttccttata agtgtattgt | 300 |
| ggagatttaa attttttccaa aaaaaaaaat gtggaggcag gggggcaagaa cattagtgtg | 360 |
| aataatatga cattatttaa atgcccttaa atatatattt tttaattaat ttatttattt | 420 |
| tttctatgct gggtcttcat tgcaatgtgc aagcttctca ctgtggcagc ttctcctgtt | 480 |
| gtggagcata ggctccaggt gcccagggac tcagcggttg caacacacag gctctagagc | 540 |
| ttgggctcgg gagccgtgtc acacggcctt tgttgctccc agcatgtgga atcttcctca | 600 |
| accagggacc gatcccgcgt ccctgcactg gcaggcggat tctcatccac tgtaccacca | 660 |
| aggaaggcct gcacactttt tttttttaagg aaatggatat atgaaggaca gaaaagaat | 720 |
| atccatggaa ggatacacca taaactgaga agaacaacta cttctaggga aaaaaggact | 780 |
| ggggagagac tgagttttca tatctttgtt ccttttgaat tttaagaaaa ataatacatt | 840 |
| attctaacac aacattgtaa agcaattata cttcaataaa aaattaaaag taaaaatact | 900 |
| ttattatata ataatatata attataatat aatataaaca ttcagttcag ttcagttcac | 960 |
| ttcagtcgct cagtcgtgtc cgactctttt cgaccccatg aatcgcagca caccaggcct | 1020 |
| ccctgtccat caccaactcc cggagttcac ccagactcat agtaatatat aataatttat | 1080 |
| tttaaaataa ttattaatca acacgaaatg taaaaaatag gtaggtgatg ggtagatagg | 1140 |
| cagacgggca gtccacacac tcacatgtgg tctcaagtgc tacttggtgt tcaggcaata | 1200 |
| actctggtcc caatctgacc tctgacccct aaaaggtga tggtaagaca agtaacctga | 1260 |
| ggctgccagg gcccctgcct atgagctaag actctgctta gaaccaagtt acaaagatgt | 1320 |
| tgcagacaag aaaaatttgg tcgtagtgga tgctactgcc tctatttgaa aaacaacaca | 1380 |
| aacatttccg ggggggggggg gaggcggaga ggaggaaaga ttttcttcaa aatgtaatttt | 1440 |
| cattgtagac acttctttaa aagaaacatt tctttatttg acagttccag gccttagttt | 1500 |
| cagcaggcag gatgtttagt cgcagcatga gaactcttag ctgcggcatg cgggacccag | 1560 |
| ttcagttccc tgaccagata tcgaacctgg ggccccctgca tttggaagca gggagtctta | 1620 |
| gccactggac caccagggaa gtcccctgta gatgttttta tgaaaagcag aaaagcacaa | 1680 |
| agaagagctt aaagattcct gatcctactc ccaatagtga taatgtatat ttggtgtga | 1740 |
| gagtgtgtgt attgattgga atgtgtgtga tcagaaaaca cataccatttt tataatccgt | 1800 |
| tctttccagc tcaaaaata aagttatttt cctacatcat taaatattac tttacaacat | 1860 |
| aattttttaat gtgtgcatat tgctgctatg tgattttcaa taacttacta atttcctatg | 1920 |

```
ctgaacattt agttgttgtc caaccttttt agtggccatg taattataaa tcatggtcaa    1980
tgctaacaat ttctgacctc acaaacatat agtacaatat ccttcctttc ttcaatagat    2040
aattattaaa agcaaaacaa ccaggctcaa acaaagcaat tataaaatat ctttaaaaag    2100
acattgggta aaattcaaat gcagactagc tcatgatgtt aaagaattac tcttgtgtgg    2160
taatggtctt gtgatagaga tagaaatgct tccttatttt tcagataaac acttaagtat    2220
ttaaggatga aacgccctga tgtttgtaat ttgctttaga atattttagc caaaagaatt    2280
aatgatgcaa atatgcaaaa agagtacgtt aaacctaaat ttgcgatttt catttaaaaa    2340
tatatcttaa aaatgaaaat cttcgtgcaa cgcacggggc tatcaatgtg ggatacagat    2400
gtgaacaaaa cggacccgtg tgggactcgg cggagcacac agattttgcg ggagcacgtt    2460
cccgttagga agtctctgat gcaatacgac cggtgcccct caggacctgt gagactgact    2520
ttccttaccc ctccacacca tcatcaaggc aggtgtgatt ttccaggcca ggcctacggc    2580
cgggtttccc cggggcccca gagccgtcgg gtcttgccgc ccagcggagc tggctgctcc    2640
ggcctcactg tcggggcgcc accgccccca gccggctcag aggaacccct caccgccacc    2700
ctgtcccagg cggcctttcc ccgaggcccg agggtcagat cctggggcca cctcgaggat    2760
ttctcacacc tgcccagcca cccccagctt ttcaggtgat accggagggt gggcgtgggg    2820
ctcctggcgc atccgagtcc ctccctggag tccccgaccg cggccgcccg gcccgacgct    2880
gccccgccgc cccgcagggc gggagccggc gctgcgggtg cgccccggcc agccgggcag    2940
ttgcgcaagt tgtgcttcgg cggctataag aggggcgggc aggcatggag ccccggaggg    3000
atcgaggaat cgcggcgcca gcagcggcga ggtaagtgcc cggctctctc ct          3052

<210> SEQ ID NO 3
<211> LENGTH: 786
<212> TYPE: DNA
<213> ORGANISM: Bos taurus

<400> SEQUENCE: 3
gaggcaaagg gcagggtggt ttgggaaggg cagaaagata ggagcccagg agaccagctt      60
ggaaacatgg tggtcacgtg ggcacaagaa gtaagggccc aggaggatgg tgtggaagc     120 gggggaggaa gcacctctac gctctaggga aaggcggagt caggggagct ctgaggagct    180
gccctctctc ccactgagct cttgctctcc ccttcctcct gcatagcagt ccgtctcctc    240
caaacagagg gtcactggtt tggacttcat ccctgggctc caccctctcc tgagtttgtc    300
caagatggac cagacattgg cgatctacca acagatcctc accagtctgc cttccagaaa    360
tgtggtccaa atatccaatg acctggagaa cctccgggac cttctccacc tgctggccgc    420
ctccaagagc tgccccttgc cgcaggtcag ggccctggag agcttggaga gcttgggcgt    480
tgtcctggaa gcttccctct actccaccga ggtggtggcc ctgagccggc tgcagggggtc    540 actacaggac atgttgcggc agctggacct cagtcccggg tgctgaagcc ttgaaggcct    600
ctcttcccaa agtccaggga agaaacctga gcttctggct gtccacagga aagagagcc    660 tatgtgggca tcctttatgc aggccagcgg gccatttctc tctcgctcct ctcagctgct    720
cttccaaagg cagaaaactg cgaggcagga aaccaaagat ataaatacag attccacgcc    780
caccgg                                                               786

<210> SEQ ID NO 4
<211> LENGTH: 344
<212> TYPE: DNA
<213> ORGANISM: Bos taurus
```

-continued

<400> SEQUENCE: 4

| | | | | | |
|---|---|---|---|---|---|
| gtccagggcc | ccagcttta | ggggacgggc | cgaagtggca | cagtccaact | ctgggccgct | 60 |
| cctctcgccg | ttacagcaca | tctcctccgc | cccctgtgga | agggaagcca | aaccggaggg | 120 |
| caacgggagg | agagcagaca | cagttgaggt | tttttttggtg | gttttctttt | ttttggctac | 180 |
| actgtaaagc | gtggggatct | taagttcccc | arccagggat | caaacccgtg | ccctgtagt | 240 |
| ggaagcatgg | agtcttaacc | agtggaccgc | cagggaagtc | ccggacacag | ctctttgact | 300 |
| tgacctcttg | cgtttcagaa | accctggcta | acgagtgagt | ggcc | | 344 |

<210> SEQ ID NO 5
<211> LENGTH: 5792
<212> TYPE: DNA
<213> ORGANISM: Bos taurus

<400> SEQUENCE: 5

| | | | | | |
|---|---|---|---|---|---|
| atgctgggta | gcaagcgact | ggggttgtcc | ggactgaccc | tcgccctgtc | cctgctcgtg | 60 |
| tgcctgggcg | ccctggccga | ggcgtacccc | tccaagcctg | acaacccgg | cgaggacgct | 120 |
| ccggcggagg | acttggccag | atactactca | gcgctgcgac | actacatcaa | tctcatcacc | 180 |
| aggcagaggt | aggtgggctg | cgcgggactc | acgactccgg | gagcgcccca | cttgcacacc | 240 |
| cggagatcat | gggcatcttg | aaggacaagg | tcttttttctt | tttmttttt | gtatcccagg | 300 |
| gccagacaac | atcaggcaca | tactcagctc | tcagtaaatg | tttgcacagg | gagcaactac | 360 |
| ctcggccact | actgtcacaa | aatcctgatc | cccagactca | ggtcctccag | tctgggggtc | 420 |
| tgactggcca | tttcctctca | cccatccctt | tgtcttttt | gttcttagag | cagtcggggg | 480 |
| actgtttgga | aacctggata | ggaaagtacc | cagtgaaagg | ggtcaggagg | gcgctgggag | 540 |
| gtggctatta | gctgagaggg | ctgcagggta | tctagaaaaa | taacagcaca | agctaggag | 600 |
| gaaacagctg | ggtcaccaaa | gacattgcca | gattttcag | cctgcccaga | ctgaagtgaa | 660 |
| aagacatcta | gaactatttc | ccccgtacag | tgttttattt | cggtctgaac | cccttacctg | 720 |
| aaaatcctgc | tcctaataag | tagagattta | gcatgaaaac | attagtctaa | aatgctgaga | 780 |
| cttttcccat | ttcatagcag | gtgagttcgg | aaaagaaaat | gcccacttgg | tgcttttta | 840 |
| aggagaaact | tacaatgatc | tgttcacttt | aggatgaatc | cagggattac | atgtactttg | 900 |
| agaaattgtc | atctttattc | tgaacccta | gaaagctaaa | atgaaaggcc | acatttcatt | 960 |
| ctcaacatca | aatcttaagc | aagaaatcaa | atccaaacta | ttttagaagt | aacataggat | 1020 |
| ttaaaatttg | tttccaaaat | taattcatct | tagttttgaa | tcattcaatt | tttaaaatta | 1080 |
| ctgagatcaa | atgtccttaa | taagctgaaa | acaatgagct | ttattactga | gatcaaatgc | 1140 |
| ccttaacaag | ctgaaaacaa | tgagcttttt | acaaagttta | atgttattta | acatatttat | 1200 |
| gttttttaaag | tattgttttt | tctttgctgt | tttactatat | ttcaaggaat | agttggaaag | 1260 |
| aatttaaagt | ggggaaaaat | ttgtattaaa | gaaaactcta | actttgatga | aactttctgt | 1320 |
| ttcatcaaaa | agcttttaaa | gaaccaattt | atatgaaatt | agaaatatat | gaaaatgcta | 1380 |
| gaattaaata | gcattggttt | atgatccctg | aagtctgata | cttttcatta | gtgaaaagca | 1440 |
| agaatgtctt | atatcttaat | agaccttcag | aaagttaatt | gcttcatatt | cttgcttatg | 1500 |
| catcataaag | accagagaaa | aaactgtaca | aattgttttt | ttttcccct | aggaaagact | 1560 |
| ttgttagtta | tttagcctgt | taattatagc | atataatggg | aacttagttt | tacaaagatg | 1620 |
| attgatataa | acctttacta | ttgggtaaag | ctttggcatt | tcaaaatgtt | ttccagtcta | 1680 |
| ttaccttgtc | cagcttttga | aggggagtat | aaattatccc | cccagttttc | cagatccatg | 1740 |

```
aaattaagga catttcatgg aaaccttttt tagggggtga ttaaattgga gccctcctct   1800
tgatctctgg atgttgtcac tactatcagc acttagagtg atcttcaata cctttgagga   1860
ggagaaaata agggaaaggg ctaatattca ggttagcaag tgttcctgaa gcagtttcct   1920
atctcctttt catataagtt ccttcttaga aacactcaga ggctcataat ctgcacccat   1980
cacctccatt ctatactctc atcatcttcc caccacacac atccactcat ctgcacattt   2040
gtattttga aaattacgtt tatacacata cattttaatt tggtatagat ggtactgtga    2100
tattctcttt cctcccsttt tctacttggt tcatgttcta aagctatata ctcctcgttc   2160
attgcttcca aaggtggcat catttattct agagcataga tctaccgcat tttatttta    2220
cagtcatcta tatcagtggt tctcaactgg ggttgacttt atgctcccca agacattggg   2280
caatatctgg agacgttttc agttgtcata atggtgggat ggggtggggt ggggtggggt   2340
ggcatggggg ctactactgg catctagtga gtagaggcca gggacgctgc tgaacatctg   2400
cggtccctag acagcccctt gacaataaag aattatccag ctcaaaatgt gcacagtgcc   2460
aagactgaga aactcagccc tggactagag tttcttcctc ctagtctcat tgttatcatc   2520
tggggaactt ttagaatata ctgatgctga gccgcacccc tgaggagtta atcagaatc    2580
tcccagaagg tgggacatgg gctttttaaa accccagg gtgattctaa catctagcca     2640
ggtttgattt tcctagagat gctatctttg aaagataaag cattgtcaag aagaaggata   2700
atccagaatt aattcgagat gggagaacag tcattgatgc tgctctgggt acctactact   2760
ttctgactac aaattctgct attgcagact aagttctct aatggtaaat tggagaaaat    2820
attccaccagt tctttaattc actgcagcat gatgaaaata aacgagttaa ggttgcccaa   2880
gagttttagg attagtaaaa tcaactgatg gacagaataa atacatataa attgctgcct   2940
acagtctgat atcacaacac cagaaaatct ttgaggaaat ctcgcaaatg atgggggcga   3000
gagagttggc tttgcttttg tattccttga gyccctgcaa aggagcaata ataggaacgt   3060
tttcctccaa atttagattt aattgtgctt gataggcagc tagcatatac tctctatcag   3120
ctttattcca cctgttttat ctgatatcta atcaatccac cagtagacta tttttttatt   3180
tgtgaaaaaa agcagctact gatgtccaat gctctttttg agaaagggaa aaatagtgtc   3240
ttcaaaaaaa tacaacttgg tgtagatttc tcagctcctt tggcagagag agagagacag   3300
acaaacagac catgtcctca ctcacctggg gccagcagca tatactaccc tggcaggaaa   3360
acataacctt gaatccatat attgttctac ccatacctg ctatgggaga aaagagacta    3420
cccataccct gctatgggag aaaagagacc aagaacattt ctatgaccca gtaggtttcc   3480
ttcatatttt cagggcagtt taaaatcatg ttaggagaga agacttttag ctttttggcac  3540
cccaaataaa catggaaaat ataggactca gaatctgttg gtagctgtga aatggatgc    3600
atttcagcag cagtaatgtg catttttgta tatcactctg ttgctttcag agcattgtga   3660
cttacagtgg atattcatca agattctaat ttaagcagga gttatgattt tgttgatgtt   3720
ttatatttaa taccacaaat ctttcttttc taaaggtgtt tatggtttct ccaaacttgc   3780
cttaaaggac ttttactccc ccaacccatt tttttcttcc agatacggga aacgatctag   3840
ccccgagacc ctgatttcag acctcttgat gagagaaagc acgggaaaca ttcccagaac   3900
taggtatgaa aagacttagt gggaacactg ttgcagagct caaggtggtc agggaaagga   3960
aatcagagag gactgctgga agaaggtgtt gggatggggt cctccagacc aggtaagatt   4020
tggacagaaa gagtgatggg gaacagagca tggaggacct ttctcttcac atactcattt   4080
acaaatctct gaacttgtgg gataatattt tctgattcaa cttaatttga tgctcctttg   4140
```

```
aaattttcaa atataaatga tttttgcctc aaaaattact ctatagaaaa tttctgattg    4200
acttagattg gggaagcata gggtatgccc taatatctac attgaaataa ccaactgtct    4260
gtctttggct gaggtaatct ttagttctta tagtctacgc agaggattta cacatccttg    4320
gaaatgttcc ctcctggctt cactccagtc acactggttt tacaagaagc tgtagataaa    4380
tcaaggggtg ctcctgttta cttttttgact tattttagtt catctgatgt cacattgtaa    4440
tttatcacat tcagtgaatg agcattgaac aacatgttat tcttagggct tgcttggaaa    4500
cttggggctt tcttggagtg tggagctgcc tcaggacagg tgccctctaa tatctaggtg    4560
tcaaacattg ggctgggtc attctaggta aagactgaaa gtgaaaagac gcctgctcct    4620
cctccttttc catagctggc tctcctgtcc caggcccact gtcccttccc ccagtaagat    4680
ggcctgtcta cctaaaccc agagctctac aacatcaaga accaagctcc ccagaagagg    4740
tcactagaac acttgctcag tgcatgtgac tggcttgtca ctcttcattg ggttctccct    4800
ctgttctctt gtgcaatggc caggcagtgg aaggtgcaa gtctagagtt gtcaggtttg    4860
ttttctctga aggacacaca atttggattg aataaaact cagtgctctt gtccctggtg    4920
gcactagcag acttgaacag caaatgcaag ggaagcaggg ggaaaactca taaaggtggt    4980
tttaaaatac taagcaatac atgctttaat gtttcattaa taggcatatg atgtttgtca    5040
cagtaataag tttaggatat gctatatcta ctcaagatta gaaatatgat catccagacc    5100
aacctacagc cttaacgctg ttctttgttt tgtggcccaa agtcacatgg ctggtgaatg    5160
aaatagagtt aattgtactc tgattgacag cttcaatcat gtgcacttag aaggagacaa    5220
aacctgacag ccttaaaatt gctgtgaatg tgattttatt caaaagggtt ctttatagtc    5280
tattaaacag catcttacta tataaaaagc cttgcaggaa aacacaggaa gcatattcag    5340
agttgaataa caataacttt cttttttacag tttcatgtga ttcctatagt tttgatcttc    5400
agaaatattg cagagttctt tggcttcttt gataaatacc gagccttta aatattccct    5460 ctgagatttg cctgagactc ccgttaacat gagagaagct actcagctgg gtctctgtac    5520
attatgccac tgtctcccac tctgatattc tacatggtct tctatttaga atgccagcag    5580
ccttttcaac agtttctgat catctttaag ttctgagctg gatgtatcac ccttgcaagc    5640
ctcccaggaa gttagaagct tctcttacgt gctttgcttt tgtgtttga caggctggaa    5700 gaccccttcta tgtggtgatg ggaaatgaaa cttgctctcc agtctctgcc tctttttcag    5760
cccccatttc atcctgtaaa actagagtct gc                                5792

<210> SEQ ID NO 6
<211> LENGTH: 1638
<212> TYPE: DNA
<213> ORGANISM: Bos taurus

<400> SEQUENCE: 6
ctacctctct gcaagccccg ccggccgcgc gttcggaccg agtatcgtct gcgctccgtg     60
gacgcgccct ccgtccgccg accgacagaa ctgcctatac ccgcctgttc tccttgcggc    120
ccggacacat agtatgacca ttagatattt cgtctaccaa ccattttcca tggaaaacca    180
aagggaccag gccatgatag ccactggcag ctttgaagaa cgggacatct ttagagaagc    240
ttgaccttga agacctcagc gtgggaccta acacagccgg tctccggcag agttcctctg    300
tctcgtcttg ttgctgacag aaggtgcccc cttctccagt ttttgttcat ctcctgggag    360
gttgcaggaa tcgtcattat ggttgggttc aaggccacag atgtgccccc tacagccact    420
gtgaagttcc tgggggcagg cacagctgcc tgcattgcgg acctcatcac ctttcccctg    480
```

```
gatactgcta aagtccggct acagatccaa ggagaaaggc aggggccaat gcaggctgcg    540
gccagtgccc agtaccgcgg ggtgctgggc accatcctga ccatggtgcg caccgagggc    600
ccccgcagcc tctacagcgg gctggtcgcc ggcctgcagc gccagatgag cttcgcctcc    660
gtccgcatcg gcctctacga ctccgtcaag cagttctaca ccaagggctc tgagcatgct    720
ggcatcggga gtcgcctcct ggcaggcagc accaccggtg ccttggccgt ggccgtggcc    780
cagccaacgg atgtggtgaa ggtccggttc aagcacagg cccgagctgg agctggccgg    840
aggtaccaga gcactgttga ggcctacaaa accattgccc gagaggaggg gtttcgggga    900
ctctggaaag ggacatctcc caatgtcgct cgcaatgcca ttgtcaactg tgctgagctg    960
gtgacctacg acctcatcaa ggacactctc ctgaaggccc acctaatgac agacgacctc   1020
ccttgccact ttacttctgc cttcggggcg ggcttctgca ccaccgtcat cgcctccct   1080 gtcgacgtgg tcaagacgag atacatgaac tctgccctgg gccagtacag cagcgctggc   1140
cactgcgccc tcaccatgct ccagaaggag ggacccaag ccttctacaa agggttcatg    1200
ccctcctttc tccgcttggg atcctggaac gtggtgatgt tcgtcaccta cgagcagctg   1260
aagagggccc tcatggctgc ccgcgcttcc cgggaggctc ccttctgagc agctgctgac   1320
ctgatcagcg ttggctctgg ctgcagcctg gccctgcttc cttttccttc ctcccttct   1380 cccttccct ctctccccat ccctctcttc tgctccctct cccaccacct cccttccccc   1440
tccccacgtt ctcaccccct agctccctgt agcctctcac agtccaggtg gacttgaccc   1500
cagctgacac tgtggagagc ctggcatcag ccaggatctc aagcccccag tccctagaa   1560 agccctcagc ttgactcttc ttcctgcccc cgagcccaac tagcacgtca cccataaaac   1620
aagctcaacc ttggtgtc                                                 1638

<210> SEQ ID NO 7
<211> LENGTH: 483
<212> TYPE: DNA
<213> ORGANISM: Bos taurus

<400> SEQUENCE: 7
gaatgggttt cacggcacag atgtgccccc tacagccact gtgaagttcc tgggggcagg     60
cacagctgcc tgcattgctg acctcatcac ctttcccctg gatactgcta aagtccggct    120
acaggtgagt gaatgaagcc tgcatttctg agcgtagcta gtccactccc tccccaggac    180
acagactctt caagggccag tggggttttg ggsaccataa attttagagc acagggatgg    240
caggagatgg ggagggcaac cacctgcctt ggccttgcag atccaaggag aaaggcaggg    300
gccaatgcag gctgcggcca gtgcccagta ccgcggggtg ctgggcacca tcctgaccat    360
ggtgcgcacc gagggcccc gcagcctcta cagcgggctg gtcgccggcc tgcagcgcca    420
gatgagcttc gcctccgtcc gcatcggcat ctacgactcc gtcaagcagt actaacaggg    480
gaa                                                                  483
```

POLYMORPHISMS IN GROWTH HORMONE RECEPTOR, GHRELIN, LEPTIN, NEUROPEPTIDE Y, AND UNCOUPLING PROTEIN 2 GENES AND THEIR ASSOCIATIONS WITH MEASURES OF PERFORMANCE AND CARCASS MERIT IN BEEF CATTLE

INCORPORATION BY REFERENCE

This application claims benefit of U.S. provisional patent application Ser. Nos. 60/758,616 filed Jan. 13, 2006 and 60/836,777 filed Aug. 10, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of a single nucleotide polymorphisms (SNPs) within the bovine genes encoding growth hormone receptor (GHR), ghrelin, leptin, neuropeptide Y (NPY), and Uncoupling Protein 2 (UCP2) and their association with economically relevant traits in beef production. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals with an advantage for an inheritable trait of circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection. In the present study, associations between single nucleotide polymorphisms (SNPs) in the bovine growth hormone receptor (GHR), bovine neuropeptide Y (NPY), leptin, ghrelin and uncoupling protein 2 (UCP2) genes with measures of intake, growth and carcass merit in beef cattle.

The GHR is bound by GH in a homodimeric group resulting in the initiation of signal transduction mechanisms and the subsequent activation of many hormonal systems involved in growth promotion as well as lipid, nitrogen, mineral and carbohydrate metabolism. The interactions between GH and its receptor also affect protein synthesis, protein degradation, and regulation of overall protein turnover. Other areas of activity are effects on nitrogen retention, fat synthesis, fatty acid oxidation, and stimulation of fatty acid mobilization from body adipose tissues. Treatment of farm animals with growth hormone has been shown to lead to decreased feed intake, increased average daily gain, increased feed efficiency, decreased fat accretion and increased protein accretion.

Ghrelin is a growth hormone releasing peptide, consisting of 28-amino acids, which serves as an endogenous ligand for growth hormone-secretagogue (G-protein-coupled). These receptors in turn stimulate the release of GH from the pituitary gland. In addition, ghrelin has also been shown to play important roles in the stimulation of appetite and feeding activity through interactions with peptides such as NPY.

Leptin, the hormone product of the ob (obese) gene, has been shown to be predominantly synthesized and expressed in adipose tissues. It functions as a potent physiological signal in the regulation of body weight, energy expenditure, feed intake, adiposity, fertility and immune functions. Leptin has been proposed as one of the major control factors contributing to the phenotypic and genetic variation in the performance and efficiency of cattle.

Polymorphisms in the coding regions of the leptin gene in cattle have been associated with milk yield and composition (see, e.g., Liefers et al., J Dairy Sci. 2002 June; 85(6):1633-8), feed intake (see, e.g., Liefers et al., J Dairy Sci. 2002 June; 85(6):1633-8; Lagonigro et al., Anim Genet. 2003 October; 34(5):371-4), and body fat (see, e.g., Buchanan et al., Genet Sel Evol. 2002 January-February; 34(1):105-16; Lagonigro et al., Anim Genet. 2003 October; 34(5):371-4). Polymorphisms in the leptin promoter have been identified, specifically the UASMS1, UASMS2, UASMS3, E2JW, and E2FB SNPs (see, e.g., Nkrumah et al., J Anim Sci. 2005 January; 83(1):20-8; Schenkel et al., J Anim Sci. 2005 September; 83(9):2009-20) and the A59V SNP (see, e.g., Liefers et al., Mamm Genome. 2003 September; 14(9):657-63), however, only the UASM2 SNP (see, e.g., Nkrumah et al., J Anim Sci. 2005 January; 83(1):20-8) has been associated with serum leptin concentration and economically relevant traits of growth, feed intake, efficiency and carcass merit in cattle.

Neuropeptide Y is a 36-amino acid peptide that plays a powerful role as a central appetite stimulator playing important roles in the regulation and control of food intake and energy-balance. It stimulates food intake and induces a general anabolic state by reducing energy expenditure. Additionally, NPY influences the regulation of growth in animals by causing a dose-dependent inhibition of GH release, and a lowering of plasma GH and IGF-1 concentration through the stimulation of somatostatin.

Uncoupling proteins are proteins that can uncouple ATP production from mitochondrial respiration, by causing a proton leakage, leading to the dissipation of energy as heat. Although certain uncoupling proteins have been shown to influence variations in metabolic efficiency and thermogenesis, the role of UCP2 in energy balance is currently unclear. Nevertheless, UCP2 has been shown to regulate insulin secretion, and it is up-regulated by a high-fat diet, suggesting UCP2 to be important for determining basal metabolic rate and possibly resistance to obesity. Most importantly, significant genetic linkage has been established between microsatellite markers encompassing the location of UCP2 with resting metabolic rate, body mass, body fatness and fat mass in humans.

It remains advantageous to provide further SNPs that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of a single nucleotide polymorphisms (SNPs) within the bovine genes encoding growth hormone receptor (GHR), ghrelin, leptin, neuropeptide Y (NPY), and Uncoupling Protein 2 (UCP2) and their association with economically relevant traits in beef production.

The invention encompasses a method for sub grouping animals according to genotype wherein the animals of each sub-group have a similar polymorphism in a GHR, ghrelin, leptin, NPY or UCP2 gene which may comprise determining the genotype of each animal to be subgrouped by determining the presence of a single nucleotide polymorphism in the GHR, ghrelin, leptin, NPY or UCP2 gene, and segregating individual animals into sub-groups wherein each animal in a subgroup has a similar polymorphism in the GHR, ghrelin, leptin, NPY or UCP2 gene.

The invention also encompasses a method for sub grouping animals according to genotype wherein the animals of each sub-group have a similar genotype in the GHR, ghrelin, leptin, NPY or UCP2 gene which may comprise determining the genotype of each animal to be subgrouped by determining the presence of a single nucleotide polymorphism(s) of interest in the GHR, ghrelin, leptin, NPY or UCP2 gene, and segregating individual animals into sub-groups depending on whether the animals have, or do not have, the single nucleotide polymorphism(s) of interest in the GHR, ghrelin, leptin, NPY or UCP2 gene.

The single nucleotide polymorphism(s) of interest may be selected from the group consisting of an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene and a C to G substitution at position 213 in intron 2 of the UCP2 gene.

The invention further relates to a method for sub grouping animals according to genotype wherein the animals of each sub-group have a similar genotype in the GHR, ghrelin, leptin, NPY or UCP2 gene which may comprise determining the genotype of each animal to be subgrouped by determining the presence of any one of the above SNPs, and segregating individual animals into sub-groups depending on whether the animals have, or do not have, any one of the above SNPs in the GHR, ghrelin, leptin, NPY or UCP2 gene.

The invention also relates to method for identifying an animal having a desirable phenotype relating to certain feed intake, growth rate, body weight, carcass merit and composition, and milk yield, as compared to the general population of animals of that species, which may comprise determining the presence of a single nucleotide polymorphism in the GHR, ghrelin, leptin, NPY or UCP2 gene of the animal, wherein the presence of the SNP is indicative of a desirable phenotype relating to certain feed intake, growth rate, body weight, carcass merit and composition, and milk yield.

In an advantageous embodiment, the animal may be a bovine. In another advantageous embodiment, the GHR, ghrelin, leptin, NPY or UCP2 gene may be a bovine GHR, ghrelin, leptin, NPY or UCP2 gene.

The invention also encompasses computer-assisted methods and systems for improving the production efficiency for livestock having marketable tender meat using multiple data, and in particular the genotype of the animals as it relates to GHR, ghrelin, leptin, NPY or UCP2 SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the GHR, ghrelin, leptin, NPY or UCP2 gene related to meat quality traits of the breed of animal and associating that data with other data about the animal or its herd, and maintaining that data in ways that are accessible. Another aspect of the invention encompasses a computer-assisted method for predicting which livestock animals possess a biological difference in meat quality, and which may include the steps of using a computer system, e.g., a programmed computer comprising a processor, a data storage system, an input device and an output device, the steps of: (a) inputting into the programmed computer through the input device data that includes a genotype of an animal as it relates to any one of the GHR, ghrelin, leptin, NPY or UCP2 SNPs described herein, (b) correlating meat quality predicted by the GHR, ghrelin, leptin, NPY or UCP2 genotype using the processor and the data storage system and (c) outputting to the output device the meat quality correlated to the GHR, ghrelin, leptin, NPY or UCP2 genotype, thereby predicting which livestock animals possess a particular meat quality.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a GHR, ghrelin, leptin, NPY or UCP2 genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts the nucleotide sequence of a GHR gene (Accession No. AY643807, species, *bos taurus*), SEQ ID NO: 1;

FIG. 2 depicts the nucleotide sequence of a bovine leptin promoter (GenBank accession no. AB070368, species, *bos taurus*), SEQ ID NO: 2;

FIG. 3 depicts the nucleotide sequence of a bovine leptin promoter (GenBank accession no. BTA512639; EMBL Accession no. AJ512639), SEQ ID NO: 3;

FIG. 4 depicts the nucleotide sequence of intron 3 of the bovine ghrelin gene (unpublished) SEQ ID NO: 4 with a SNP indicated in brackets;

FIG. 5 depicts the nucleotide sequence of a bovine leptin promoter (intron 2 of the NPY gene (Accession No. AY491054, species *bos taurus*), SEQ ID NO: 5;

FIG. 6 depicts the nucleotide sequence of exon 4 of the bovine UCP2 gene (Accession No. XM_614452, species *bos taurus*), SEQ ID NO: 6;

FIG. 7 depicts the nucleotide sequence of intron 2 of the UCP2 gene (unpublished) SEQ ID NO: 7 with a SNP indicated in brackets.

DETAILED DESCRIPTION

Figure 8:
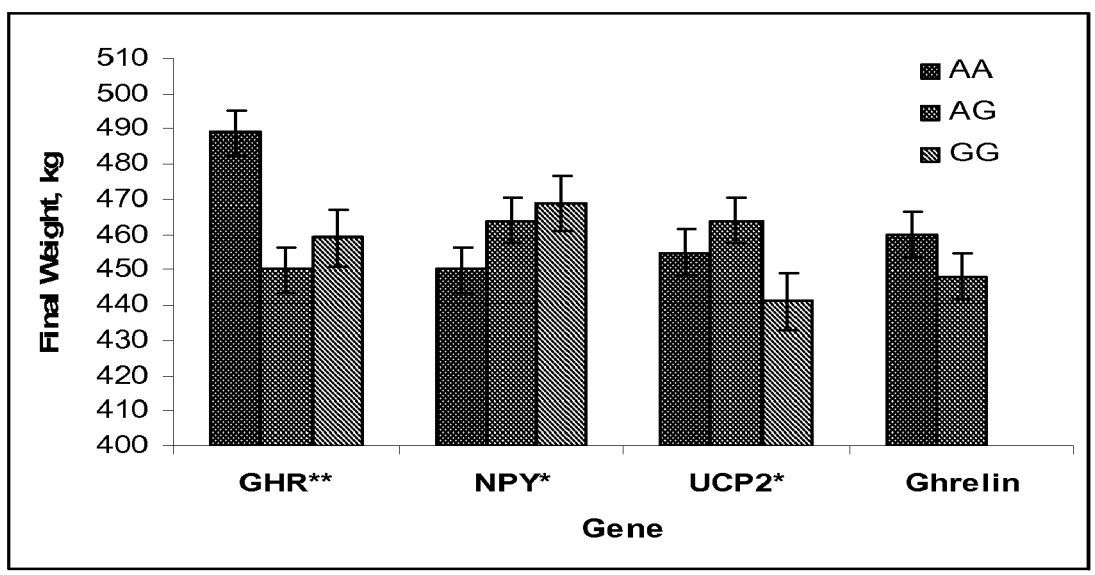
FIG. 8 illustrates the associations of SNP genotypes with final weight of beef steers (least square means±SE). Significant differences between genotypes of the SNP denoted as: *$P<0.05$, $P<0.01$, *$P<0.001$, and no *$P<0.10$.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphisms sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides liked by a phosphodiester backbone. A "modified polynucleotide" refers to a polynucleotide in which one or more natural nucleotides have been partially or substantially completely replaced with modified nucleotides.

A "primer" is an oligonucleotide, the sequence of at least of portion of which is complementary to a segment of a template DAN which to be amplified or replicated. Typically primers are used in performing the polymerase chain reaction (PCR). A primer hybridized with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality and quantity of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine growth hormone receptor (GHR), the bovine GHR nucleotide sequence can be selected from, but is not limited to, the sequence corresponding to GenBank Accession No. AY643807 or a fragment thereof or a region of the bovine genome that comprises this sequence.

The present invention, therefore, provides isolated nucleic acids that may specifically hybridize to the nucleotide sequence corresponding to GenBank Accession No. AY643807, or the complement thereof, and which comprises the polymorphic site corresponding to nucleotide position 300 in intron 4 of the bovine GHR gene, in particular a specific adenine (A) to guanine (G) mutation at that position.

The SNP advantageous in the present invention is associated with certain economically valuable heritable traits relating to meat quality in bovines. Therefore, it is an object of the present invention to determine the genotype of a given animal of interest as defined by the GHR locus SNP according to the present invention. It is also contemplated that the genotype of the animal(s) may be defined by additional SNPs within the GHR gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to growth, feed intake, efficiency and carcass merit, to be identified based on the presence of SNPs in their genomes and particularly with an SNP located within intron 4 of the GHR gene. The methods further allow, by computer-assisted methods of the invention, to correlate the SNP-associated traits with other data pertinent to the well-being and productive capacity of the animals, or group of animals.

In an embodiment wherein the gene of interest is ghrelin, the bovine ghrelin nucleotide sequence can be selected from, but is not limited to, the sequence corresponding to the bovine ghrelin nucleotide sequence described in the Examples or a fragment thereof or a region of the bovine genome that comprises this sequence.

The present invention, therefore, provides isolated nucleic acids that may specifically hybridize to the nucleotide sequence corresponding to the sequence corresponding to the bovine ghrelin nucleotide sequence described in the Examples, or the complement thereof, and which comprises the polymorphic site corresponding to nucleotide position in intron 3 of the bovine ghrelin gene, in particular a specific adenine (A) to guanine (G) mutation at that position (see below for sequence data).

The SNP advantageous in the present invention is associated with certain economically valuable heritable traits relating to meat quality in bovines. Therefore, it is an object of the present invention to determine the genotype of a given animal of interest as defined by the ghrelin locus SNP according to the present invention. It is also contemplated that the genotype of the animal(s) may be defined by additional SNPs within the ghrelin gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to growth, feed intake, efficiency and carcass merit, to be identified based on the presence of SNPs in their genomes and particularly with an SNP located within intron 3 of the ghrelin gene. The methods further allow, by computer-assisted methods of the invention, to correlate the SNP-associated traits with other data pertinent to the well-being and productive capacity of the animals, or group of animals.

In an embodiment wherein the gene of interest is leptin, the leptin nucleotide sequence can be selected from, but is not limited to, the sequence corresponding to GenBank Accession No. AB070368 (see, e.g., Taniguchi et al., IUBMB Life. 2002 February; 53(2):131-5) or a fragment thereof or a region of the bovine genome that comprises this sequence, or the sequence corresponding to GenBank Accession No. BTA512639 (see, e.g., Liefers et al., Mamm. Genome 14 (9), 657-663 (2003)) or a fragment thereof or a region of the bovine genome that comprises this sequence The present invention, therefore, provides isolated nucleic acids that may specifically hybridize to the nucleotide sequence corresponding to GenBank Accession No. AB070368, or the complement thereof, and which comprises the polymorphic site corresponding to nucleotide position 528 of the bovine leptin gene, in particular a specific cytosine (C) to thymine (T) mutation at that position. The present invention also provides isolated nucleic acids that may specifically hybridize to the nucleotide sequence corresponding to GenBank Accession No. BTA512639, or the complement thereof, and which comprises the polymorphic site corresponding to nucleotide position 321 of the bovine leptin gene, in particular a specific cytosine (C) to thymine (T) mutation at that position.

The SNP advantageous in the present invention is associated with certain economically valuable heritable traits relating to meat quality in bovines. Therefore, it is an object of the present invention to determine the genotype of a given animal of interest as defined by the leptin locus SNP according to the present invention. It is also contemplated that the genotype of the animal(s) may be defined by additional SNPs within the leptin gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to growth, feed intake, efficiency and carcass merit, to be identified based on the presence of SNPs in their genomes and particularly with an SNP located within the leptin gene. The methods further allow, by computer-assisted methods of the invention, to correlate the SNP-associated traits with other data pertinent to the well-being and productive capacity of the animals, or group of animals.

In an embodiment wherein the gene of interest is bovine neuropeptide Y (NPY), the bovine NPY nucleotide sequence can be selected from, but is not limited to, the sequence corresponding to GenBank Accession No. AY491054 (see, e.g., Thue & Buchanan, Anim Genet. 2004 June; 35(3):245-6) or a fragment thereof or a region of the bovine genome that comprises this sequence.

The present invention, therefore, provides isolated nucleic acids that may specifically hybridize to the nucleotide sequence corresponding to GenBank Accession No. AY491054, or the complement thereof, and which comprises the polymorphic site corresponding to nucleotide position 666 in intron 2 of the bovine NPY gene, in particular a specific adenine (A) to guanine (G) mutation at that position.

The SNP advantageous in the present invention is associated with certain economically valuable heritable traits relating to meat quality in bovines. Therefore, it is an object of the present invention to determine the genotype of a given animal of interest as defined by the NPY locus SNP according to the present invention. It is also contemplated that the genotype of the animal(s) may be defined by additional SNPs within the NPY gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to growth, feed intake, efficiency and carcass merit, to be identified based on the presence of SNPs in their genomes and particularly with an SNP located within intron 2 of the NPY gene. The methods further allow, by computer-assisted methods of the invention, to correlate the SNP-associated traits with other data pertinent to the well-being and productive capacity of the animals, or group of animals.

In an embodiment wherein the gene of interest is bovine uncoupling protein 2 (UCP2) gene, the bovine UCP2 nucleotide sequence can be selected from, but is not limited to, the sequence corresponding to GenBank Accession No. XM_614452 or a fragment thereof or a region of the bovine genome that comprises this sequence.

The present invention, therefore, provides isolated nucleic acids that may specifically hybridize to the nucleotide sequence corresponding to GenBank Accession No. XM_614452, or the complement thereof, and which comprises the polymorphic site corresponding to nucleotide position 812 of exon 4 in the bovine UCP2 gene, in particular a specific adenine (A) to guanine (G) mutation at that position (UCP2 SNP2). The present invention also provides isolated nucleic acids that may specifically hybridize to the nucleotide sequence (see nucleotide sequence provided below for UCP2 SNP1) which comprises a cytosine (C) to guanine (G) substitution at position 213 in intron 2 of the bovine UCP2 gene sequence provided (please see nucleotide sequence below).

The SNP advantageous in the present invention is associated with certain economically valuable heritable traits relating to meat quality in bovines. Therefore, it is an object of the present invention to determine the genotype of a given animal of interest as defined by the UCP2 locus SNP according to the present invention. It is also contemplated that the genotype of the animal(s) may be defined by additional SNPs within the UCP2 gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to growth, feed intake, efficiency and carcass merit, to be identified based on the presence of SNPs in their genomes and particularly with an SNP located within exon 4 or intron 2 of the UCP2 gene. The methods further allow, by computer-assisted methods of the invention, to correlate the SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the GHR, ghrelin, leptin, NPY or UCP2 gene, advantageously of the region encompassing a GHR, ghrelin, leptin, NPY or UCP2 SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a GHR, ghrelin, leptin, NPY or UCP2 gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a GHR, ghrelin, leptin, NPY or UCP2 gene which are unique to a GHR, ghrelin, leptin, NPY or UCP2 gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^{3}H$, $^{125}I$; $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises an SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

An SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the GHR, ghrelin, leptin, NPY and UCP2 gene polymorphic sites associated with economically relevant traits of growth, feed intake, efficiency and carcass merit, would lead to a breed, line, or population having higher numbers of offspring with economically relevant traits of growth, feed intake, efficiency and carcass merit. Thus, the GHR, ghrelin, leptin, NPY and UCP2 SNPs of the present invention can be used as a selection tool.

One aspect of the present invention provides for grouping animals and methods for managing livestock production comprising grouping livestock animals such as cattle according the genotype as defined by panels of SNPs, each panel comprising at least one SNP, one or more of which are GHR, ghrelin, leptin, NPY and UCP2 SNPs of the present invention. Other SNPs that may be included in panels of SNPs include, but not limited to, calpastatin, UASMS1, UASMS2, UASMS3 and/or EXON2-FB SNPs of the ob loci defining the same phenotypic character. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, food consumption, carcass/meat quality and milk production. The present invention provides methods of screening livestock to determine those more likely to develop a desired body condition by identifying the presence or absence of one or more of which are GHR, ghrelin, leptin, NPY and UCP2 polymorphism in genes that is correlated with that meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feed lot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feed lot operator, and then slaughtered.

Thus, a feeder is presented with opportunities for considerable efficiencies. At present, for example, the feeder may feed his cattle in the same manner, incurring the same costs for each animal, and typically, with excellent management practices, perhaps 40% will grade AAA and receive the premium price for the palatability grade depending on several other factors, such as age of animal, since cattle between 17-24 months of age have increased marbling compared to their younger counterparts. Approximately 55% of cattle are slaughtered at an age under 16 months, and 45% would be slaughtered at an age over 17 months. Of these, a significant number will have excess fat and will thus receive a reduced yield grade. The balance of the cattle, 60%, will grade less than AAA, and thus receive a reduced price, although the feedlot costs incurred by the operator will be the same. Grouping and feeding the cattle by genotype, as well as by other factors such as the overall welfare profile, which includes husbandry and veterinary data, allows the feeder to treat each group differently with a view to increasing profit by maximizing, for example, the number of cattle providing marketable tender meat.

The individual genotypic data derived from a panel or panels of SNPs of each animal or a herd or flock of animals can be recorded and associated with various other data of the animal, e.g. health information, parentage, husbandry conditions, vaccination history, herd or flock records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a flock or herd. If the performance or properties of the animals deviates from the desired goals, the computer-based methods may trigger an alert to allow the operator to adjust vaccination doses, medications, feed etc accordingly.

The results of the analysis provide data that is associated with the individual animal or to the herd in whole or in part from which the sample was taken. The data is then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd or flock, health information including vaccinations, exposure to diseases, feed lot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and vials useful for collecting samples from which genetic data may be obtained. The vials are packaged in a container that is encoded with identifying indicia. Advantageously, the packaging is encoded with a bar code label. The vials are encoded with the same identifying indicia, advantageously with a matching bar code label. Optionally, the packaging contains means for sending the vials to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the vials and the packaging. Upon shipment of the sampling equipment in fulfillment of the order, the identifying indicia are recorded in a database. Advantageously, the identifier is a bar code label which is scanned when the vials are sent. When the vials are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, SUREBRED pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. This data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g. POWERPOINT), internet, email, documentary communication such as computer programs (e.g. WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted to a feedstock site when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd or flock data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), Bovine spongiform encephalopathy (BSE) diagnosis, brucellosis vaccination, FMD (foot and mouth disease) vaccination, BVD (bovine viral diarrhea) vaccination, SUREBRED preconditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype and feeding the animal a diet based upon the physical characteristic, thereby improving livestock production.

The invention further provides for a computer-assisted method for optimizing efficiency of feed lots for livestock comprising using a computer system, e.g., a programmed computer comprising a processor, a data storage system, an input device and an output device, and the steps of inputting into the programmed computer through the input device data comprising a breeding, veterinary etc history of an animal, correlating the breeding, veterinary etc histories using the processor and the data storage system, outputting to the output device the physical characteristic correlated to the genotype and feeding the animal a diet based upon the physical characteristic, thereby optimizing efficiency of feed lots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the GHR, ghrelin, leptin, NPY and UCP2 genes, and in particular for any of the SNPs described herein, wherein the kits may comprise at least one oligonucleotide selectively hybridizing to a nucleic acid comprising any one of the one or more of which are GHR, ghrelin, leptin, NPY and UCP2 sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the GHR, ghrelin, leptin, NPY and UCP2 sequences described herein.

Another embodiment of the invention is an oligonucleotide that specifically hybridizes under high stringency conditions to any one of the polymorphic sites of the GHR, ghrelin, leptin, NPY and UCP2 genes, wherein the oligonucleotide is between about 18 nucleotides and about 50 nucleotides.

In another embodiment of the invention, the oligonucleotide comprises a central nucleotide specifically hybridizing with a GHR, ghrelin, leptin, NPY or UCP2 gene polymorphic site of the portion of the nucleic acid molecule.

Another aspect of the invention is a method of identifying a GHR, ghrelin, leptin, NPY or UCP2 polymorphism in a nucleic acid sample comprising isolating a nucleic acid molecule encoding GHR, ghrelin, leptin, NPY or UCP2 or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by a polymorphism in any one of the GHR, ghrelin, leptin, NPY or UCP2 genes.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the GHR, ghrelin, leptin, NPY or UCP2 gene or a portion thereof that contains the polymorphism. In other embodiments of the invention, the amplification may include the step of selecting a forward and a reverse sequence primer capable of amplifying a region of the GHR, ghrelin, leptin, NPY or UCP2 gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising a GHR, ghrelin, leptin, NPY or UCP2 genotype of an animal, (b) correlating a growth, feed intake, efficiency or carcass merit quality predicted by the GHR, ghrelin, leptin, NPY or UCP2 genotype using the processor and the data storage system and (c) outputting to the output device the meat quality correlated to the GHR, ghrelin, leptin, NPY or UCP2 genotype, thereby predicting which livestock animals possess a particular growth, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

Growth Hormone Receptor SNPs

This Example illustrates associations between a single nucleotide polymorphism (SNP) in the growth hormone receptor (GHR gene) with economically relevant measures of feed intake, growth, and carcass quality in beef cattle. The SNP is a specific A to G mutation at the 300 nucleotide position in intron 4 of the bovine GHR gene.

The GHR gene is bound by the GH gene in a homodimeric constellation resulting in the initiation of signal transduction mechanisms and the subsequent activation of many hormonal systems in the regulation of growth promotion lipid, nitrogen, mineral and carbohydrate metabolism and includes effects on protein synthesis, protein degradation, and regulation of protein and nitrogen retention fat synthesis, increase fatty acid oxidation, stimulate fatty acid mobilization from body adipose tissues. Treatment of animals, especially ruminant livestock, with growth hormone results in decreased feed intake, increased average daily gain, increased feed efficiency, decreased fat accretion and increased protein accretion.

The experimental animals used in this study were Continental×British hybrid beef steers sired by Angus, Charolais or University of Alberta Hybrid bulls. Feed intake, growth and carcass data were collected over two years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

The SNP analyzed is an A to G nucleotide substitution at the 300 nucleotide position in intron 4 of the GHR gene (Accession No. AY643807), which has the nucleotide sequence shown in FIG. 1 (SEQ ID NO: 1).

Associations of the genotypes for each polymorphism with measures of performance and carcass merit were analyzed using General Linear Mixed Model in SAS. The statistical analyses model included fixed effects of SNP genotype, test year (two levels), contemporary test group nested within year (four levels), breed of sire (three levels), linear covariate of age of animal on test, and random effects of sire and dam of animal. Additive and non-additive genetic effects were estimated for traits that were or tended to be significant ($P<0.10$) between different SNP genotypes.

TABLE 1

Genotype and allele frequencies of the GHR SNP in the experimental population of beef cattle.

| Sire breed | Number of Animals | AA | AG | GG | G allele frequency |
|---|---|---|---|---|---|
| Angus | 127 | 86 | 38 | 3 | 0.17 |
| Charolais | 92 | 43 | 43 | 6 | 0.30 |
| Hybrid | 85 | 51 | 28 | 6 | 0.24 |
| Total | 304 | 181 | 109 | 15 | 0.23 |

TABLE 2

Effect of growth hormone receptor genotypes on performance and carcass merit of beef steers

| Trait | GHR SNP genotype | | | P value[a] |
|---|---|---|---|---|
| | AA | AG | GG | |
| Number of animals | 180 | 109 | 15 | |
| Average daily gain, kg/d | 1.47 ± 0.03 | 1.41 ± 0.03 | 1.65 ± 0.07 | 0.004 |
| Final weight, kg | 459.42 ± 6.25 | 450.50 ± 6.66 | 489.30 ± 11.96 | 0.006 |
| Dry matter intake, kg/d | 9.36 ± 0.16 | 9.25 ± 0.17 | 10.30 ± 0.33 | 0.01 |
| Metabolic mid-weight, $kg^{.75}$ | 92.60 ± 0.97 | 91.32 ± 1.03 | 96.60 ± 1.84 | 0.01 |
| Slaughter weight, kg | 523.82 ± 7.10 | 518.75 ± 7.57 | 557.63 ± 13.60 | 0.02 |
| LM area, $cm^2$ | 81.41 ± 0.98 | 80.95 ± 1.08 | 87.18 ± 2.31 | 0.03 |
| Ultrasound LM area, $cm^2$ | 77.23 ± 0.60 | 76.63 ± 0.70 | 81.42 ± 1.81 | 0.06 |
| Feed conversion ratio, kg DM/kg of gain | 6.63 ± 0.08 | 6.88 ± 0.10 | 6.43 ± 0.26 | 0.08 |
| Ultrasound marbling score | 5.00 ± 0.07 | 4.97 ± 0.08 | 5.29 ± 0.17 | 0.20 |

[a]P values from overall F test.

TABLE 3

Additive and non-additive genetic effects of GHR SNP on performance and carcass merit

| Trait | Additive Effect | P value | Dominance deviation | P value |
|---|---|---|---|---|
| Average daily gain, kg/d | −0.18 ± 0.07 | 0.02 | 0.15 ± 0.04 | 0.001 |
| Final weight, kg | −29.88 ± 11.26 | 0.01 | 23.86 ± 6.64 | 0.002 |
| Dry matter intake, kg/d | −0.94 ± 0.32 | 0.01 | 0.58 ± 0.19 | 0.006 |
| Metabolic mid-weight, $kg^{.75}$ | −4.00 ± 1.72 | 0.03 | 3.28 ± 1.02 | 0.004 |
| Slaughter weight, kg | −33.81 ± 12.81 | 0.02 | 21.97 ± 7.57 | 0.008 |
| LM area, $cm^2$ | −5.77 ± 2.33 | 0.03 | 3.35 ± 1.37 | 0.03 |
| Ultrasound LM area, $cm^2$ | −4.19 ± 1.89 | 0.04 | 2.69 ± 1.12 | 0.03 |

TABLE 3-continued

Additive and non-additive genetic effects of GHR SNP on performance and carcass merit

| Trait | Additive Effect | P value | Dominance deviation | P value |
|---|---|---|---|---|
| Feed conversion ratio, kg of DM/kg of gain | 0.20 ± 0.27 | 0.47 | −0.35 ± 0.16 | 0.04 |
| Ultrasound marbling score | −0.29 ± 0.17 | 0.11 | 0.17 ± 0.10 | 0.10 |
| Feeding duration, min/d | −5.61 ± 3.44 | 0.12 | 3.48 ± 2.02 | 0.10 |
| Carcass weight, kg | −14.15 ± 9.06 | 0.15 | 8.44 ± 5.31 | 0.14 |

Example 2

Leptin SNPs

This Example illustrates associations between two single nucleotide polymorphisms (SNPs) in the bovine leptin gene exon 3 and promoter with measures of feed intake, growth and carcass quality in beef cattle. These two SNPs, UASMS2 (C-T mutation at position 528 in AB070368) and A59V (C-T mutation at position 321 in BTA512639) in the bovine leptin gene, and their haplotypes, show strong associations with serum leptin concentration and economically relevant traits of growth, feed intake, efficiency and carcass merit in cattle.

Leptin is an adipocyte-derived 16-kDa cytokine-like hormone product of the obese gene (Zhang et al., 1994; Ji et al., 1998) that circulates in the serum in the free and bound forms. Leptin's role as a lipostatic signal regulating whole body energy metabolism through interactions with the leptin receptor in the hypothalamus makes it one of the best physiological markers for the regulation of BW, feed intake, energy expenditure, body fatness, milk yield and composition, and overall carcass quality.

The experimental animals used in this study were Continental×British hybrid beef steers sired by Angus, Charolais or University of Alberta Hybrid bulls. Feed intake, growth and carcass data were collected over three years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

Two SNP and their genotype combinations were analyzed in this report. The first mutation, UASMS2, is a C-T substitution located at nucleotide position 528 in the bovine leptin promoter (GenBank accession no. AB070368). The nucleotide sequence is depicted in FIG. 2 (SEQ ID NO: 2).

The second mutation, is a C-T substitution at position 321 (GenBank accession no. BTA512639; EMBL Accession no. AJ512639) that results in an alanine (A; GCG) to valine (V; GTG) at amino acid 59 in the β-helix region of the leptin molecule that is conserved between species. The nucleotide sequence is depicted in FIG. 3 (SEQ ID NO: 3).

Association of the polymorphisms ot their haplotypes with measures of performance and carcass merit were analyzed using a General Linear Mixed Model in SAS. The statistical analyses model included fixed effects of SNP genotype, test year (three levels), contemporary test group nested within year (six levels), breed of sire (three levels), linear covariate of age of animal on test, and random effects of sire and dam of animal.

Results of these analyses are shown in the following tables.

TABLE 4

Association of UASMS2 SNP in the leptin promoter (LS means ± SE) with measures of serum leptin concentration, performance, feed efficiency, ultrasound, and carcass merit in composite crossbred cattle (n = 464)

| Trait | UASMS2 SNP genotype | | | P value[a] |
|---|---|---|---|---|
| | CC | CT | TT | |
| Number of animals | 306 | 146 | 12 | |
| Serum leptin level, ng/mL | 13.04 ± 0.38[c] | 13.94 ± 0.54[c] | 19.20 ± 1.53[b] | <0.001 |
| Phenotypic RFI, kg/d | −0.07 ± 0.07[c] | 0.16 ± 0.09[b] | 0.13 ± 0.26[b] | 0.09 |
| Genetic RFI, kg/d | −0.21 ± 0.07[c] | 0.01 ± 0.09[b] | 0.04 ± 0.26[b] | 0.10 |
| Feed conversion, kg DM/kg gain | 7.21 ± 0.11 | 7.37 ± 0.14 | 7.22 ± 0.33 | 0.47 |
| Dry matter intake, kg/d | 10.33 ± 0.13[c] | 10.71 ± 0.17[bc] | 11.09 ± 0.42[b] | 0.036 |
| Average daily gain, kg/d | 1.47 ± 0.03 | 1.45 ± 0.03 | 1.53 ± 0.08 | 0.52 |
| Metabolic BW, $kg^{0.75}$ | 90.65 ± 0.68 | 90.96 ± 0.83 | 92.58 ± 1.84 | 0.56 |
| Backfat gain, mm/d ($\times 10^{-2}$) | 3.40 ± 0.10[c] | 3.33 ± 0.10[c] | 4.60 ± 0.40[b] | 0.017 |
| Marbling gain, units/d ($\times 10^{-2}$) | 0.70 ± 0.02[c] | 0.70 ± 0.04[c] | 1.00 ± 0.10[b] | 0.05 |
| Ultrasound backfat, mm | 8.93 ± 0.20[d] | 9.09 ± 0.28[c] | 11.38 ± 0.83[b] | 0.017 |
| Ultrasound marbling score | 5.07 ± 0.06[c] | 5.22 ± 0.08[b] | 5.58 ± 0.20[b] | 0.023 |
| Ultrasound LM area, $cm^2$ | 83.61 ± 0.56 | 83.83 ± 0.80 | 80.73 ± 2.29 | 0.42 |
| Number of animals | 255 | 118 | 8 | |
| Carcass grade fat, mm | 10.32 ± 0.30[c] | 10.58 ± 0.44[c] | 13.37 ± 1.36[b] | 0.09 |
| Average carcass backfat, mm | 11.82 ± 0.29[c] | 12.13 ± 0.43[c] | 14.82 ± 1.36[b] | 0.09 |
| LM area | 84.18 ± 0.72 | 83.71 ± 0.98 | 82.86 ± 2.75 | 0.83 |
| Carcass marbling score | 2.47 ± 0.04 | 2.54 ± 0.06 | 2.65 ± 0.17 | 0.35 |
| Lean meat yield | 58.17 ± 0.17 | 57.98 ± 0.44 | 55.88 ± 1.26 | 0.17 |

[a]P value from overall F test
[b,c,d]Means in rows followed by different superscripts are different (P < 0.05).

TABLE 5

Association of A59V SNP in leptin exon 3 (LS means ± SE) with measures of serum leptin concentration, performance, feed efficiency, feeding behaviour, and carcass merit in composite crossbred cattle.

| Trait | A59V SNP genotypes | | | P value[a] |
|---|---|---|---|---|
| | CC | CT | TT | |
| Number of animals | 31 | 174 | 259 | |
| Serum leptin level, ng/mL | 10.80 ± 0.98[d] | 13.40 ± 0.40[c] | 14.43 ± 0.37[b] | 0.0029 |
| Phenotypic RFI, kg/d | 0.03 ± 0.16 | −0.02 ± 0.07 | −0.06 ± 0.06 | 0.79 |
| Genetic RFI, kg/d | −0.04 ± 0.06 | −0.16 ± 0.06 | −0.22 ± 0.06 | 0.59 |
| Dry matter intake, kg/d | 10.33 ± 0.25 | 10.53 ± 0.14 | 10.55 ± 0.14 | 0.70 |
| Average daily gain, kg/d | 1.36 ± 0.05[c] | 1.48 ± 0.03[b] | 1.50 ± 0.03[b] | 0.039 |
| Metabolic BW, $kg^{0.75}$ | 91.28 ± 1.31 | 91.35 ± 0.84 | 91.11 ± 0.83 | 0.93 |
| Feed conversion, kg DM/kg gain | 7.96 ± 0.23[b] | 7.26 ± 0.12[c] | 7.20 ± 0.12[c] | 0.005 |
| Partial efficiency of growth | 0.27 ± 0.009[d] | 0.29 ± 0.004[c] | 0.30 ± 0.003[b] | 0.06 |
| Relative growth rate ($\times 10^{-2}$) | 14.8 ± 0.59[c] | 16.23 ± 0.25[b] | 16.44 ± 0.24[b] | 0.013 |
| Kleiber ratio, ($\times 10^{-2}$) | 1.48 ± 0.05[c] | 1.62 ± 0.03[b] | 1.72 ± 0.02[b] | 0.013 |
| Ultrasound backfat, mm | 7.93 ± 0.55[d] | 8.74 ± 0.23[c] | 9.46 ± 0.21[b] | 0.014 |
| Ultrasound LM area, $cm^2$ | 82.20 ± 1.42[c] | 84.55 ± 0.61[b] | 83.24 ± 0.57[bc] | 0.011 |
| Number of Animals | 26 | 143 | 212 | |
| Carcass grade fat, mm | 9.52 ± 0.79 | 10.15 ± 0.36 | 10.94 ± 0.33 | 0.10 |
| Average carcass backfat, mm | 10.63 ± 0.78[d] | 11.64 ± 0.34[c] | 12.55 ± 0.30[b] | 0.039 |
| Carcass LM area, $cm^2$ | 84.40 ± 1.64[bc] | 85.56 ± 0.81[b] | 83.83 ± 0.75[c] | 0.015 |
| Carcass marbling score | 2.45 ± 0.10 | 2.44 ± 0.05 | 2.51 ± 0.05 | 0.47 |
| Lean meat yield | 59.13 ± 0.74[b] | 58.56 ± 0.34[bc] | 57.47 ± 0.31[c] | 0.024 |
| Carcass yield grade | 1.67 ± 0.14 | 1.59 ± 0.06 | 1.76 ± 0.06 | 0.10 |

[a]P value from overall F test
[b,c,d]Means in rows followed by different superscripts are different (P < 0.05).

TABLE 6

Association of UASMS2 and A59V genotype combinations with serum leptin concentration, performance, feed efficiency, ultrasound, and carcass merit in crossbred composite cattle.

| Trait[a] | UASMS2 and A59V haplotype | | | | | | SEM | Effect[b], % | P value[b] |
|---|---|---|---|---|---|---|---|---|---|
| | CCCC | CCCT | CCTT | CTCT | CTTT | TTTT | | | |
| Animals | 31 | 127 | 148 | 47 | 99 | 12 | — | — | — |
| SLPT | 10.37[e] | 12.91[de] | 14.10[d] | 14.01[d] | 14.11[d] | 19.39[c] | 0.80 | 8.97 | <0.001 |
| RFIp | 0.02 | −0.04 | −0.16 | 0.06 | 0.07 | 0.11 | 0.13 | 0.13 | 0.44 |
| RFIg | −0.06 | −0.19 | −0.31 | −0.09 | −0.07 | −0.06 | 0.13 | 0.03 | 0.69 |
| DMI | 10.32 | 10.47 | 10.48 | 10.70 | 10.63 | 10.91 | 0.22 | 0.16 | 0.29 |
| ADG | 1.36[d] | 1.47[c] | 1.51[c] | 1.46[c] | 1.47[c] | 1.51[c] | 0.04 | 0.87 | 0.042 |
| MWT | 91.21 | 91.02 | 91.04 | 92.38 | 91.22 | 92.12 | 1.20 | 0.01 | 0.70 |
| FCR | 7.89[c] | 7.24[d] | 7.08[d] | 7.49[dc] | 7.42[dc] | 7.22[d] | 0.22 | 0.50 | 0.019 |
| RGR ($\times 10^{-2}$) | 14.85[d] | 16.18[cd] | 16.54[c] | 15.66[cd] | 15.85[cd] | 16.46[c] | 0.40 | 1.24 | 0.0028 |
| KRAT ($10^{-2}$) | 1.48[d] | 1.65[c] | 1.64[c] | 1.57[cd] | 1.58[cd] | 1.65[c] | 0.09 | 1.19 | 0.0053 |
| UBF | 7.82[e] | 8.55[de] | 9.42[d] | 9.16[d] | 9.07[d] | 11.38[c] | 0.43 | 6.68 | 0.005 |
| UMAR | 5.15[e] | 5.02[e] | 5.11[e] | 5.26[de] | 5.20[e] | 5.55[c] | 0.11 | 6.26 | <0.001 |
| ULMA | 82.32[d] | 84.07[cd] | 82.19[d] | 85.71[c] | 82.96[d] | 81.64[d] | 1.13 | 0.91 | 0.01 |
| Animals | 26 | 109 | 120 | 34 | 84 | 8 | — | — | — |
| CGF, mm | 9.66[e] | 9.89[de] | 10.89[d] | 10.84[d] | 10.55[d] | 13.51[c] | 0.69 | 5.53 | <0.001 |
| CBF, mm | 10.75[e] | 11.40[de] | 12.40[d] | 12.27[d] | 12.18[d] | 15.12[c] | 0.70 | 5.84 | <0.001 |
| CMAR | 2.42[e] | 2.41[e] | 2.48[de] | 2.56[cd] | 2.51[cd] | 2.72[c] | 0.09 | 4.16 | <0.001 |
| CREA | 84.33[cd] | 85.16[cd] | 82.60[d] | 86.09[c] | 82.86[d] | 83.70[d] | 1.42 | 4.85 | <0.001 |
| CYG | 1.67 | 1.57 | 1.74 | 1.72 | 1.65 | 2.04 | 0.12 | 4.20 | <0.001 |
| LMY | 59.07[c] | 58.70[cd] | 57.53[d] | 58.08[cd] | 57.80[d] | 55.59[e] | 0.65 | 8.92 | <0.001 |

[a]SLPT = serum leptin concentration (ng/mL); RFIp = phenotypic RFI (kg/d); RFIg = genetic RFI (kg/d); DMI = daily dry matter intake ((kg/d); MWT = metabolic BW ($kg^{0.75}$); ADG = average daily gain (kg/d); FCR = feed conversion ratio (kg DM/kg gain); RGR = relative growth rate; KRAT = Kleiber ratio; UBF = ultrasound backfat (mm); UMAR = ultrasound marbling score; ULMA = ultrasound LM area ($cm^2$); CGF = carcass grade fat (mm); CBF = carcass backfat (mm); CMAR = carcass marbling; CLMA = carcass LM area ($cm^2$); CYG = carcass yield grade; LMY = lean meat yield (%).
[b]P values and haplotype effects are from haplotype regression using dummy variables. Haplotype effects are expressed as % of total phenotypic variation in the trait. shown.
[c,d,e]Means in rows followed by different superscripts are different (P < 0.05).

Example 3

Ghrelin SNPs

This Example illustrates associations between a single nucleotide polymorphism (SNP) in the ghrelin gene with measures of feed intake, growth, and carcass quality in beef cattle. The SNP is a specific A to G nucleotide substitution in intron 3 of the bovine ghrelin gene.

Ghrelin is a growth hormone releasing peptide, consisting of 28-amino acids, which serves as an endogenous ligand for growth hormone-secretagogue receptors (GHS-R), which are G-protein-coupled receptors. These receptors in turn stimulate the release of GH from the pituitary gland. In addition to the role of ghrelin in the stimulation of the release of GH, ghrelin also plays a role in the stimulation of appetite and feeding activity through interactions with peptides such as NPY.

The experimental animals used in this study were Continental×British hybrid beef steers sired by Angus, Charolais or University of Alberta Hybrid bulls. Feed intake, growth and carcass data were collected over two years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

The SNP analyzed is an A to G nucleotide substitution in intron 3 of the bovine ghrelin gene (unpublished) and has the sequence is depicted in FIG. 4.

Associations of the genotypes for each polymorphism with measures of performance and carcass merit were analyzed using General Linear Mixed Model in SAS. The statistical analyses model included fixed effects of SNP genotype, test year (two levels), contemporary test group nested within year (four levels), breed of sire (three levels), linear covariate of age of animal on test, and random effects of sire and dam of animal. Additive genetic effects were estimated for traits that were or tended to be statistically different (P<0.10) between different SNP genotypes.

TABLE 7

Genotype and allele frequencies of the Ghrelin SNP in the experimental population of beef cattle.

| Sire breed | Number of Animals | AA | AG | GG | G allele frequency |
|---|---|---|---|---|---|
| Angus | 127 | 97 | 27 | 3 | 0.13 |
| Charolais | 92 | 77 | 14 | 1 | 0.09 |
| Hybrid | 85 | 74 | 11 | — | 0.06 |
| Total | 304 | 248 | 52 | 4 | 0.10 |

TABLE 8

Effect of ghrelin genotypes on performance and carcass merit of beef steers.

| Trait | Ghrelin SNP genotype AA | Ghrelin SNP genotype AG | P value[a] |
|---|---|---|---|
| Number of animals | 248 | 52 | |
| Carcass weight, kg | 311.10 ± 4.38 | 298.94 ± 5.90 | 0.04 |
| Slaughter weight, kg | 527.08 ± 7.14 | 511.78 ± 9.32 | 0.05 |
| Lean Meat Yield, % | 57.86 ± 0.45 | 59.10 ± 0.65 | 0.06 |
| Yield grade | 1.60 ± 0.07 | 1.35 ± 0.12 | 0.06 |
| Average daily gain, kg/d | 1.47 ± 0.03 | 1.39 ± 0.04 | 0.08 |
| Final weight, kg | 460.37 ± 6.15 | 448.16 ± 8.11 | 0.08 |
| Metabolic mid-weight, $kg^{.75}$ | 92.76 ± 0.96 | 91.03 ± 1.25 | 0.1 |
| Dry matter intake, kg/d | 9.42 ± 0.15 | 9.16 ± 0.21 | 0.18 |

[a]P values from overall F test. Four animals with genotype GG were excluded from the analyses of ghrelin.

Example 4

Neuropeptide Y SNPs

This Example illustrates associations between a single nucleotide polymorphism (SNP) in the neuropeptide Y (NPY) gene with measures of growth and carcass quality in beef cattle. The SNP is a specific A to G mutation at the 666 nucleotide position in intron 2 of the bovine NPY gene.

Neuropeptide Y (NPY) is a 36-amino acid peptide that plays a powerful role as a central appetite stimulator in the regulation and control of food intake and energy-balance. Neuropeptide Y also stimulates food intake and induces a general anabolic state by reducing energy expenditure. Additionally, NPY influences the regulation of growth in animals by causing a dose-dependent inhibition of GH release, and a lowering of plasma growth hormone and IGF-1 concentration through the stimulation of somatostatin.

The experimental animals used in this study were Continental×British hybrid beef steers sired by Angus, Charolais or University of Alberta Hybrid bulls. Feed intake, growth and carcass data were collected over two years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

The SNP analyzed is an A to G substitution at the 666 nucleotide position in intron 2 of the NPY gene (Accession No. AY491054). The nucleotide sequence is depicted in FIG. 5 (SEQ ID NO: 5. (species, *bos taurus*):

Associations of the genotypes for each polymorphism with measures of performance and carcass merit were analyzed using General Linear Mixed Model in SAS. The statistical analyses model included fixed effects of SNP genotype, test year (two levels), contemporary test group nested within year (four levels), breed of sire (three levels), linear covariate of age of animal on test, and random effects of sire and dam of animal. Additive and non-additive genetic effects were estimated for traits that were or tended to be significant (P<0.10) between different SNP genotypes.

TABLE 9

Genotype and allele frequencies of the NPY SNP in the experimental population of beef cattle.

| Sire breed | Number of Animals | AA | AG | GG | G allele frequency |
|---|---|---|---|---|---|
| Angus | 127 | 28 | 61 | 38 | 0.54 |
| Charolais | 92 | 18 | 56 | 18 | 0.50 |
| Hybrid | 85 | 9 | 29 | 47 | 0.72 |
| Total | 304 | 55 | 146 | 103 | 0.58 |

TABLE 10

Effect of NPY genotypes on performance and carcass merit of beef steers.

| Trait | NPY SNP genotype | | | |
|---|---|---|---|---|
| | AA | AG | GG | P value[a] |
| Number of animals | 55 | 146 | 103 | |
| Ultrasound LM area, cm$^2$ | 79.20 ± 0.96 | 78.55 ± 0.61 | 75.11 ± 0.70 | 0.002 |
| Slaughter weight, kg | 540.42 ± 8.35 | 530.66 ± 6.67 | 513.25 ± 7.26 | 0.008 |
| Metabolic mid-weight, kg$^{.75}$ | 94.31 ± 1.14 | 93.40 ± 0.90 | 91.29 ± 0.99 | 0.03 |
| Final weight, kg | 469.57 ± 7.45 | 464.28 ± 5.89 | 450.65 ± 6.42 | 0.04 |
| LM area, cm$^2$ | 82.74 ± 1.37 | 82.52 ± 1.08 | 79.63 ± 1.19 | 0.06 |
| Carcass weight, kg | 314.63 ± 5.45 | 311.67 ± 4.33 | 301.19 ± 4.78 | 0.06 |

[a]P values from overall F test.

TABLE 11

Additive and non-additive genetic effects of NPY SNP on performance and carcass merit.

| Trait | Additive Effect | P value | Dominance deviation | P value |
|---|---|---|---|---|
| Ultrasound LM area, cm$^2$ | 4.09 ± 1.19 | 0.002 | −1.39 ± 0.80 | 0.10 |
| Slaughter weight, kg | 27.17 ± 8.35 | 0.004 | −3.83 ± 5.48 | 0.49 |
| Metabolic mid-weight, kg$^{.75}$ | 3.02 ± 1.17 | 0.02 | −0.60 ± 0.76 | 0.44 |
| Final weight, kg | 18.92 ± 7.57 | 0.02 | −4.17 ± 4.96 | 0.41 |
| LM area, cm$^2$ | 3.11 ± 1.45 | 0.05 | −1.34 ± 0.95 | 0.19 |
| Carcass weight, kg | 13.44 ± 5.70 | 0.04 | −3.76 ± 3.75 | 0.34 |

Example 5

Uncoupling Protein 2 SNPs

This Example illustrates associations between a single nucleotide polymorphism (SNP) in the uncoupling protein 2 (UCP2) gene with measures of feed intake, growth, and carcass quality in beef cattle. The UCP2 SNP2 polymorphism analyzed is a specific A to G substitution at the 812 nucleotide position in exon 4 of the bovine UCP2 gene (Accession No. XM_614452) and the nucleotide sequence is depicted in FIG. 6 (SEQ ID NO: 6).

The UCP2 SNP 1 polymorphism considered is a C to G substitution identified at position 213 in intron 2 of the UCP2 gene according to the following unpublished nucleotide sequence of FIG. 7 (SEQ ID NO: 7).

UCP2 has been shown to regulate insulin secretion, and it is up-regulated by a high-fat diet, suggesting UCP2 to be important for determining basal metabolic rate and possibly resistance to obesity. Significant geneic linkage has been established between microsatellite markers encompassing the location of UCP2 with resting metabolic rate, body mass, body fatness and fat mass in humans.

The experimental animals used in this study were Continental×British hybrid beef steers sired by Angus, Charolais or University of Alberta Hybrid bulls. Feed intake, growth and carcass data were collected over two years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

TABLE 12

Genotype and allele frequencies of the UCP2 SNP2 in the experimental population of beef cattle.

| Sire breed | Number of Animals | AA | AG | GG | G allele frequency |
|---|---|---|---|---|---|
| Angus | 127 | 47 | 63 | 17 | 0.38 |
| Charolais | 92 | 46 | 38 | 8 | 0.29 |
| Hybrid | 85 | 48 | 31 | 6 | 0.25 |
| Total | 304 | 141 | 132 | 31 | 0.32 |

TABLE 13

Genotype and allele frequencies of the UCP2 SNP1 in the experimental population of beef cattle.

| Sire breed | Number of Animals | CC | CG | GG | G allele frequency |
|---|---|---|---|---|---|
| Angus | 127 | 47 | 62 | 18 | 0.39 |
| Charolais | 92 | 46 | 39 | 7 | 0.29 |
| Hybrid | 85 | 48 | 30 | 7 | 0.26 |
| Total | 304 | 141 | 131 | 32 | 0.32 |

TABLE 14

Effect of UCP2 SNP1 genotypes on performance and carcass merit of beef steers.

| Trait | UCP2 SNP1 genotype | | | |
|---|---|---|---|---|
| | CC | CG | CG | P-value[a] |
| Number of animals | 141 | 131 | 32 | |
| Final weight, kg | 455.07 ± 6.91 | 463.60 ± 6.91 | 440.94 ± 9.44 | 0.02 |
| Metabolic mid-weight, kg$^{.75}$ | 91.97 ± 1.07 | 93.21 ± 1.07 | 89.79 ± 1.45 | 0.02 |
| Slaughter weight, kg | 523.39 ± 7.76 | 527.41 ± 7.76 | 506.82 ± 10.67 | 0.09 |
| Dry matter intake, kg/d | 9.37 ± 0.17 | 9.44 ± 0.17 | 8.94 ± 0.25 | 0.11 |
| Lean Meat Yield, % | 58.44 ± 0.46 | 57.61 ± 0.48 | 58.91 ± 0.79 | 0.13 |

TABLE 14-continued

Effect of UCP2 SNP1 genotypes on performance and carcass merit of beef steers.

| | UCP2 SNP1 genotype | | | |
|---|---|---|---|---|
| Trait | CC | CG | CG | P-value[a] |
| Average backfat | 10.90 ± 0.36 | 11.88 ± 0.39 | 10.94 ± 0.81 | 0.18 |
| Average daily gain, kg/d | 1.44 ± 0.03 | 1.48 ± 0.03 | 1.40 ± 0.05 | 0.19 |
| Carcass weight, kg | 307.47 ± 4.86 | 311.92 ± 5.01 | 300.12 ± 7.33 | 0.20 |

[a] P values from overall F test.

TABLE 15

Additive and non-additive genetic effects of UCP2 SNP1 on performance and carcass merit

| Trait | Additive Effect | P value | Dominance deviation | P value |
|---|---|---|---|---|
| Final weight, kg | 14.13 ± 8.04 | 0.09 | −15.60 ± 5.17 | 0.01 |
| Metabolic mid-weight, kg[.75] | 2.18 ± 1.22 | 0.09 | −2.32 ± 0.79 | 0.01 |
| Slaughter weight, kg | 16.57 ± 9.15 | 0.08 | −12.31 ± 5.89 | 0.05 |
| Dry matter intake, kg/d | 0.43 ± 0.23 | 0.08 | −0.29 ± 0.15 | 0.07 |
| Lean Meat Yield, % | −0.47 ± 0.78 | 0.56 | 1.07 ± 0.49 | 0.05 |
| Average backfat | −0.05 ± 0.87 | 0.96 | −0.97 ± 0.56 | 0.11 |
| Average daily gain, kg/d | 0.05 ± 0.05 | 0.35 | −0.06 ± 0.03 | 0.07 |
| Carcass weight, kg | 7.34 ± 6.62 | 0.29 | −8.13 ± 4.17 | 0.08 |

TABLE 16

Effect of UCP2 SNP2 genotypes on performance and carcass merit of beef steers.

| | UCP2 SNP2 genotype | | | |
|---|---|---|---|---|
| Trait | AA | AG | GG | P value[a] |
| Number of animals | 141 | 132 | 31 | |
| Final weight, kg | 455.22 ± 6.80 | 463.76 ± 6.80 | 441.66 ± 9.44 | 0.02 |
| Metabolic mid-weight, kg[.75] | 92.01 ± 1.05 | 93.24 ± 1.05 | 89.92 ± 1.45 | 0.03 |
| Dry matter intake, kg/d | 9.37 ± 0.17 | 9.46 ± 0.17 | 8.91 ± 0.25 | 0.07 |
| Slaughter weight, kg | 523.52 ± 7.67 | 527.54 ± 7.67 | 507.56 ± 10.70 | 0.11 |
| Lean Meat Yield, % | 58.43 ± 0.47 | 57.59 ± 0.49 | 58.82 ± 0.79 | 0.14 |
| Average daily gain, kg/d | 1.44 ± 0.03 | 1.48 ± 0.03 | 1.39 ± 0.05 | 0.18 |
| Carcass weight, kg | 307.49 ± 4.82 | 311.89 ± 4.97 | 301.27 ± 7.29 | 0.25 |

[a] P values from overall F test.

TABLE 17

Additive and non-additive genetic effects of UCP2 SNP2 on performance and carcass merit.

| Trait | Additive Effect | P value | Dominance deviation | P value |
|---|---|---|---|---|
| Final weight, kg | 13.56 ± 8.10 | 0.11 | −15.31 ± 5.20 | 0.01 |
| Metabolic mid-weight, kg[.75] | 2.08 ± 1.23 | 0.10 | −2.28 ± 0.79 | 0.01 |
| Dry matter intake, kg/d | 0.47 ± 0.23 | 0.06 | −0.32 ± 0.15 | 0.05 |
| Slaughter weight, kg | 15.96 ± 9.22 | 0.10 | −12.00 ± 5.94 | 0.06 |
| Lean Meat Yield, % | −0.39 ± 0.77 | 0.63 | 1.03 ± 0.48 | 0.06 |
| Average daily gain, kg/d | 0.05 ± 0.05 | 0.32 | −0.06 ± 0.03 | 0.07 |
| Carcass weight, kg | 6.22 ± 6.60 | 0.37 | −7.51 ± 4.17 | 0.10 |

Example 6

This Example illustrates that there are associations between SNPs and measures of performance and carcass merit in beef cattle. In addition, the additive genetic effect and the dominance deviation of the genotypes was determined. The additive effect is the difference in trait value between the two homozygote genotypes ($\phi AA-\phi GG$). The dominance genotypic value is the deviation of the heterozygote from the mean of the two homozygotes ($\phi AG-(\phi AA+GG)/2$).

The experimental animals used in this study were derived from a hybrid dam line crossed to Angus, Charolais and hybrid sires. The phenotypic data was collected using a GrowSafe system. SNP genotyping was done using an illumina Beadstation. The SNP genotypes examined in this study were growth hormone receptor (GHR), neuropeptide Y (NPY), Ghrelin, and uncoupling protein-2 (UCP2).

Association analysis was conducted in PROC MIXED of SAS with the following variables: (1) fixed effects: SNP genotype, sire breed (three levels), batch nested in year (four levels); (2) random effects: Sire and Dam identification; (3) linear covariate: age at start of test (not used for NPY association).

TABLE 18

Associations of SNP genotypes with performance and carcass merit of beef steers.

| Trait | Gene | AA | AG | GG | P-value |
|---|---|---|---|---|---|
| Average daily gain, kg/d | GHR | 1.47 | 1.41 | 1.65 | .004 |
| | Ghrelin | 1.47 | 1.39 | | .08 |
| Dry matter intake, kg/d | GHR | 9.4 | 9.3 | 10.3 | .01 |
| | UCP2 | 9.4 | 9.5 | 8.9 | .07 |
| Carcass LM area, cm[2] | GHR | 81 | 81 | 87 | .03 |
| | NPY | 83 | 83 | 80 | .06 |
| Ultrasound LM area, cm[2] | GHR | 77 | 77 | 81 | .06 |
| | NPY | 79 | 79 | 75 | .002 |
| Lean Meat Yield, % | Ghrelin | 57.9 | 59.1 | | .06 |
| Metabolic mid-weight, kg[.75] | UCP2 | 91.9 | 93.2 | 89.8 | .02 |
| | NPY | 94.3 | 93.4 | 91.3 | .03 |
| | GHR | 91.3 | 91.3 | 96.6 | .01 |
| | Ghrelin | 91.0 | 91.0 | | .1 |

TABLE 19

Additive effect and dominance deviation of the SNP genotypes (effect ± SE)

| Trait | Gene | Additive Effect | Dominance Deviation |
|---|---|---|---|
| Average daily gain, kg/d | GHR | 0.18 ± 0.07* | 0.15 ± 0.04*** |
| Carcass LM area, cm$^2$ | GHR | 5.8 ± 2.3* | 3.4 ± 1.4* |
| Ultrasound LM area, cm$^2$ | GHR | 4.2 ± 1.9* | 2.7 ± 1.1* |
| | NPY | 4.1 ± 1.2** | −1.4 ± 0.8 |
| Dry matter intake, kg/d | GHR | 0.9 ± 0.3** | 0.6 ± 0.2** |
| | UCP2 | 0.5 ± 0.2 | −0.3 ± 0.2* |
| Final weight, kg | GHR | 30 ± 11** | 24 ± 7** |
| | NPY | 19 ± 7.5* | −4 ± 5 |
| | UCP2 | 14 ± 8 | −15 ± 5* |
| Metabolic mid-weight, kg$^{.75}$ | UCP2 | 2.2 ± 1.22 | −2.3 ± 0.79* |
| | NPY | 3.0 ± 1.17* | −0.6 ± 0.76 |
| | GHR | 4.0 ± 1.72* | 3.3 ± 1.02** |

*P < 0.05,
**P < 0.01,
***P < 0.001 denotes the significance of the effect

TABLE 20

Allele frequency for each gene.

| | Frequency of Alleles | |
|---|---|---|
| Gene | A | G |
| GHR | 0.77 | 0.23 |
| NPY | 0.42 | 0.58 |
| UCP2 | 0.68 | 0.32 |
| Ghrelin | 0.9 | 0.1 |

FIG. 8 and tables 18-20 demonstrate that the SNP in the GHR gene is associated with body weight, average daily gain, feed intake, and LM area, and has a significant dominance deviation of the A allele over the G allele. In addition, the data show that the NPY gene is associated with body weight and LM area and there is a significant positive additive effect of the AA genotype on these traits. Moreover, the SNP in the UCP2 gene is associated with body weight and shows overdominance of the heterozygotes. It is also demonstrated that the SNP in the Ghrelin gene shows associations with body weight and average daily gain.

Example 9

TABLE 21

Summary of SNPs and Phenotypic Effect in Beef Cattle

| | SNP | Effected Carcass Trait |
|---|---|---|
| 1 | GHR-INT4 | REA, QUALITY, CHOICEQG, CALCYG CUTT, MBS, REAHCW, YG |
| 2 | UASMS1 | COST, FRAME, PREDYG, CARCFAT, HCW, INWT, BFAT, CALCWT, REA, WT3, CALCYG, CUTT, BFATRATE, MBS, DOF |
| 3 | UASMS2 | INWT, COST, HCW, ADJRTR, FRAME, CALCWT, WT3, DP |
| 4 | UCP2-INT2 | HCWVALUE, QUALITY, MBS, CHOICEQG |
| 5 | GHREL | YG, CALCYG, CUTT, PREDYG, CARCFAT, REA, BFAT |

TABLE 21-continued

Summary of SNPs and Phenotypic Effect in Beef Cattle

| | SNP | Effected Carcass Trait |
|---|---|---|
| 6 | NPY-INT2 | REA, QUALITY, CHOICEQG, CALCYG, CUTT, MBS, REAHCW, YG |

Key:
ADJRTR = Adjusted Rate of Return to Rancher
BFAT = Back Fat
BFATRATE = Rate of Deposition of Back Fat
CALCWT = Calculated Weight
CALCYG = Calculated Yield Grade
CARCFAT = Carcass Fat
CHOICEQG = % Choice as Measured by Quality Grade
CUTT = Cutability
COST = Cost of gain
DOF = Days on Feed
DP = Dressing Percentage
FRAME = Frame Score
HCW = Hot Carcass Weight
HCWVALUE = Hot Carcass Weight Value
REA = Rib Eye Area
INWT = In Weight (weight of animal on arrival at the feedyard_
MBS = Marbling Score
QUALITY = Quality Grade
PREDYG = Predicted Yield Grade
QUALITY = Quality
REA = Rib eye area
REAHCW = Rib eye area per 100 lbs of hot carcass weight
WT3 = Live weight at third weighing period
YG = Yield Grade

TABLE 22

Frequencies

| MARKERS | A252T | COUNTS | GENOT_FREQ | ALLELE_FREQ |
|---|---|---|---|---|
| A252T | AA | 1367 | 0.90 | 0.95 |
| A252T | AT | 131 | 0.09 | |
| A252T | TT | 15 | 0.01 | 0.05 |
| C963T | CC | 516 | 0.33 | 0.57 |
| C963T | CT | 757 | 0.48 | |
| C963T | TT | 306 | 0.19 | 0.43 |
| A1457G | AA | 475 | 0.30 | 0.55 |
| A1457G | AG | 760 | 0.49 | |
| A1457G | GG | 326 | 0.21 | 0.45 |
| FABP4 | CC | 871 | 0.55 | 0.74 |
| FABP4 | CG | 579 | 0.37 | |
| FABP4 | GG | 121 | 0.08 | 0.26 |
| UASMS1 | CC | 301 | 0.19 | 0.43 |
| UASMS1 | CT | 764 | 0.48 | |
| UASMS1 | TT | 512 | 0.32 | 0.57 |
| UASMS2 | CC | 778 | 0.49 | 0.70 |
| UASMS2 | CT | 662 | 0.42 | |
| UASMS2 | TT | 141 | 0.09 | 0.30 |
| EXON2FB | CC | 510 | 0.32 | 0.57 |
| EXON2FB | CT | 767 | 0.49 | |
| EXON2FB | TT | 293 | 0.19 | 0.43 |
| GHR | AA | 19 | 0.01 | 0.11 |
| GHR | AT | 304 | 0.19 | |
| GHR | TT | 1245 | 0.79 | 0.89 |
| T945M | CC | 1391 | 0.88 | 0.94 |
| T945M | CT | 181 | 0.11 | |
| T945M | TT | 8 | 0.01 | 0.06 |
| TFAM1 | CC | 483 | 0.31 | 0.55 |
| TFAM1 | CT | 729 | 0.47 | |
| TFAM1 | TT | 334 | 0.22 | 0.45 |
| TFAM2 | AA | 587 | 0.37 | 0.60 |
| TFAM2 | AC | 738 | 0.47 | |
| TFAM2 | CC | 257 | 0.16 | 0.40 |
| TFAM3 | CC | 486 | 0.33 | 0.57 |
| TFAM3 | CT | 696 | 0.47 | |
| TFAM3 | TT | 287 | 0.20 | 0.43 |

TABLE 22-continued

| | | Frequencies | | |
|---|---|---|---|---|
| MARKERS | A252T | COUNTS | GENOT_FREQ | ALLELE_FREQ |
| A59V | CC | 1161 | 0.74 | 0.86 |
| A59V | CT | 388 | 0.25 | |
| A59V | TT | 29 | 0.02 | 0.14 |
| UCP2INT2 | CC | 86 | 0.05 | 0.23 |
| UCP2INT2 | CG | 541 | 0.34 | |
| UCP2INT2 | GG | 950 | 0.60 | 0.77 |

TABLE 23

Traits, markers, allelic substitutions and effects

| Trait | Marker | Allele Substitution | | | | Fixed Effect | Additive | | | Dominance | | |
|---|---|---|---|---|---|---|---|---|---|---|---|---|
| Trait | Marker | Estimate | StdErr | DF | P-value | ProbF | Estimate | StdErr | P-value | Estimate | StdErr | P-value |
| REA | A59V | −0.454 | 0.080 | 1530 | 1.59E−08 | 1.16E−07 | −0.449 | 0.145 | 0.0020 | 0.006 | 0.165 | 0.971 |
| CALCYG | A59V | 0.159 | 0.034 | 1522 | 3.54E−06 | 6.91E−06 | 0.239 | 0.063 | 0.0002 | 0.108 | 0.071 | 0.132 |
| CALCWT | A59V | −23.034 | 5.018 | 1530 | 4.79E−06 | 1.86E−05 | −15.924 | 9.112 | 0.0807 | 9.694 | 10.369 | 0.350 |
| CUTT | A59V | −0.361 | 0.079 | 1522 | 6.10E−06 | 1.20E−05 | −0.543 | 0.146 | 0.0002 | −0.247 | 0.166 | 0.137 |
| WT3 | A59V | −22.733 | 5.021 | 1530 | 6.44E−06 | 3.03E−05 | −17.563 | 9.119 | 0.0543 | 7.049 | 10.377 | 0.497 |
| HCW | A59V | −14.924 | 3.360 | 1530 | 9.59E−06 | 3.92E−05 | −10.638 | 6.102 | 0.0815 | 5.844 | 6.944 | 0.400 |
| YG | A59V | 0.139 | 0.032 | 1462 | 1.38E−05 | 7.55E−05 | 0.154 | 0.059 | 0.0096 | 0.020 | 0.067 | 0.762 |
| INWT | A59V | −14.813 | 3.436 | 1530 | 1.73E−05 | 8.01E−05 | −11.509 | 6.240 | 0.0653 | 4.505 | 7.101 | 0.526 |
| FRAME | A59V | −0.191 | 0.045 | 1530 | 2.12E−05 | 1.19E−04 | −0.189 | 0.082 | 0.0207 | 0.004 | 0.093 | 0.969 |
| COST | A59V | −9.482 | 2.420 | 1530 | 9.28E−05 | 4.08E−04 | −7.362 | 4.394 | 0.0941 | 2.892 | 5.001 | 0.563 |
| CARCFAT | A59V | 0.464 | 0.120 | 1522 | 1.20E−04 | 7.46E−05 | 0.845 | 0.221 | 0.0001 | 0.514 | 0.250 | 0.040 |
| PREDYG | A59V | 0.070 | 0.018 | 1522 | 1.20E−04 | 7.48E−05 | 0.127 | 0.033 | 0.0001 | 0.077 | 0.038 | 0.040 |
| BFAT | A59V | 0.028 | 0.007 | 1511 | 1.22E−04 | 7.32E−05 | 0.051 | 0.013 | 0.0001 | 0.031 | 0.015 | 0.038 |
| DOF | A59V | −0.485 | 0.131 | 1530 | 0.0002 | 0.0007 | −0.302 | 0.237 | 0.2028 | 0.250 | 0.270 | 0.355 |
| BFATRATE | A59V | 0.001 | 0.000 | 1511 | 0.0008 | 0.0032 | 0.001 | 0.000 | 0.0273 | 0.000 | 0.000 | 0.658 |
| DMI | A59V | −59.448 | 20.847 | 1530 | 0.0044 | 0.0127 | −34.578 | 37.856 | 0.3612 | 33.909 | 43.080 | 0.431 |
| REAHCW | A59V | −0.027 | 0.011 | 1530 | 0.0134 | 0.0438 | −0.033 | 0.019 | 0.0930 | −0.008 | 0.022 | 0.703 |
| ADG | A59V | −0.043 | 0.023 | 1530 | 0.0586 | 0.1416 | −0.023 | 0.041 | 0.5751 | 0.027 | 0.047 | 0.564 |
| HCWVALUE | A59V | −0.335 | 0.260 | 1530 | 0.1984 | 0.3774 | −0.121 | 0.473 | 0.7987 | 0.292 | 0.538 | 0.587 |
| ADJRTR | A59V | −5.049 | 4.544 | 1530 | 0.2666 | 0.3997 | 0.287 | 8.251 | 0.9722 | 7.277 | 9.389 | 0.438 |
| ADJNR | A59V | 4.196 | 4.259 | 1530 | 0.3247 | 0.6139 | 3.690 | 7.736 | 0.6335 | −0.691 | 8.804 | 0.937 |
| ADDCARCVAL | A59V | 1.460 | 2.030 | 1530 | 0.4721 | 0.7438 | 0.616 | 3.687 | 0.8673 | −1.151 | 4.196 | 0.784 |
| MBS | A59V | 0.338 | 0.523 | 1120 | 0.5177 | 0.5608 | −0.486 | 1.092 | 0.6566 | −1.034 | 1.203 | 0.390 |
| CHOICEMBS | A59V | −0.017 | 0.030 | 1120 | 0.5603 | 0.7682 | −0.041 | 0.063 | 0.5095 | −0.030 | 0.069 | 0.664 |
| DP | A59V | −0.035 | 0.100 | 1530 | 0.7259 | 0.9397 | −0.041 | 0.182 | 0.8209 | −0.008 | 0.207 | 0.968 |
| QUALITY | A59V | 0.001 | 0.028 | 1520 | 0.9823 | 0.5472 | −0.046 | 0.051 | 0.3665 | −0.064 | 0.058 | 0.272 |
| CHOICEQG | A59V | 0.000 | 0.025 | 1520 | 0.9857 | 0.8882 | 0.018 | 0.045 | 0.6923 | 0.025 | 0.051 | 0.627 |
| BFAT | GHRINT4 | 0.02 | 0.01 | 1451 | 0.0004 | 0.0019 | 0.02 | 0.01 | 0.0069 | 0.00 | 0.01 | 0.7621 |
| CARCFAT | GHRINT4 | 0.34 | 0.10 | 1461 | 0.0005 | 0.0024 | 0.32 | 0.12 | 0.0076 | −0.04 | 0.16 | 0.7956 |
| PREDYG | GHRINT4 | 0.05 | 0.01 | 1461 | 0.0005 | 0.0024 | 0.05 | 0.02 | 0.0076 | −0.01 | 0.02 | 0.7963 |
| CALCYG | GHRINT4 | 0.10 | 0.03 | 1461 | 0.0006 | 0.0026 | 0.09 | 0.03 | 0.0104 | −0.02 | 0.04 | 0.7005 |
| CUTT | GHRINT4 | −0.22 | 0.06 | 1461 | 0.0008 | 0.0032 | −0.20 | 0.08 | 0.0122 | 0.04 | 0.10 | 0.6907 |
| REA | GHRINT4 | −0.19 | 0.06 | 1469 | 0.0029 | 0.0090 | −0.16 | 0.08 | 0.0477 | 0.08 | 0.10 | 0.4418 |
| FRAME | GHRINT4 | −0.10 | 0.04 | 1469 | 0.0087 | 0.0273 | −0.08 | 0.04 | 0.0696 | 0.03 | 0.06 | 0.5741 |
| ADJRTR | GHRINT4 | 9.41 | 3.71 | 1469 | 0.0113 | 0.0108 | 13.69 | 4.55 | 0.0026 | 9.57 | 5.89 | 0.1041 |
| ADDCARCVAL | GHRINT4 | 3.98 | 1.66 | 1469 | 0.0167 | 0.0556 | 3.71 | 2.04 | 0.0693 | −0.61 | 2.64 | 0.8164 |
| REAHCW | GHRINT4 | −0.01 | 0.01 | 1469 | 0.0850 | 0.2261 | −0.01 | 0.01 | 0.1774 | 0.00 | 0.01 | 0.9245 |
| HCW | GHRINT4 | −4.66 | 2.74 | 1469 | 0.0892 | 0.1860 | −3.32 | 3.36 | 0.3242 | 3.00 | 4.35 | 0.4902 |
| CALCWT | GHRINT4 | −5.87 | 4.09 | 1469 | 0.1515 | 0.3502 | −5.28 | 5.02 | 0.2935 | 1.33 | 6.50 | 0.8379 |
| DMI | GHRINT4 | −21.70 | 17.02 | 1469 | 0.2026 | 0.4162 | −17.34 | 20.89 | 0.4067 | 9.74 | 27.03 | 0.7186 |
| WT3 | GHRINT4 | −5.13 | 4.10 | 1469 | 0.2110 | 0.4561 | −4.91 | 5.03 | 0.3301 | 0.51 | 6.52 | 0.9375 |
| INWT | GHRINT4 | −3.46 | 2.80 | 1469 | 0.2166 | 0.3706 | −4.81 | 3.44 | 0.1618 | −3.01 | 4.45 | 0.4984 |
| ADJNR | GHRINT4 | 4.09 | 3.47 | 1469 | 0.2390 | 0.2937 | 1.54 | 4.26 | 0.7170 | −5.69 | 5.51 | 0.3023 |
| DP | GHRINT4 | −0.08 | 0.08 | 1469 | 0.3220 | 0.2559 | 0.00 | 0.10 | 0.9663 | 0.17 | 0.13 | 0.1865 |
| DOF | GHRINT4 | −0.09 | 0.11 | 1469 | 0.4135 | 0.6287 | −0.13 | 0.13 | 0.3363 | −0.09 | 0.17 | 0.6104 |
| COST | GHRINT4 | −1.54 | 1.98 | 1469 | 0.4361 | 0.4699 | −2.88 | 2.43 | 0.2359 | −2.99 | 3.14 | 0.3418 |
| ADG | GHRINT4 | −0.01 | 0.02 | 1469 | 0.5195 | 0.4641 | 0.00 | 0.02 | 0.9297 | 0.03 | 0.03 | 0.2899 |
| YG | GHRINT4 | 0.01 | 0.03 | 1403 | 0.5933 | 0.7651 | 0.00 | 0.03 | 0.8936 | −0.02 | 0.04 | 0.6168 |
| QUALITY | GHRINT4 | −0.01 | 0.02 | 1459 | 0.6084 | 0.5434 | −0.03 | 0.03 | 0.3243 | −0.04 | 0.04 | 0.3279 |
| HCWVALUE | GHRINT4 | 0.10 | 0.21 | 1469 | 0.6313 | 0.1559 | 0.39 | 0.26 | 0.1407 | 0.63 | 0.34 | 0.0619 |
| MBS | GHRINT4 | 0.20 | 0.42 | 1067 | 0.6398 | 0.3451 | −0.23 | 0.52 | 0.6556 | −0.93 | 0.67 | 0.1672 |
| CHOICEQG | GHRINT4 | 0.01 | 0.02 | 1459 | 0.6677 | 0.8537 | 0.01 | 0.02 | 0.5752 | 0.01 | 0.03 | 0.7164 |
| BFATRATE | GHRINT4 | 0.00 | 0.00 | 1451 | 0.9190 | 0.8523 | 0.00 | 0.00 | 0.6850 | 0.00 | 0.00 | 0.5782 |
| CHOICEMBS | GHRINT4 | 0.00 | 0.02 | 1067 | 0.9829 | 0.6411 | −0.02 | 0.03 | 0.5632 | −0.04 | 0.04 | 0.3459 |
| CALCYG | A1457G | −0.065 | 0.024 | 1505 | 0.0065 | 0.0247 | −0.065 | 0.024 | 0.0074 | 0.004 | 0.034 | 0.914 |
| REA | A1457G | 0.152 | 0.056 | 1513 | 0.0070 | 0.0192 | 0.145 | 0.057 | 0.0103 | −0.063 | 0.080 | 0.429 |
| CUTT | A1457G | 0.148 | 0.056 | 1505 | 0.0078 | 0.0287 | 0.147 | 0.056 | 0.0088 | −0.011 | 0.079 | 0.887 |
| CARCFAT | A1457G | −0.221 | 0.084 | 1505 | 0.0085 | 0.0110 | −0.238 | 0.085 | 0.0051 | −0.173 | 0.119 | 0.147 |
| PREDYG | A1457G | −0.033 | 0.013 | 1505 | 0.0085 | 0.0110 | −0.036 | 0.013 | 0.0051 | −0.026 | 0.018 | 0.147 |

TABLE 23-continued

Traits, markers, allelic substitutions and effects

| Trait | Marker | Allele Substitution | | | | Fixed Effect | Additive | | | Dominance | | |
| --- | --- | --- | --- | --- | --- | --- | --- | --- | --- | --- | --- | --- |
| Trait | Marker | Estimate | StdErr | DF | P-value | ProbF | Estimate | StdErr | P-value | Estimate | StdErr | P-value |
| BFAT | A1457G | −0.013 | 0.005 | 1494 | 0.0106 | 0.0114 | −0.014 | 0.005 | 0.0061 | −0.011 | 0.007 | 0.120 |
| COST | A1457G | 3.380 | 1.688 | 1513 | 0.0455 | 0.0488 | 3.710 | 1.703 | 0.0296 | 3.427 | 2.398 | 0.153 |
| BFATRATE | A1457G | 0.000 | 0.000 | 1494 | 0.0470 | 0.1296 | 0.000 | 0.000 | 0.0435 | 0.000 | 0.000 | 0.706 |
| HCW | A1457G | 4.583 | 2.354 | 1513 | 0.0517 | 0.1159 | 4.818 | 2.377 | 0.0428 | 2.431 | 3.346 | 0.468 |
| WT3 | A1457G | 6.765 | 3.520 | 1513 | 0.0548 | 0.1552 | 6.859 | 3.554 | 0.0538 | 0.979 | 5.004 | 0.845 |
| FRAME | A1457G | 0.060 | 0.031 | 1513 | 0.0555 | 0.0975 | 0.065 | 0.032 | 0.0422 | 0.044 | 0.045 | 0.320 |
| CALCWT | A1457G | 6.590 | 3.519 | 1513 | 0.0613 | 0.1703 | 6.685 | 3.553 | 0.0601 | 0.982 | 5.002 | 0.844 |
| INWT | A1457G | 4.478 | 2.400 | 1513 | 0.0623 | 0.0880 | 4.865 | 2.422 | 0.0448 | 4.017 | 3.410 | 0.239 |
| MBS | A1457G | −0.591 | 0.354 | 1105 | 0.0950 | 0.1431 | −0.628 | 0.355 | 0.0776 | −0.528 | 0.503 | 0.294 |
| DOF | A1457G | 0.134 | 0.092 | 1513 | 0.1439 | 0.1398 | 0.117 | 0.092 | 0.2054 | −0.175 | 0.130 | 0.180 |
| REAHCW | A1457G | 0.010 | 0.007 | 1513 | 0.1625 | 0.1286 | 0.009 | 0.008 | 0.2359 | −0.016 | 0.011 | 0.142 |
| YG | A1457G | −0.026 | 0.022 | 1443 | 0.2425 | 0.4179 | −0.024 | 0.022 | 0.2817 | 0.019 | 0.032 | 0.538 |
| ADDCARCVAL | A1457G | −1.652 | 1.419 | 1513 | 0.2444 | 0.4943 | −1.607 | 1.433 | 0.2622 | 0.472 | 2.017 | 0.815 |
| DMI | A1457G | 13.112 | 14.603 | 1513 | 0.3694 | 0.5977 | 12.165 | 14.743 | 0.4094 | −9.824 | 20.759 | 0.636 |
| CHOICEQG | A1457G | 0.008 | 0.017 | 1503 | 0.6312 | 0.8545 | 0.009 | 0.017 | 0.6066 | 0.007 | 0.025 | 0.772 |
| ADG | A1457G | 0.007 | 0.016 | 1513 | 0.6474 | 0.7788 | 0.006 | 0.016 | 0.7040 | −0.012 | 0.023 | 0.590 |
| DP | A1457G | 0.031 | 0.070 | 1513 | 0.6571 | 0.3843 | 0.044 | 0.071 | 0.5368 | 0.130 | 0.099 | 0.190 |
| ADJNR | A1457G | −1.210 | 2.973 | 1513 | 0.6841 | 0.6970 | −0.906 | 3.002 | 0.7627 | 3.153 | 4.226 | 0.456 |
| CHOICEMBS | A1457G | −0.008 | 0.020 | 1105 | 0.6929 | 0.5784 | −0.010 | 0.020 | 0.6251 | −0.028 | 0.029 | 0.333 |
| HCWVALUE | A1457G | 0.045 | 0.182 | 1513 | 0.8062 | 0.7612 | 0.062 | 0.184 | 0.7356 | 0.181 | 0.259 | 0.486 |
| ADJRTR | A1457G | −0.573 | 3.182 | 1513 | 0.8572 | 0.8903 | −0.768 | 3.213 | 0.8112 | −2.024 | 4.524 | 0.655 |
| QUALITY | A1457G | 0.002 | 0.020 | 1503 | 0.9181 | 0.8049 | 0.000 | 0.020 | 0.9895 | −0.018 | 0.028 | 0.515 |
| MBS | A252T | −0.956 | 0.811 | 1072 | 0.239 | 0.439 | −0.306 | 1.510 | 0.839 | 0.894 | 1.753 | 0.610 |
| CALCYG | A252T | 0.060 | 0.051 | 1457 | 0.244 | 0.128 | 0.176 | 0.087 | 0.043 | 0.174 | 0.105 | 0.097 |
| CUTT | A252T | −0.135 | 0.119 | 1457 | 0.258 | 0.141 | −0.398 | 0.201 | 0.048 | −0.394 | 0.243 | 0.104 |
| DP | A252T | 0.166 | 0.150 | 1465 | 0.268 | 0.458 | 0.047 | 0.253 | 0.852 | −0.178 | 0.306 | 0.561 |
| BFAT | A252T | 0.011 | 0.011 | 1447 | 0.305 | 0.299 | 0.028 | 0.018 | 0.122 | 0.026 | 0.022 | 0.243 |
| PREDYG | A252T | 0.027 | 0.027 | 1457 | 0.316 | 0.301 | 0.070 | 0.045 | 0.122 | 0.065 | 0.055 | 0.237 |
| CARCFAT | A252T | 0.180 | 0.180 | 1457 | 0.316 | 0.301 | 0.468 | 0.303 | 0.122 | 0.432 | 0.365 | 0.237 |
| REAHCW | A252T | −0.016 | 0.016 | 1465 | 0.329 | 0.232 | −0.046 | 0.027 | 0.088 | −0.046 | 0.033 | 0.161 |
| ADJNR | A252T | −6.040 | 6.315 | 1465 | 0.339 | 0.536 | −11.020 | 10.673 | 0.302 | −7.453 | 12.877 | 0.563 |
| QUALITY | A252T | −0.034 | 0.042 | 1456 | 0.413 | 0.362 | −0.101 | 0.071 | 0.154 | −0.100 | 0.086 | 0.243 |
| YG | A252T | 0.035 | 0.049 | 1398 | 0.468 | 0.700 | 0.006 | 0.084 | 0.947 | −0.043 | 0.101 | 0.666 |
| BFATRATE | A252T | 0.000 | 0.000 | 1447 | 0.470 | 0.287 | 0.001 | 0.000 | 0.119 | 0.001 | 0.000 | 0.160 |
| CHOICEMBS | A252T | 0.032 | 0.046 | 1072 | 0.486 | 0.771 | 0.045 | 0.085 | 0.596 | 0.018 | 0.099 | 0.854 |
| HCW | A252T | 3.437 | 5.010 | 1465 | 0.493 | 0.767 | 5.121 | 8.468 | 0.545 | 2.521 | 10.216 | 0.805 |
| COST | A252T | 2.299 | 3.597 | 1465 | 0.523 | 0.753 | 0.348 | 6.080 | 0.954 | −2.921 | 7.335 | 0.691 |
| INWT | A252T | 2.786 | 5.108 | 1465 | 0.586 | 0.712 | −1.508 | 8.633 | 0.861 | −6.427 | 10.415 | 0.537 |
| REA | A252T | −0.056 | 0.120 | 1465 | 0.642 | 0.419 | −0.258 | 0.203 | 0.204 | −0.302 | 0.245 | 0.217 |
| WT3 | A252T | 3.170 | 7.490 | 1465 | 0.672 | 0.865 | 6.583 | 12.660 | 0.603 | 5.108 | 15.274 | 0.738 |
| FRAME | A252T | 0.027 | 0.067 | 1465 | 0.692 | 0.574 | 0.116 | 0.113 | 0.307 | 0.134 | 0.137 | 0.329 |
| CHOICEQG | A252T | 0.014 | 0.037 | 1456 | 0.704 | 0.487 | 0.071 | 0.062 | 0.254 | 0.085 | 0.075 | 0.255 |
| CALCWT | A252T | 2.163 | 7.481 | 1465 | 0.773 | 0.879 | 6.423 | 12.645 | 0.612 | 6.377 | 15.255 | 0.676 |
| ADJRTR | A252T | 1.636 | 6.763 | 1465 | 0.809 | 0.579 | 11.009 | 11.428 | 0.335 | 14.029 | 13.787 | 0.309 |
| ADDCARCVAL | A252T | 0.707 | 3.024 | 1465 | 0.815 | 0.704 | −2.610 | 5.110 | 0.610 | −4.964 | 6.165 | 0.421 |
| ADG | A252T | −0.008 | 0.034 | 1465 | 0.824 | 0.347 | 0.059 | 0.057 | 0.304 | 0.099 | 0.069 | 0.150 |
| DOF | A252T | −0.038 | 0.195 | 1465 | 0.845 | 0.981 | −0.036 | 0.330 | 0.913 | 0.003 | 0.398 | 0.993 |
| HCWVALUE | A252T | 0.051 | 0.386 | 1465 | 0.895 | 0.720 | 0.471 | 0.652 | 0.470 | 0.629 | 0.786 | 0.424 |
| DMI | A252T | −2.743 | 30.992 | 1465 | 0.929 | 0.221 | 70.526 | 52.332 | 0.178 | 109.661 | 63.137 | 0.083 |
| HCW | C963T | 7.031 | 2.339 | 1531 | 0.003 | 0.009 | 7.281 | 2.382 | 0.002 | 1.870 | 3.350 | 0.577 |
| CALCWT | C963T | 10.105 | 3.495 | 1531 | 0.004 | 0.015 | 10.128 | 3.560 | 0.004 | 0.168 | 5.005 | 0.973 |
| WT3 | C963T | 10.098 | 3.496 | 1531 | 0.004 | 0.016 | 10.073 | 3.561 | 0.005 | −0.182 | 5.008 | 0.971 |
| COST | C963T | 4.848 | 1.681 | 1531 | 0.004 | 0.008 | 5.223 | 1.712 | 0.002 | 2.802 | 2.407 | 0.244 |
| INWT | C963T | 6.654 | 2.390 | 1531 | 0.005 | 0.015 | 7.047 | 2.434 | 0.004 | 2.932 | 3.422 | 0.392 |
| REA | C963T | 0.148 | 0.056 | 1531 | 0.008 | 0.026 | 0.142 | 0.057 | 0.013 | −0.046 | 0.080 | 0.565 |
| PREDYG | C963T | −0.033 | 0.012 | 1523 | 0.009 | 0.022 | −0.035 | 0.013 | 0.006 | −0.016 | 0.018 | 0.363 |
| CARCFAT | C963T | −0.218 | 0.083 | 1523 | 0.009 | 0.022 | −0.232 | 0.085 | 0.006 | −0.108 | 0.119 | 0.364 |
| FRAME | C963T | 0.080 | 0.031 | 1531 | 0.010 | 0.035 | 0.082 | 0.032 | 0.010 | 0.014 | 0.045 | 0.747 |
| BFAT | C963T | −0.013 | 0.005 | 1512 | 0.011 | 0.024 | −0.014 | 0.005 | 0.007 | −0.007 | 0.007 | 0.315 |
| BFATRATE | C963T | 0.000 | 0.000 | 1512 | 0.019 | 0.063 | 0.000 | 0.000 | 0.022 | 0.000 | 0.000 | 0.956 |
| CALCYG | C963T | −0.054 | 0.024 | 1523 | 0.024 | 0.078 | −0.053 | 0.024 | 0.030 | 0.006 | 0.034 | 0.857 |
| CUTT | C963T | 0.121 | 0.055 | 1523 | 0.028 | 0.088 | 0.119 | 0.056 | 0.034 | −0.015 | 0.079 | 0.846 |
| MBS | C963T | −0.615 | 0.350 | 1118 | 0.079 | 0.123 | −0.672 | 0.355 | 0.058 | −0.531 | 0.502 | 0.290 |
| DOF | C963T | 0.149 | 0.091 | 1531 | 0.100 | 0.164 | 0.133 | 0.093 | 0.152 | −0.124 | 0.130 | 0.340 |
| DMI | C963T | 22.381 | 14.500 | 1531 | 0.123 | 0.302 | 22.022 | 14.769 | 0.136 | −2.676 | 20.768 | 0.897 |
| YG | C963T | −0.026 | 0.022 | 1461 | 0.242 | 0.408 | −0.023 | 0.023 | 0.307 | 0.021 | 0.032 | 0.514 |
| ADG | C963T | 0.017 | 0.016 | 1531 | 0.274 | 0.477 | 0.016 | 0.016 | 0.330 | −0.012 | 0.023 | 0.594 |
| ADDCARCVAL | C963T | −1.065 | 1.407 | 1531 | 0.449 | 0.733 | −1.124 | 1.433 | 0.433 | −0.443 | 2.016 | 0.826 |
| DP | C963T | 0.051 | 0.069 | 1531 | 0.460 | 0.362 | 0.068 | 0.071 | 0.339 | 0.121 | 0.099 | 0.223 |
| HCWVALUE | C963T | 0.127 | 0.181 | 1531 | 0.482 | 0.466 | 0.162 | 0.184 | 0.378 | 0.263 | 0.258 | 0.310 |
| REAHCW | C963T | 0.004 | 0.007 | 1531 | 0.574 | 0.449 | 0.003 | 0.008 | 0.735 | −0.012 | 0.011 | 0.257 |
| CHOICEQG | C963T | 0.009 | 0.017 | 1521 | 0.597 | 0.813 | 0.010 | 0.017 | 0.556 | 0.009 | 0.025 | 0.714 |

TABLE 23-continued

Traits, markers, allelic substitutions and effects

| Trait | Marker | Allele Substitution | | | | Fixed Effect | Additive | | | Dominance | | |
|---|---|---|---|---|---|---|---|---|---|---|---|---|
| Trait | Marker | Estimate | StdErr | DF | P-value | ProbF | Estimate | StdErr | P-value | Estimate | StdErr | P-value |
| CHOICEMBS | C963T | −0.006 | 0.020 | 1118 | 0.751 | 0.719 | −0.009 | 0.020 | 0.669 | −0.022 | 0.029 | 0.455 |
| QUALITY | C963T | −0.004 | 0.020 | 1521 | 0.831 | 0.620 | −0.008 | 0.020 | 0.696 | −0.027 | 0.028 | 0.340 |
| ADJRTR | C963T | 0.558 | 3.152 | 1531 | 0.860 | 0.870 | 0.257 | 3.210 | 0.936 | −2.241 | 4.514 | 0.620 |
| ADJNR | C963T | −0.141 | 2.949 | 1531 | 0.962 | 0.756 | 0.282 | 3.004 | 0.925 | 3.152 | 4.223 | 0.456 |
| CALCYG | A1457G | −0.065 | 0.024 | 1505 | 0.0065 | 0.0247 | −0.065 | 0.024 | 0.0074 | 0.004 | 0.034 | 0.914 |
| REA | A1457G | 0.152 | 0.056 | 1513 | 0.0070 | 0.0192 | 0.145 | 0.057 | 0.0103 | −0.063 | 0.080 | 0.429 |
| CUTT | A1457G | 0.148 | 0.056 | 1505 | 0.0078 | 0.0287 | 0.147 | 0.056 | 0.0088 | −0.011 | 0.079 | 0.887 |
| CARCFAT | A1457G | −0.221 | 0.084 | 1505 | 0.0085 | 0.0110 | −0.238 | 0.085 | 0.0051 | −0.173 | 0.119 | 0.147 |
| PREDYG | A1457G | −0.033 | 0.013 | 1505 | 0.0085 | 0.0110 | −0.036 | 0.013 | 0.0051 | −0.026 | 0.018 | 0.147 |
| BFAT | A1457G | −0.013 | 0.005 | 1494 | 0.0106 | 0.0114 | −0.014 | 0.005 | 0.0061 | −0.011 | 0.007 | 0.120 |
| COST | A1457G | 3.380 | 1.688 | 1513 | 0.0455 | 0.0488 | 3.710 | 1.703 | 0.0296 | 3.427 | 2.398 | 0.153 |
| BFATRATE | A1457G | 0.000 | 0.000 | 1494 | 0.0470 | 0.1296 | 0.000 | 0.000 | 0.0435 | 0.000 | 0.000 | 0.706 |
| HCW | A1457G | 4.583 | 2.354 | 1513 | 0.0517 | 0.1159 | 4.818 | 2.377 | 0.0428 | 2.431 | 3.346 | 0.468 |
| WT3 | A1457G | 6.765 | 3.520 | 1513 | 0.0548 | 0.1552 | 6.859 | 3.554 | 0.0538 | 0.979 | 5.004 | 0.845 |
| FRAME | A1457G | 0.060 | 0.031 | 1513 | 0.0555 | 0.0975 | 0.065 | 0.032 | 0.0422 | 0.044 | 0.045 | 0.320 |
| CALCWT | A1457G | 6.590 | 3.519 | 1513 | 0.0613 | 0.1703 | 6.685 | 3.553 | 0.0601 | 0.982 | 5.002 | 0.844 |
| INWT | A1457G | 4.478 | 2.400 | 1513 | 0.0623 | 0.0880 | 4.865 | 2.422 | 0.0448 | 4.017 | 3.410 | 0.239 |
| MBS | A1457G | −0.591 | 0.354 | 1105 | 0.0950 | 0.1431 | −0.628 | 0.355 | 0.0776 | −0.528 | 0.503 | 0.294 |
| DOF | A1457G | 0.134 | 0.092 | 1513 | 0.1439 | 0.1398 | 0.117 | 0.092 | 0.2054 | −0.175 | 0.130 | 0.180 |
| REAHCW | A1457G | 0.010 | 0.007 | 1513 | 0.1625 | 0.1286 | 0.009 | 0.008 | 0.2359 | −0.016 | 0.011 | 0.142 |
| YG | A1457G | −0.026 | 0.022 | 1443 | 0.2425 | 0.4179 | −0.024 | 0.022 | 0.2817 | 0.019 | 0.032 | 0.538 |
| ADDCARCVAL | A1457G | −1.652 | 1.419 | 1513 | 0.2444 | 0.4943 | −1.607 | 1.433 | 0.2622 | 0.472 | 2.017 | 0.815 |
| DMI | A1457G | 13.112 | 14.603 | 1513 | 0.3694 | 0.5977 | 12.165 | 14.743 | 0.4094 | −9.824 | 20.759 | 0.636 |
| CHOICEQG | A1457G | 0.008 | 0.017 | 1503 | 0.6312 | 0.8545 | 0.009 | 0.017 | 0.6066 | 0.007 | 0.025 | 0.772 |
| ADG | A1457G | 0.007 | 0.016 | 1513 | 0.6474 | 0.7788 | 0.006 | 0.016 | 0.7040 | −0.012 | 0.023 | 0.590 |
| DP | A1457G | 0.031 | 0.070 | 1513 | 0.6571 | 0.3843 | 0.044 | 0.071 | 0.5368 | 0.130 | 0.099 | 0.190 |
| ADJNR | A1457G | −1.210 | 2.973 | 1513 | 0.6841 | 0.6970 | −0.906 | 3.002 | 0.7627 | 3.153 | 4.226 | 0.456 |
| CHOICEMBS | A1457G | −0.008 | 0.020 | 1105 | 0.6929 | 0.5784 | −0.010 | 0.020 | 0.6251 | −0.028 | 0.029 | 0.333 |
| HCWVALUE | A1457G | 0.045 | 0.182 | 1513 | 0.8062 | 0.7612 | 0.062 | 0.184 | 0.7356 | 0.181 | 0.259 | 0.486 |
| ADJRTR | A1457G | −0.573 | 3.182 | 1513 | 0.8572 | 0.8903 | −0.768 | 3.213 | 0.8112 | −2.024 | 4.524 | 0.655 |
| QUALITY | A1457G | 0.002 | 0.020 | 1503 | 0.9181 | 0.8049 | 0.000 | 0.020 | 0.9895 | −0.018 | 0.028 | 0.515 |
| MBS | A252T | −0.956 | 0.811 | 1072 | 0.239 | 0.439 | −0.306 | 1.510 | 0.839 | 0.894 | 1.753 | 0.610 |
| CALCYG | A252T | 0.060 | 0.051 | 1457 | 0.244 | 0.128 | 0.176 | 0.087 | 0.043 | 0.174 | 0.105 | 0.097 |
| CUTT | A252T | −0.135 | 0.119 | 1457 | 0.258 | 0.141 | −0.398 | 0.201 | 0.048 | −0.394 | 0.243 | 0.104 |
| DP | A252T | 0.166 | 0.150 | 1465 | 0.268 | 0.458 | 0.047 | 0.253 | 0.852 | −0.178 | 0.306 | 0.561 |
| BFAT | A252T | 0.011 | 0.011 | 1447 | 0.305 | 0.299 | 0.028 | 0.018 | 0.122 | 0.026 | 0.022 | 0.243 |
| PREDYG | A252T | 0.027 | 0.027 | 1457 | 0.316 | 0.301 | 0.070 | 0.045 | 0.122 | 0.065 | 0.055 | 0.237 |
| CARCFAT | A252T | 0.180 | 0.180 | 1457 | 0.316 | 0.301 | 0.468 | 0.303 | 0.122 | 0.432 | 0.365 | 0.237 |
| REAHCW | A252T | −0.016 | 0.016 | 1465 | 0.329 | 0.232 | −0.046 | 0.027 | 0.088 | −0.046 | 0.033 | 0.161 |
| ADJNR | A252T | −6.040 | 6.315 | 1465 | 0.339 | 0.536 | −11.020 | 10.673 | 0.302 | −7.453 | 12.877 | 0.563 |
| QUALITY | A252T | −0.034 | 0.042 | 1456 | 0.413 | 0.362 | −0.101 | 0.071 | 0.154 | −0.100 | 0.086 | 0.243 |
| YG | A252T | 0.035 | 0.049 | 1398 | 0.468 | 0.700 | 0.006 | 0.084 | 0.947 | −0.043 | 0.101 | 0.666 |
| BFATRATE | A252T | 0.000 | 0.000 | 1447 | 0.470 | 0.287 | 0.001 | 0.000 | 0.119 | 0.001 | 0.000 | 0.160 |
| CHOICEMBS | A252T | 0.032 | 0.046 | 1072 | 0.486 | 0.771 | 0.045 | 0.085 | 0.596 | 0.018 | 0.099 | 0.854 |
| HCW | A252T | 3.437 | 5.010 | 1465 | 0.493 | 0.767 | 5.121 | 8.468 | 0.545 | 2.521 | 10.216 | 0.805 |
| COST | A252T | 2.299 | 3.597 | 1465 | 0.523 | 0.753 | 0.348 | 6.080 | 0.954 | −2.921 | 7.335 | 0.691 |
| INWT | A252T | 2.786 | 5.108 | 1465 | 0.586 | 0.712 | −1.508 | 8.633 | 0.861 | −6.427 | 10.415 | 0.537 |
| REA | A252T | −0.056 | 0.120 | 1465 | 0.642 | 0.419 | −0.258 | 0.203 | 0.204 | −0.302 | 0.245 | 0.217 |
| WT3 | A252T | 3.170 | 7.490 | 1465 | 0.672 | 0.865 | 6.583 | 12.660 | 0.603 | 5.108 | 15.274 | 0.738 |
| FRAME | A252T | 0.027 | 0.067 | 1465 | 0.692 | 0.574 | 0.116 | 0.113 | 0.307 | 0.134 | 0.137 | 0.329 |
| CHOICEQG | A252T | 0.014 | 0.037 | 1456 | 0.704 | 0.487 | 0.071 | 0.062 | 0.254 | 0.085 | 0.075 | 0.255 |
| CALCWT | A252T | 2.163 | 7.481 | 1465 | 0.773 | 0.879 | 6.423 | 12.645 | 0.612 | 6.377 | 15.255 | 0.676 |
| ADJRTR | A252T | 1.636 | 6.763 | 1465 | 0.809 | 0.579 | 11.009 | 11.428 | 0.335 | 14.029 | 13.787 | 0.309 |
| ADDCARCVAL | A252T | 0.707 | 3.024 | 1465 | 0.815 | 0.704 | −2.610 | 5.110 | 0.610 | −4.964 | 6.165 | 0.421 |
| ADG | A252T | −0.008 | 0.034 | 1465 | 0.824 | 0.347 | 0.059 | 0.057 | 0.304 | 0.099 | 0.069 | 0.150 |
| DOF | A252T | −0.038 | 0.195 | 1465 | 0.845 | 0.981 | −0.036 | 0.330 | 0.913 | 0.003 | 0.398 | 0.993 |
| HCWVALUE | A252T | 0.051 | 0.386 | 1465 | 0.895 | 0.720 | 0.471 | 0.652 | 0.470 | 0.629 | 0.786 | 0.424 |
| DMI | A252T | −2.743 | 30.992 | 1465 | 0.929 | 0.221 | 70.526 | 52.332 | 0.178 | 109.661 | 63.137 | 0.083 |
| HCW | C963T | 7.031 | 2.339 | 1531 | 0.003 | 0.009 | 7.281 | 2.382 | 0.002 | 1.870 | 3.350 | 0.577 |
| CALCWT | C963T | 10.105 | 3.495 | 1531 | 0.004 | 0.015 | 10.128 | 3.560 | 0.004 | 0.168 | 5.005 | 0.973 |
| WT3 | C963T | 10.098 | 3.496 | 1531 | 0.004 | 0.016 | 10.073 | 3.561 | 0.005 | −0.182 | 5.008 | 0.971 |
| COST | C963T | 4.848 | 1.681 | 1531 | 0.004 | 0.008 | 5.223 | 1.712 | 0.002 | 2.802 | 2.407 | 0.244 |
| INWT | C963T | 6.654 | 2.390 | 1531 | 0.005 | 0.015 | 7.047 | 2.434 | 0.004 | 2.932 | 3.422 | 0.392 |
| REA | C963T | 0.148 | 0.056 | 1531 | 0.008 | 0.026 | 0.142 | 0.057 | 0.013 | −0.046 | 0.080 | 0.565 |
| PREDYG | C963T | −0.033 | 0.012 | 1523 | 0.009 | 0.022 | −0.035 | 0.013 | 0.006 | −0.016 | 0.018 | 0.363 |
| CARCFAT | C963T | −0.218 | 0.083 | 1523 | 0.009 | 0.022 | −0.232 | 0.085 | 0.006 | −0.108 | 0.119 | 0.364 |
| FRAME | C963T | 0.080 | 0.031 | 1531 | 0.010 | 0.035 | 0.082 | 0.032 | 0.010 | 0.014 | 0.045 | 0.747 |
| BFAT | C963T | −0.013 | 0.005 | 1512 | 0.011 | 0.024 | −0.014 | 0.005 | 0.007 | −0.007 | 0.007 | 0.315 |
| BFATRATE | C963T | 0.000 | 0.000 | 1512 | 0.019 | 0.063 | 0.000 | 0.000 | 0.022 | 0.000 | 0.000 | 0.956 |
| CALCYG | C963T | −0.054 | 0.024 | 1523 | 0.024 | 0.078 | −0.053 | 0.024 | 0.030 | 0.006 | 0.034 | 0.857 |
| CUTT | C963T | 0.121 | 0.055 | 1523 | 0.028 | 0.088 | 0.119 | 0.056 | 0.034 | −0.015 | 0.079 | 0.846 |
| MBS | C963T | −0.615 | 0.350 | 1118 | 0.079 | 0.123 | −0.672 | 0.355 | 0.058 | −0.531 | 0.502 | 0.290 |

TABLE 23-continued

Traits, markers, allelic substitutions and effects

| Trait | Marker | Allele Substitution | | | | Fixed Effect ProbF | Additive | | | Dominance Estimate | StdErr | P-value |
|---|---|---|---|---|---|---|---|---|---|---|---|---|
| Trait | Marker | Estimate | StdErr | DF | P-value | | Estimate | StdErr | P-value | | | |
| DOF | C963T | 0.149 | 0.091 | 1531 | 0.100 | 0.164 | 0.133 | 0.093 | 0.152 | −0.124 | 0.130 | 0.340 |
| DMI | C963T | 22.381 | 14.500 | 1531 | 0.123 | 0.302 | 22.022 | 14.769 | 0.136 | −2.676 | 20.768 | 0.897 |
| YG | C963T | −0.026 | 0.022 | 1461 | 0.242 | 0.408 | −0.023 | 0.023 | 0.307 | 0.021 | 0.032 | 0.514 |
| ADG | C963T | 0.017 | 0.016 | 1531 | 0.274 | 0.477 | 0.016 | 0.016 | 0.330 | −0.012 | 0.023 | 0.594 |
| ADDCARCVAL | C963T | −1.065 | 1.407 | 1531 | 0.449 | 0.733 | −1.124 | 1.433 | 0.433 | −0.443 | 2.016 | 0.826 |
| DP | C963T | 0.051 | 0.069 | 1531 | 0.460 | 0.362 | 0.068 | 0.071 | 0.339 | 0.121 | 0.099 | 0.223 |
| HCWVALUE | C963T | 0.127 | 0.181 | 1531 | 0.482 | 0.466 | 0.162 | 0.184 | 0.378 | 0.263 | 0.258 | 0.310 |
| REAHCW | C963T | 0.004 | 0.007 | 1531 | 0.574 | 0.449 | 0.003 | 0.008 | 0.735 | −0.012 | 0.011 | 0.257 |
| CHOICEQG | C963T | 0.009 | 0.017 | 1521 | 0.597 | 0.813 | 0.010 | 0.017 | 0.556 | 0.009 | 0.025 | 0.714 |
| CHOICEMBS | C963T | −0.006 | 0.020 | 1118 | 0.751 | 0.719 | −0.009 | 0.020 | 0.669 | −0.022 | 0.029 | 0.455 |
| QUALITY | C963T | −0.004 | 0.020 | 1521 | 0.831 | 0.620 | −0.008 | 0.020 | 0.696 | −0.027 | 0.028 | 0.340 |
| ADJRTR | C963T | 0.558 | 3.152 | 1531 | 0.860 | 0.870 | 0.257 | 3.210 | 0.936 | −2.241 | 4.514 | 0.620 |
| ADJNR | C963T | −0.141 | 2.949 | 1531 | 0.962 | 0.756 | 0.282 | 3.004 | 0.925 | 3.152 | 4.223 | 0.456 |
| YG | GHR | −0.125 | 0.035 | 1452 | 0.0004 | 0.0002 | 0.251 | 0.069 | 0.000 | −0.165 | 0.078 | 0.034 |
| REA | GHR | 0.301 | 0.090 | 1520 | 0.0008 | 0.0038 | −0.314 | 0.180 | 0.081 | 0.017 | 0.201 | 0.934 |
| CUTT | GHR | 0.294 | 0.089 | 1512 | 0.0009 | 0.0033 | −0.403 | 0.177 | 0.023 | 0.140 | 0.198 | 0.480 |
| CALCYG | GHR | −0.125 | 0.038 | 1512 | 0.0011 | 0.0038 | 0.175 | 0.076 | 0.022 | −0.065 | 0.086 | 0.448 |
| PREDYG | GHR | −0.059 | 0.020 | 1512 | 0.0034 | 0.0021 | 0.127 | 0.040 | 0.002 | −0.088 | 0.045 | 0.051 |
| CARCFAT | GHR | −0.393 | 0.134 | 1512 | 0.0034 | 0.0021 | 0.845 | 0.268 | 0.002 | −0.584 | 0.300 | 0.051 |
| BFAT | GHR | −0.023 | 0.008 | 1501 | 0.0046 | 0.0027 | 0.050 | 0.016 | 0.002 | −0.035 | 0.018 | 0.050 |
| INWT | GHR | 10.802 | 3.840 | 1520 | 0.0050 | 0.0132 | −16.643 | 7.675 | 0.030 | 7.554 | 8.592 | 0.379 |
| COST | GHR | 7.285 | 2.703 | 1520 | 0.0071 | 0.0193 | −11.050 | 5.401 | 0.041 | 4.869 | 6.047 | 0.421 |
| FRAME | GHR | 0.135 | 0.050 | 1520 | 0.0074 | 0.0188 | −0.212 | 0.101 | 0.035 | 0.100 | 0.113 | 0.376 |
| DOF | GHR | −0.318 | 0.146 | 1520 | 0.0300 | 0.0933 | 0.270 | 0.293 | 0.357 | 0.062 | 0.328 | 0.849 |
| DP | GHR | 0.224 | 0.111 | 1520 | 0.0430 | 0.1204 | −0.153 | 0.221 | 0.490 | −0.092 | 0.248 | 0.710 |
| REAHCW | GHR | 0.024 | 0.012 | 1520 | 0.0468 | 0.1157 | −0.011 | 0.024 | 0.636 | −0.016 | 0.027 | 0.547 |
| HCW | GHR | 7.094 | 3.765 | 1520 | 0.0597 | 0.1058 | −13.443 | 7.524 | 0.074 | 8.209 | 8.424 | 0.330 |
| ADJRTR | GHR | 7.104 | 5.067 | 1520 | 0.1611 | 0.1841 | 3.349 | 10.124 | 0.741 | −13.517 | 11.335 | 0.233 |
| MBS | GHR | −0.747 | 0.552 | 1124 | 0.1761 | 0.3892 | 0.530 | 1.058 | 0.617 | 0.288 | 1.196 | 0.810 |
| CALCWT | GHR | 6.703 | 5.627 | 1520 | 0.2337 | 0.2363 | −18.500 | 11.242 | 0.100 | 15.254 | 12.586 | 0.226 |
| ADDCARCVAL | GHR | 2.619 | 2.264 | 1520 | 0.2475 | 0.1649 | 3.279 | 4.522 | 0.468 | −7.627 | 5.063 | 0.132 |
| WT3 | GHR | 6.383 | 5.627 | 1520 | 0.2568 | 0.2220 | −19.167 | 11.241 | 0.088 | 16.530 | 12.585 | 0.189 |
| CHOICEQG | GHR | −0.028 | 0.028 | 1511 | 0.3056 | 0.4911 | −0.001 | 0.055 | 0.988 | 0.038 | 0.062 | 0.542 |
| CHOICEMBS | GHR | −0.030 | 0.032 | 1124 | 0.3406 | 0.5980 | 0.012 | 0.061 | 0.841 | 0.024 | 0.069 | 0.728 |
| QUALITY | GHR | 0.026 | 0.032 | 1511 | 0.4115 | 0.6822 | −0.010 | 0.063 | 0.880 | −0.021 | 0.071 | 0.763 |
| BFATRATE | GHR | 0.000 | 0.000 | 1501 | 0.4377 | 0.3144 | 0.001 | 0.000 | 0.128 | −0.001 | 0.000 | 0.191 |
| ADJNR | GHR | 3.606 | 4.739 | 1520 | 0.4468 | 0.7457 | −4.356 | 9.473 | 0.646 | 0.969 | 10.606 | 0.927 |
| ADG | GHR | −0.018 | 0.025 | 1520 | 0.4804 | 0.5871 | −0.015 | 0.051 | 0.765 | 0.043 | 0.057 | 0.451 |
| HCWVALUE | GHR | 0.149 | 0.290 | 1520 | 0.6073 | 0.0836 | −1.235 | 0.578 | 0.033 | 1.405 | 0.648 | 0.030 |
| DMI | GHR | 0.858 | 23.265 | 1520 | 0.9706 | 0.6380 | −38.992 | 46.491 | 0.402 | 49.312 | 52.049 | 0.344 |
| COST | UASMS1 | −4.662 | 1.690 | 1529 | 0.006 | 0.016 | −4.924 | 1.722 | 0.004 | 1.929 | 2.407 | 0.423 |
| FRAME | UASMS1 | −0.086 | 0.031 | 1529 | 0.006 | 0.023 | −0.086 | 0.032 | 0.007 | 0.000 | 0.045 | 0.998 |
| PREDYG | UASMS1 | 0.034 | 0.013 | 1521 | 0.006 | 0.014 | 0.037 | 0.013 | 0.004 | −0.018 | 0.018 | 0.300 |
| CARCFAT | UASMS1 | 0.228 | 0.083 | 1521 | 0.006 | 0.014 | 0.245 | 0.085 | 0.004 | −0.123 | 0.119 | 0.300 |
| HCW | UASMS1 | −6.328 | 2.350 | 1529 | 0.007 | 0.026 | −6.465 | 2.394 | 0.007 | 1.004 | 3.347 | 0.764 |
| INWT | UASMS1 | −6.454 | 2.402 | 1529 | 0.007 | 0.024 | −6.710 | 2.447 | 0.006 | 1.882 | 3.421 | 0.582 |
| BFAT | UASMS1 | 0.013 | 0.005 | 1510 | 0.008 | 0.015 | 0.015 | 0.005 | 0.005 | −0.008 | 0.007 | 0.258 |
| CALCWT | UASMS1 | −9.034 | 3.514 | 1529 | 0.010 | 0.036 | −8.842 | 3.580 | 0.014 | −1.409 | 5.005 | 0.778 |
| REA | UASMS1 | −0.141 | 0.056 | 1529 | 0.012 | 0.034 | −0.133 | 0.057 | 0.020 | −0.057 | 0.080 | 0.479 |
| WT3 | UASMS1 | −8.750 | 3.515 | 1529 | 0.013 | 0.043 | −8.504 | 3.582 | 0.018 | −1.803 | 5.007 | 0.719 |
| CALCYG | UASMS1 | 0.056 | 0.024 | 1521 | 0.019 | 0.064 | 0.055 | 0.024 | 0.023 | 0.004 | 0.034 | 0.896 |
| CUTT | UASMS1 | −0.127 | 0.055 | 1521 | 0.023 | 0.074 | −0.125 | 0.056 | 0.027 | −0.010 | 0.079 | 0.900 |
| BFATRATE | UASMS1 | 0.000 | 0.000 | 1510 | 0.076 | 0.207 | 0.000 | 0.000 | 0.082 | 0.000 | 0.000 | 0.987 |
| MBS | UASMS1 | 0.587 | 0.353 | 1124 | 0.096 | 0.121 | 0.654 | 0.357 | 0.067 | −0.605 | 0.500 | 0.227 |
| DOF | UASMS1 | −0.138 | 0.091 | 1529 | 0.130 | 0.194 | −0.121 | 0.093 | 0.194 | −0.129 | 0.130 | 0.321 |
| DMI | UASMS1 | −19.530 | 14.570 | 1529 | 0.180 | 0.389 | −18.673 | 14.846 | 0.209 | −6.299 | 20.754 | 0.762 |
| ADDCARCVAL | UASMS1 | 1.780 | 1.414 | 1529 | 0.208 | 0.435 | 1.858 | 1.441 | 0.198 | −0.571 | 2.014 | 0.777 |
| YG | UASMS1 | 0.022 | 0.022 | 1461 | 0.326 | 0.382 | 0.018 | 0.023 | 0.437 | 0.031 | 0.032 | 0.327 |
| DP | UASMS1 | −0.052 | 0.070 | 1529 | 0.454 | 0.329 | −0.070 | 0.071 | 0.327 | 0.129 | 0.100 | 0.197 |
| ADG | UASMS1 | −0.012 | 0.016 | 1529 | 0.470 | 0.637 | −0.010 | 0.016 | 0.554 | −0.014 | 0.023 | 0.538 |
| REAHCW | UASMS1 | −0.005 | 0.007 | 1529 | 0.516 | 0.471 | −0.003 | 0.008 | 0.661 | −0.011 | 0.011 | 0.297 |
| CHOICEQG | UASMS1 | −0.010 | 0.017 | 1519 | 0.566 | 0.813 | −0.011 | 0.018 | 0.536 | 0.007 | 0.025 | 0.770 |
| HCWVALUE | UASMS1 | −0.100 | 0.182 | 1529 | 0.582 | 0.677 | −0.125 | 0.185 | 0.501 | 0.179 | 0.259 | 0.489 |
| CHOICEMBS | UASMS1 | 0.011 | 0.020 | 1124 | 0.603 | 0.673 | 0.013 | 0.021 | 0.532 | −0.021 | 0.029 | 0.470 |
| ADJNR | UASMS1 | 0.801 | 2.974 | 1529 | 0.788 | 0.854 | 0.516 | 3.030 | 0.865 | 2.091 | 4.236 | 0.622 |
| ADJRTR | UASMS1 | 0.658 | 3.167 | 1529 | 0.835 | 0.732 | 1.126 | 3.226 | 0.727 | −3.440 | 4.510 | 0.446 |
| QUALITY | UASMS1 | 0.002 | 0.020 | 1519 | 0.935 | 0.792 | 0.004 | 0.020 | 0.834 | −0.019 | 0.028 | 0.497 |
| INWT | UASMS2 | 7.349 | 2.638 | 1533 | 0.005 | 0.009 | 9.422 | 3.078 | 0.002 | 5.212 | 3.988 | 0.191 |
| COST | UASMS2 | 4.607 | 1.856 | 1533 | 0.013 | 0.019 | 6.099 | 2.166 | 0.005 | 3.751 | 2.806 | 0.182 |
| HCW | UASMS2 | 6.135 | 2.581 | 1533 | 0.018 | 0.010 | 9.067 | 3.009 | 0.003 | 7.372 | 3.900 | 0.059 |
| ADJRTR | UASMS2 | 7.042 | 3.476 | 1533 | 0.043 | 0.088 | 5.204 | 4.056 | 0.200 | −4.620 | 5.256 | 0.380 |
| FRAME | UASMS2 | 0.067 | 0.034 | 1533 | 0.053 | 0.031 | 0.104 | 0.040 | 0.010 | 0.094 | 0.052 | 0.073 |

TABLE 23-continued

Traits, markers, allelic substitutions and effects

| Trait | Marker | Allele Substitution | | | | Fixed Effect | Additive | | | Dominance | | |
|---|---|---|---|---|---|---|---|---|---|---|---|---|
| Trait | Marker | Estimate | StdErr | DF | P-value | ProbF | Estimate | StdErr | P-value | Estimate | StdErr | P-value |
| CALCWT | UASMS2 | 7.125 | 3.858 | 1533 | 0.065 | 0.031 | 11.506 | 4.498 | 0.011 | 11.014 | 5.829 | 0.059 |
| WT3 | UASMS2 | 7.058 | 3.859 | 1533 | 0.068 | 0.032 | 11.420 | 4.500 | 0.011 | 10.966 | 5.831 | 0.060 |
| DP | UASMS2 | 0.137 | 0.077 | 1533 | 0.074 | 0.196 | 0.150 | 0.090 | 0.095 | 0.031 | 0.116 | 0.788 |
| CHOICEQG | UASMS2 | −0.022 | 0.019 | 1523 | 0.253 | 0.488 | −0.018 | 0.022 | 0.425 | 0.010 | 0.029 | 0.724 |
| MBS | UASMS2 | 0.432 | 0.395 | 1124 | 0.274 | 0.516 | 0.344 | 0.467 | 0.462 | −0.209 | 0.593 | 0.724 |
| BFATRATE | UASMS2 | 0.000 | 0.000 | 1514 | 0.277 | 0.334 | 0.000 | 0.000 | 0.681 | 0.000 | 0.000 | 0.315 |
| DOF | UASMS2 | 0.103 | 0.100 | 1533 | 0.302 | 0.437 | 0.057 | 0.117 | 0.626 | −0.117 | 0.152 | 0.442 |
| DMI | UASMS2 | 15.746 | 15.975 | 1533 | 0.324 | 0.308 | 27.057 | 18.640 | 0.147 | 28.438 | 24.155 | 0.239 |
| REA | UASMS2 | 0.060 | 0.062 | 1533 | 0.332 | 0.556 | 0.042 | 0.072 | 0.560 | −0.045 | 0.093 | 0.630 |
| REAHCW | UASMS2 | −0.006 | 0.008 | 1533 | 0.455 | 0.080 | −0.017 | 0.010 | 0.083 | −0.026 | 0.012 | 0.034 |
| PREDYG | UASMS2 | 0.010 | 0.014 | 1525 | 0.461 | 0.691 | 0.007 | 0.016 | 0.686 | −0.009 | 0.021 | 0.658 |
| CARCFAT | UASMS2 | 0.068 | 0.092 | 1525 | 0.461 | 0.691 | 0.043 | 0.107 | 0.686 | −0.062 | 0.139 | 0.659 |
| QUALITY | UASMS2 | 0.014 | 0.022 | 1523 | 0.504 | 0.666 | 0.007 | 0.025 | 0.794 | −0.020 | 0.033 | 0.546 |
| BFAT | UASMS2 | 0.004 | 0.006 | 1514 | 0.509 | 0.749 | 0.002 | 0.006 | 0.711 | −0.003 | 0.008 | 0.707 |
| CUTT | UASMS2 | −0.035 | 0.061 | 1525 | 0.564 | 0.578 | −0.067 | 0.071 | 0.345 | −0.081 | 0.092 | 0.382 |
| ADDCARCVAL | UASMS2 | 0.828 | 1.552 | 1533 | 0.594 | 0.830 | 0.550 | 1.812 | 0.762 | −0.700 | 2.348 | 0.766 |
| CALCYG | UASMS2 | 0.013 | 0.026 | 1525 | 0.621 | 0.604 | 0.027 | 0.031 | 0.382 | 0.035 | 0.040 | 0.382 |
| HCWVALUE | UASMS2 | −0.084 | 0.200 | 1533 | 0.673 | 0.889 | −0.113 | 0.233 | 0.628 | −0.072 | 0.302 | 0.813 |
| ADJNR | UASMS2 | −1.280 | 3.260 | 1533 | 0.695 | 0.862 | −2.024 | 3.806 | 0.595 | −1.869 | 4.932 | 0.705 |
| YG | UASMS2 | −0.007 | 0.024 | 1464 | 0.759 | 0.858 | −0.001 | 0.029 | 0.983 | 0.017 | 0.037 | 0.645 |
| ADG | UASMS2 | −0.005 | 0.017 | 1533 | 0.780 | 0.308 | 0.011 | 0.020 | 0.590 | 0.040 | 0.026 | 0.131 |
| CHOICEMBS | UASMS2 | 0.000 | 0.023 | 1124 | 0.989 | 0.948 | −0.005 | 0.027 | 0.852 | −0.011 | 0.034 | 0.744 |
| PREDYG | EXON2FB | −0.043 | 0.013 | 1515 | 0.0007 | 0.0019 | −0.046 | 0.013 | 0.0004 | −0.018 | 0.018 | 0.309 |
| CARCFAT | EXON2FB | −0.288 | 0.085 | 1515 | 0.0007 | 0.0019 | −0.306 | 0.086 | 0.0004 | −0.122 | 0.120 | 0.310 |
| BFAT | EXON2FB | −0.017 | 0.005 | 1504 | 0.0009 | 0.0022 | −0.018 | 0.005 | 0.0005 | −0.008 | 0.007 | 0.270 |
| CALCYG | EXON2FB | −0.077 | 0.024 | 1515 | 0.0015 | 0.0063 | −0.078 | 0.025 | 0.0016 | −0.007 | 0.034 | 0.843 |
| CUTT | EXON2FB | 0.176 | 0.056 | 1515 | 0.0018 | 0.0074 | 0.178 | 0.057 | 0.0019 | 0.014 | 0.079 | 0.860 |
| REA | EXON2FB | 0.172 | 0.057 | 1522 | 0.0025 | 0.0095 | 0.167 | 0.058 | 0.0041 | −0.036 | 0.080 | 0.652 |
| COST | EXON2FB | 4.294 | 1.707 | 1522 | 0.0120 | 0.0393 | 4.431 | 1.741 | 0.0110 | 0.957 | 2.413 | 0.692 |
| INWT | EXON2FB | 5.950 | 2.426 | 1522 | 0.0143 | 0.0498 | 5.960 | 2.476 | 0.0162 | 0.070 | 3.431 | 0.984 |
| FRAME | EXON2FB | 0.076 | 0.032 | 1522 | 0.0166 | 0.0561 | 0.077 | 0.032 | 0.0174 | 0.007 | 0.045 | 0.878 |
| HCW | EXON2FB | 5.451 | 2.380 | 1522 | 0.0222 | 0.0731 | 5.467 | 2.429 | 0.0245 | 0.115 | 3.366 | 0.973 |
| BFATRATE | EXON2FB | 0.000 | 0.000 | 1504 | 0.0253 | 0.0736 | 0.000 | 0.000 | 0.0224 | 0.000 | 0.000 | 0.642 |
| CALCWT | EXON2FB | 7.753 | 3.551 | 1522 | 0.0292 | 0.0837 | 7.429 | 3.623 | 0.0405 | −2.279 | 5.022 | 0.650 |
| WT3 | EXON2FB | 7.295 | 3.553 | 1522 | 0.0402 | 0.1109 | 6.983 | 3.625 | 0.0543 | −2.196 | 5.024 | 0.662 |
| YG | EXON2FB | −0.044 | 0.023 | 1453 | 0.0538 | 0.1169 | −0.040 | 0.023 | 0.0819 | 0.024 | 0.032 | 0.448 |
| MBS | EXON2FB | −0.582 | 0.356 | 1124 | 0.1030 | 0.2121 | −0.623 | 0.362 | 0.0854 | −0.333 | 0.500 | 0.506 |
| REAHCW | EXON2FB | 0.011 | 0.008 | 1522 | 0.1302 | 0.2647 | 0.011 | 0.008 | 0.1726 | −0.006 | 0.011 | 0.544 |
| DOF | EXON2FB | 0.138 | 0.093 | 1522 | 0.1360 | 0.2601 | 0.125 | 0.095 | 0.1847 | −0.090 | 0.131 | 0.493 |
| HCWVALUE | EXON2FB | 0.253 | 0.183 | 1522 | 0.1683 | 0.2638 | 0.285 | 0.187 | 0.1277 | 0.227 | 0.259 | 0.381 |
| DMI | EXON2FB | 13.231 | 14.656 | 1522 | 0.3668 | 0.6591 | 12.819 | 14.955 | 0.3915 | −2.901 | 20.726 | 0.889 |
| CHOICEQG | EXON2FB | 0.014 | 0.017 | 1512 | 0.4283 | 0.3460 | 0.018 | 0.018 | 0.3073 | 0.030 | 0.025 | 0.221 |
| ADDCARCVAL | EXON2FB | −1.050 | 1.427 | 1522 | 0.4620 | 0.5833 | −1.260 | 1.456 | 0.3868 | −1.479 | 2.017 | 0.464 |
| DP | EXON2FB | 0.042 | 0.071 | 1522 | 0.5538 | 0.5102 | 0.056 | 0.072 | 0.4371 | 0.100 | 0.100 | 0.318 |
| QUALITY | EXON2FB | −0.007 | 0.020 | 1512 | 0.7319 | 0.2380 | −0.014 | 0.020 | 0.5040 | −0.047 | 0.028 | 0.097 |
| ADG | EXON2FB | 0.005 | 0.016 | 1522 | 0.7641 | 0.8246 | 0.003 | 0.016 | 0.8517 | −0.012 | 0.023 | 0.587 |
| CHOICEMBS | EXON2FB | 0.006 | 0.020 | 1124 | 0.7782 | 0.9437 | 0.005 | 0.021 | 0.8067 | −0.006 | 0.029 | 0.848 |
| ADJRTR | EXON2FB | −0.558 | 3.189 | 1522 | 0.8612 | 0.8362 | −0.925 | 3.254 | 0.7763 | −2.580 | 4.509 | 0.567 |
| ADJNR | EXON2FB | 0.038 | 3.001 | 1522 | 0.9899 | 0.9800 | 0.159 | 3.062 | 0.9586 | 0.851 | 4.244 | 0.841 |
| INWT | TFAM2 | 7.610 | 2.430 | 1534 | 0.002 | 0.007 | 7.724 | 2.530 | 0.002 | 0.570 | 3.502 | 0.871 |
| CALCWT | TFAM2 | 10.395 | 3.557 | 1534 | 0.004 | 0.014 | 10.648 | 3.702 | 0.004 | 1.269 | 5.125 | 0.804 |
| COST | TFAM2 | 4.922 | 1.710 | 1534 | 0.004 | 0.016 | 5.046 | 1.780 | 0.005 | 0.618 | 2.465 | 0.802 |
| WT3 | TFAM2 | 10.195 | 3.559 | 1534 | 0.004 | 0.016 | 10.392 | 3.704 | 0.005 | 0.985 | 5.128 | 0.848 |
| HCW | TFAM2 | 6.442 | 2.381 | 1534 | 0.007 | 0.026 | 6.382 | 2.478 | 0.010 | −0.302 | 3.430 | 0.930 |
| DOF | TFAM2 | 0.246 | 0.092 | 1534 | 0.008 | 0.000 | 0.168 | 0.096 | 0.080 | −0.393 | 0.133 | 0.003 |
| MBS | TFAM2 | 0.921 | 0.358 | 1121 | 0.010 | 0.035 | 0.959 | 0.373 | 0.010 | 0.196 | 0.516 | 0.705 |
| FRAME | TFAM2 | 0.068 | 0.032 | 1534 | 0.032 | 0.094 | 0.072 | 0.033 | 0.030 | 0.018 | 0.046 | 0.693 |
| REA | TFAM2 | 0.102 | 0.057 | 1534 | 0.074 | 0.200 | 0.099 | 0.059 | 0.095 | −0.014 | 0.082 | 0.865 |
| YG | TFAM2 | 0.035 | 0.023 | 1465 | 0.122 | 0.165 | 0.027 | 0.024 | 0.246 | −0.036 | 0.033 | 0.271 |
| DMI | TFAM2 | 19.963 | 14.753 | 1534 | 0.176 | 0.244 | 24.187 | 15.350 | 0.115 | 21.185 | 21.252 | 0.319 |
| HCWVALUE | TFAM2 | 0.238 | 0.184 | 1534 | 0.196 | 0.008 | 0.387 | 0.191 | 0.043 | 0.748 | 0.264 | 0.005 |
| ADDCARCVAL | TFAM2 | 1.591 | 1.434 | 1534 | 0.267 | 0.527 | 1.683 | 1.492 | 0.260 | 0.460 | 2.066 | 0.824 |
| QUALITY | TFAM2 | −0.022 | 0.020 | 1524 | 0.278 | 0.080 | −0.033 | 0.021 | 0.111 | −0.057 | 0.029 | 0.049 |
| CHOICEMBS | TFAM2 | 0.021 | 0.021 | 1121 | 0.303 | 0.543 | 0.024 | 0.021 | 0.271 | 0.012 | 0.030 | 0.687 |
| ADJNR | TFAM2 | 2.443 | 3.004 | 1534 | 0.416 | 0.719 | 2.455 | 3.126 | 0.433 | 0.056 | 4.329 | 0.990 |
| CHOICEQG | TFAM2 | 0.012 | 0.018 | 1524 | 0.496 | 0.294 | 0.019 | 0.018 | 0.295 | 0.035 | 0.025 | 0.159 |
| ADG | TFAM2 | 0.009 | 0.016 | 1534 | 0.557 | 0.739 | 0.012 | 0.017 | 0.481 | 0.012 | 0.023 | 0.611 |
| CALCYG | TFAM2 | −0.009 | 0.024 | 1526 | 0.696 | 0.897 | −0.008 | 0.025 | 0.760 | 0.009 | 0.035 | 0.798 |
| BFATRATE | TFAM2 | 0.000 | 0.000 | 1515 | 0.712 | 0.533 | 0.000 | 0.000 | 0.947 | 0.000 | 0.000 | 0.289 |
| CUTT | TFAM2 | 0.018 | 0.056 | 1526 | 0.746 | 0.927 | 0.015 | 0.059 | 0.801 | −0.018 | 0.081 | 0.829 |
| REAHCW | TFAM2 | −0.002 | 0.008 | 1534 | 0.755 | 0.930 | −0.003 | 0.008 | 0.719 | −0.002 | 0.011 | 0.828 |
| PREDYG | TFAM2 | −0.001 | 0.013 | 1526 | 0.937 | 0.949 | 0.000 | 0.013 | 0.992 | 0.006 | 0.018 | 0.754 |

TABLE 23-continued

Traits, markers, allelic substitutions and effects

| Trait | Marker | Allele Substitution | | | | Fixed Effect | Additive | | | Dominance Estimate | | |
|---|---|---|---|---|---|---|---|---|---|---|---|---|
| Trait | Marker | Estimate | StdErr | DF | P-value | ProbF | Estimate | StdErr | P-value | mate | StdErr | P-value |
| CARCFAT | TFAM2 | −0.007 | 0.085 | 1526 | 0.938 | 0.949 | 0.001 | 0.088 | 0.991 | 0.038 | 0.123 | 0.755 |
| BFAT | TFAM2 | 0.000 | 0.005 | 1515 | 0.972 | 0.938 | 0.000 | 0.005 | 0.949 | 0.003 | 0.007 | 0.721 |
| ADJRTR | TFAM2 | −0.091 | 3.212 | 1534 | 0.977 | 0.756 | −0.781 | 3.343 | 0.815 | −3.462 | 4.628 | 0.455 |
| DP | TFAM2 | 0.001 | 0.071 | 1534 | 0.989 | 0.663 | −0.017 | 0.074 | 0.813 | −0.093 | 0.102 | 0.365 |
| INWT | TFAM3 | −5.983 | 2.512 | 1421 | 0.017 | 0.053 | −6.186 | 2.552 | 0.015 | −1.612 | 3.540 | 0.649 |
| COST | TFAM3 | −3.671 | 1.774 | 1421 | 0.039 | 0.103 | −3.837 | 1.802 | 0.033 | −1.318 | 2.500 | 0.598 |
| WT3 | TFAM3 | −5.467 | 3.683 | 1421 | 0.138 | 0.300 | −5.768 | 3.742 | 0.123 | −2.384 | 5.190 | 0.646 |
| FRAME | TFAM3 | 0.006 | 0.033 | 1421 | 0.864 | 0.704 | 0.001 | 0.034 | 0.980 | −0.038 | 0.047 | 0.412 |
| QUALITY | TFAM3 | 0.035 | 0.021 | 1412 | 0.086 | 0.028 | 0.028 | 0.021 | 0.179 | −0.059 | 0.029 | 0.041 |
| HCW | TFAM3 | −3.136 | 2.463 | 1421 | 0.203 | 0.405 | −3.326 | 2.502 | 0.184 | −1.504 | 3.471 | 0.665 |
| REA | TFAM3 | −0.042 | 0.058 | 1421 | 0.471 | 0.176 | −0.024 | 0.059 | 0.683 | 0.142 | 0.082 | 0.086 |
| REAHCW | TFAM3 | 0.001 | 0.008 | 1421 | 0.867 | 0.129 | 0.004 | 0.008 | 0.604 | 0.022 | 0.011 | 0.044 |
| YG | TFAM3 | −0.018 | 0.023 | 1359 | 0.436 | 0.341 | −0.023 | 0.024 | 0.330 | −0.040 | 0.033 | 0.214 |
| HCWVALUE | TFAM3 | −0.350 | 0.189 | 1421 | 0.065 | 0.011 | −0.270 | 0.192 | 0.159 | 0.629 | 0.266 | 0.018 |
| CALCWT | TFAM3 | −6.247 | 3.675 | 1421 | 0.089 | 0.208 | −6.577 | 3.734 | 0.078 | −2.612 | 5.179 | 0.614 |
| DMI | TFAM3 | −12.902 | 15.185 | 1421 | 0.396 | 0.686 | −13.390 | 15.429 | 0.386 | −3.869 | 21.401 | 0.857 |
| DOF | TFAM3 | −0.061 | 0.096 | 1421 | 0.527 | 0.366 | −0.082 | 0.098 | 0.398 | −0.172 | 0.135 | 0.205 |
| BFATRATE | TFAM3 | 0.000 | 0.000 | 1402 | 0.833 | 0.722 | 0.000 | 0.000 | 0.730 | 0.000 | 0.000 | 0.436 |
| ADG | TFAM3 | 0.006 | 0.017 | 1421 | 0.721 | 0.909 | 0.005 | 0.017 | 0.759 | −0.006 | 0.023 | 0.802 |
| DP | TFAM3 | 0.059 | 0.074 | 1421 | 0.424 | 0.696 | 0.063 | 0.075 | 0.402 | 0.030 | 0.104 | 0.770 |
| BFAT | TFAM3 | −0.003 | 0.005 | 1402 | 0.603 | 0.804 | −0.002 | 0.005 | 0.660 | 0.003 | 0.007 | 0.684 |
| MBS | TFAM3 | −0.993 | 0.371 | 1056 | 0.008 | 0.028 | −0.995 | 0.377 | 0.008 | −0.010 | 0.519 | 0.984 |
| ADDCARCVAL | TFAM3 | −1.408 | 1.466 | 1421 | 0.337 | 0.587 | −1.507 | 1.490 | 0.312 | −0.779 | 2.066 | 0.706 |
| ADJNR | TFAM3 | −0.981 | 3.093 | 1421 | 0.751 | 0.912 | −1.140 | 3.143 | 0.717 | −1.260 | 4.360 | 0.773 |
| ADJRTR | TFAM3 | 3.856 | 3.305 | 1421 | 0.244 | 0.505 | 3.902 | 3.359 | 0.246 | 0.367 | 4.659 | 0.937 |
| PREDYG | TFAM3 | −0.006 | 0.013 | 1413 | 0.642 | 0.835 | −0.005 | 0.013 | 0.697 | 0.007 | 0.019 | 0.705 |
| CALCYG | TFAM3 | −0.005 | 0.025 | 1413 | 0.850 | 0.473 | −0.010 | 0.026 | 0.687 | −0.043 | 0.035 | 0.227 |
| CUTT | TFAM3 | 0.012 | 0.058 | 1413 | 0.831 | 0.435 | 0.026 | 0.059 | 0.662 | 0.105 | 0.082 | 0.203 |
| CARCFAT | TFAM3 | −0.041 | 0.088 | 1413 | 0.641 | 0.835 | −0.035 | 0.089 | 0.696 | 0.047 | 0.124 | 0.704 |
| CHOICEMBS | TFAM3 | −0.037 | 0.021 | 1056 | 0.077 | 0.155 | −0.034 | 0.021 | 0.109 | 0.023 | 0.030 | 0.433 |
| CHOICEQG | TFAM3 | −0.027 | 0.018 | 1412 | 0.131 | 0.130 | −0.023 | 0.018 | 0.209 | 0.034 | 0.025 | 0.179 |
| QUALITY | FABP4 | 0.079 | 0.022 | 1513 | 0.0004 | 0.002 | 0.074 | 0.027 | 0.006 | −0.011 | 0.035 | 0.744 |
| CHOICEQG | FABP4 | −0.066 | 0.019 | 1513 | 0.0007 | 0.003 | −0.060 | 0.024 | 0.012 | 0.015 | 0.031 | 0.635 |
| CHOICEMBS | FABP4 | −0.061 | 0.023 | 1115 | 0.0068 | 0.025 | −0.065 | 0.027 | 0.016 | −0.008 | 0.035 | 0.808 |
| REAHCW | FABP4 | 0.013 | 0.008 | 1523 | 0.1259 | 0.061 | 0.023 | 0.010 | 0.023 | 0.024 | 0.013 | 0.072 |
| CALCYG | FABP4 | −0.034 | 0.027 | 1515 | 0.2069 | 0.201 | −0.058 | 0.033 | 0.079 | −0.054 | 0.042 | 0.204 |
| CUTT | FABP4 | 0.076 | 0.063 | 1515 | 0.2271 | 0.191 | 0.134 | 0.076 | 0.078 | 0.134 | 0.098 | 0.173 |
| HCWVALUE | FABP4 | −0.238 | 0.205 | 1523 | 0.2469 | 0.279 | −0.083 | 0.248 | 0.737 | 0.354 | 0.322 | 0.271 |
| FRAME | FABP4 | −0.040 | 0.036 | 1523 | 0.2565 | 0.161 | −0.078 | 0.043 | 0.071 | −0.086 | 0.056 | 0.124 |
| DMI | FABP4 | −17.982 | 16.399 | 1523 | 0.2730 | 0.197 | −34.021 | 19.849 | 0.087 | −36.835 | 25.701 | 0.152 |
| COST | FABP4 | −1.848 | 1.917 | 1523 | 0.335 | 0.070 | −4.588 | 2.319 | 0.048 | −6.293 | 3.002 | 0.036 |
| MBS | FABP4 | −0.352 | 0.396 | 1115 | 0.374 | 0.505 | −0.157 | 0.472 | 0.739 | 0.463 | 0.610 | 0.448 |
| REA | FABP4 | 0.056 | 0.064 | 1523 | 0.377 | 0.647 | 0.069 | 0.077 | 0.369 | 0.030 | 0.100 | 0.764 |
| WT3 | FABP4 | −3.454 | 3.978 | 1523 | 0.385 | 0.107 | −8.684 | 4.813 | 0.071 | −12.011 | 6.232 | 0.054 |
| ADDCARCVAL | FABP4 | 1.288 | 1.600 | 1523 | 0.421 | 0.686 | 1.643 | 1.937 | 0.397 | 0.814 | 2.509 | 0.746 |
| CALCWT | FABP4 | −3.193 | 3.978 | 1523 | 0.422 | 0.103 | −8.559 | 4.813 | 0.076 | −12.323 | 6.231 | 0.048 |
| INWT | FABP4 | −2.179 | 2.726 | 1523 | 0.424 | 0.122 | −5.696 | 3.298 | 0.084 | −8.077 | 4.270 | 0.059 |
| HCW | FABP4 | −2.040 | 2.664 | 1523 | 0.444 | 0.051 | −6.244 | 3.221 | 0.053 | −9.656 | 4.171 | 0.021 |
| YG | FABP4 | −0.018 | 0.025 | 1454 | 0.461 | 0.429 | −0.037 | 0.030 | 0.226 | −0.042 | 0.039 | 0.283 |
| ADJRTR | FABP4 | −2.223 | 3.576 | 1523 | 0.534 | 0.490 | 0.266 | 4.330 | 0.951 | 5.718 | 5.607 | 0.308 |
| ADG | FABP4 | −0.011 | 0.018 | 1523 | 0.544 | 0.503 | −0.023 | 0.022 | 0.286 | −0.028 | 0.028 | 0.316 |
| PREDYG | FABP4 | −0.007 | 0.014 | 1515 | 0.612 | 0.827 | −0.011 | 0.017 | 0.537 | −0.008 | 0.022 | 0.725 |
| CARCFAT | FABP4 | −0.048 | 0.095 | 1515 | 0.613 | 0.827 | −0.071 | 0.115 | 0.537 | −0.053 | 0.149 | 0.724 |
| BFAT | FABP4 | −0.003 | 0.006 | 1504 | 0.638 | 0.849 | −0.004 | 0.007 | 0.567 | −0.003 | 0.009 | 0.745 |
| BFATRATE | FABP4 | 0.000 | 0.000 | 1504 | 0.904 | 0.930 | 0.000 | 0.000 | 0.918 | 0.000 | 0.000 | 0.717 |
| ADJNR | FABP4 | 0.124 | 3.355 | 1523 | 0.970 | 0.987 | 0.481 | 4.064 | 0.906 | 0.820 | 5.262 | 0.876 |
| DOF | FABP4 | −0.002 | 0.103 | 1523 | 0.981 | 0.515 | −0.084 | 0.125 | 0.503 | −0.186 | 0.162 | 0.249 |
| DP | FABP4 | 0.001 | 0.079 | 1523 | 0.991 | 0.484 | −0.064 | 0.096 | 0.503 | −0.149 | 0.124 | 0.228 |
| PREDYG | T945M | 0.093 | 0.026 | 1524 | 0.0003 | 0.001 | 0.103 | 0.063 | 0.104 | 0.011 | 0.068 | 0.868 |
| CARCFAT | T945M | 0.623 | 0.172 | 1524 | 0.0003 | 0.001 | 0.687 | 0.422 | 0.104 | 0.076 | 0.455 | 0.867 |
| BFAT | T945M | 0.037 | 0.010 | 1513 | 0.0004 | 0.002 | 0.041 | 0.025 | 0.105 | 0.005 | 0.027 | 0.850 |
| YG | T945M | 0.127 | 0.046 | 1462 | 0.0053 | 0.019 | 0.174 | 0.110 | 0.116 | 0.055 | 0.119 | 0.644 |
| CALCYG | T945M | 0.108 | 0.049 | 1524 | 0.0281 | 0.082 | 0.157 | 0.121 | 0.195 | 0.057 | 0.130 | 0.660 |
| CUTT | T945M | −0.246 | 0.114 | 1524 | 0.0312 | 0.087 | −0.373 | 0.280 | 0.183 | −0.150 | 0.302 | 0.618 |
| CHOICEMBS | T945M | −0.085 | 0.041 | 1118 | 0.0372 | 0.001 | 0.167 | 0.094 | 0.078 | 0.304 | 0.102 | 0.003 |
| BFATRATE | T945M | 0.000 | 0.000 | 1513 | 0.1279 | 0.261 | 0.001 | 0.001 | 0.239 | 0.000 | 0.001 | 0.543 |
| ADJNR | T945M | −8.175 | 6.009 | 1532 | 0.180 | 0.372 | −2.316 | 14.991 | 0.877 | 6.918 | 16.172 | 0.669 |
| HCWVALUE | T945M | −0.493 | 0.374 | 1532 | 0.188 | 0.214 | −1.467 | 0.918 | 0.110 | −1.150 | 0.991 | 0.246 |
| INWT | T945M | 4.604 | 4.955 | 1532 | 0.353 | 0.258 | 19.731 | 12.174 | 0.105 | 17.864 | 13.132 | 0.174 |
| ADG | T945M | −0.023 | 0.033 | 1532 | 0.483 | 0.782 | −0.025 | 0.080 | 0.756 | −0.002 | 0.087 | 0.978 |
| HCW | T945M | 3.027 | 4.852 | 1532 | 0.533 | 0.656 | 10.367 | 11.924 | 0.385 | 8.668 | 12.863 | 0.500 |
| WT3 | T945M | 4.163 | 7.246 | 1532 | 0.566 | 0.743 | 12.542 | 17.811 | 0.481 | 9.895 | 19.213 | 0.607 |

TABLE 23-continued

Traits, markers, allelic substitutions and effects

| Trait | Marker | Allele Substitution | | | | Fixed Effect | Additive | | | Dominance | | |
|---|---|---|---|---|---|---|---|---|---|---|---|---|
| Trait | Marker | Estimate | StdErr | DF | P-value | ProbF | Estimate | StdErr | P-value | Estimate | StdErr | P-value |
| COST | T945M | 1.959 | 3.487 | 1532 | 0.574 | 0.388 | 11.798 | 8.566 | 0.169 | 11.620 | 9.241 | 0.209 |
| CALCWT | T945M | 3.927 | 7.243 | 1532 | 0.588 | 0.715 | 13.919 | 17.801 | 0.434 | 11.801 | 19.203 | 0.539 |
| REAHCW | T945M | −0.008 | 0.015 | 1532 | 0.601 | 0.683 | −0.032 | 0.038 | 0.394 | −0.029 | 0.041 | 0.484 |
| DOF | T945M | 0.098 | 0.188 | 1532 | 0.603 | 0.547 | −0.311 | 0.462 | 0.502 | −0.482 | 0.498 | 0.333 |
| FRAME | T945M | −0.031 | 0.065 | 1532 | 0.631 | 0.707 | 0.068 | 0.159 | 0.670 | 0.117 | 0.172 | 0.496 |
| MBS | T945M | −0.335 | 0.717 | 1118 | 0.640 | 0.356 | 1.691 | 1.654 | 0.307 | 2.443 | 1.798 | 0.174 |
| ADJRTR | T945M | −2.853 | 6.517 | 1532 | 0.662 | 0.797 | 4.639 | 16.019 | 0.772 | 8.847 | 17.280 | 0.609 |
| DP | T945M | 0.035 | 0.144 | 1532 | 0.807 | 0.931 | 0.128 | 0.353 | 0.716 | 0.110 | 0.381 | 0.773 |
| QUALITY | T945M | 0.009 | 0.041 | 1522 | 0.817 | 0.864 | −0.035 | 0.100 | 0.725 | −0.053 | 0.108 | 0.625 |
| DMI | T945M | 6.422 | 29.933 | 1532 | 0.830 | 0.799 | 49.052 | 73.569 | 0.505 | 50.345 | 79.362 | 0.526 |
| ADDCARCVAL | T945M | −0.606 | 2.912 | 1532 | 0.835 | 0.580 | 6.079 | 7.155 | 0.396 | 7.895 | 7.719 | 0.307 |
| CHOICEQG | T945M | −0.005 | 0.036 | 1522 | 0.885 | 0.817 | 0.044 | 0.088 | 0.612 | 0.058 | 0.094 | 0.536 |
| REA | T945M | −0.005 | 0.116 | 1532 | 0.964 | 0.982 | −0.054 | 0.284 | 0.849 | −0.058 | 0.307 | 0.851 |
| COST | CRH | −4.918 | 1.785 | 1451 | 0.006 | 0.023 | −4.908 | 1.830 | 0.007 | 0.059 | 2.502 | 0.981 |
| REA | CRH | −0.159 | 0.059 | 1451 | 0.007 | 0.008 | −0.139 | 0.060 | 0.021 | 0.127 | 0.082 | 0.123 |
| FRAME | CRH | −0.087 | 0.033 | 1451 | 0.009 | 0.006 | −0.101 | 0.034 | 0.003 | −0.089 | 0.047 | 0.057 |
| INWT | CRH | −6.556 | 2.533 | 1451 | 0.010 | 0.034 | −6.728 | 2.596 | 0.010 | −1.079 | 3.550 | 0.761 |
| CUTT | CRH | −0.123 | 0.059 | 1443 | 0.036 | 0.072 | −0.111 | 0.060 | 0.066 | 0.077 | 0.082 | 0.349 |
| CALCYG | CRH | 0.053 | 0.025 | 1443 | 0.038 | 0.069 | 0.047 | 0.026 | 0.071 | −0.036 | 0.035 | 0.310 |
| HCW | CRH | −4.683 | 2.490 | 1451 | 0.060 | 0.165 | −4.528 | 2.552 | 0.076 | 0.976 | 3.489 | 0.780 |
| CALCWT | CRH | −6.699 | 3.716 | 1451 | 0.072 | 0.195 | −6.820 | 3.808 | 0.074 | −0.764 | 5.207 | 0.883 |
| WT3 | CRH | −6.614 | 3.722 | 1451 | 0.076 | 0.200 | −6.835 | 3.814 | 0.073 | −1.386 | 5.216 | 0.790 |
| ADJNR | CRH | −5.419 | 3.110 | 1451 | 0.082 | 0.191 | −5.052 | 3.187 | 0.113 | 2.305 | 4.359 | 0.597 |
| HCWVALUE | CRH | −0.331 | 0.190 | 1451 | 0.082 | 0.188 | −0.306 | 0.195 | 0.116 | 0.152 | 0.267 | 0.569 |
| CARCFAT | CRH | 0.144 | 0.089 | 1443 | 0.105 | 0.258 | 0.149 | 0.091 | 0.100 | 0.036 | 0.124 | 0.773 |
| PREDYG | CRH | 0.022 | 0.013 | 1443 | 0.105 | 0.258 | 0.022 | 0.014 | 0.100 | 0.005 | 0.019 | 0.771 |
| DOF | CRH | −0.155 | 0.097 | 1451 | 0.111 | 0.282 | −0.154 | 0.099 | 0.121 | 0.003 | 0.136 | 0.985 |
| BFAT | CRH | 0.008 | 0.005 | 1432 | 0.119 | 0.262 | 0.009 | 0.005 | 0.103 | 0.004 | 0.007 | 0.618 |
| ADJRTR | CRH | −4.907 | 3.327 | 1451 | 0.140 | 0.106 | −3.776 | 3.407 | 0.268 | 7.105 | 4.659 | 0.127 |
| REAHCW | CRH | −0.010 | 0.008 | 1451 | 0.195 | 0.186 | −0.008 | 0.008 | 0.326 | 0.014 | 0.011 | 0.195 |
| DMI | CRH | −19.089 | 15.357 | 1451 | 0.214 | 0.461 | −19.359 | 15.740 | 0.219 | −1.693 | 21.523 | 0.937 |
| ADDCARCVAL | CRH | −1.647 | 1.477 | 1451 | 0.265 | 0.515 | −1.743 | 1.513 | 0.250 | −0.602 | 2.070 | 0.771 |
| MBS | CRH | −0.354 | 0.374 | 1071 | 0.344 | 0.305 | −0.236 | 0.387 | 0.541 | 0.642 | 0.527 | 0.224 |
| YG | CRH | 0.021 | 0.024 | 1388 | 0.377 | 0.549 | 0.024 | 0.024 | 0.316 | 0.021 | 0.033 | 0.518 |
| QUALITY | CRH | 0.015 | 0.021 | 1442 | 0.479 | 0.636 | 0.012 | 0.021 | 0.581 | −0.019 | 0.029 | 0.524 |
| DP | CRH | −0.042 | 0.074 | 1451 | 0.575 | 0.391 | −0.021 | 0.076 | 0.783 | 0.130 | 0.104 | 0.211 |
| BFATRATE | CRH | 0.000 | 0.000 | 1432 | 0.632 | 0.885 | 0.000 | 0.000 | 0.660 | 0.000 | 0.000 | 0.900 |
| ADG | CRH | 0.007 | 0.017 | 1451 | 0.700 | 0.928 | 0.007 | 0.017 | 0.702 | 0.001 | 0.024 | 0.978 |
| CHOICEQG | CRH | −0.007 | 0.018 | 1442 | 0.714 | 0.930 | −0.006 | 0.019 | 0.739 | 0.003 | 0.025 | 0.911 |
| CHOICEMBS | CRH | −0.008 | 0.021 | 1071 | 0.716 | 0.783 | −0.004 | 0.022 | 0.839 | 0.018 | 0.030 | 0.551 |
| BFATRATE | DOPEY | 0.000 | 0.000 | 1409 | 0.011 | 0.023 | 0.000 | 0.000 | 0.007 | 0.000 | 0.000 | 0.293 |
| CALCYG | DOPEY | 0.062 | 0.025 | 1420 | 0.014 | 0.042 | 0.064 | 0.025 | 0.012 | 0.020 | 0.036 | 0.573 |
| CUTT | DOPEY | −0.139 | 0.058 | 1420 | 0.017 | 0.052 | −0.143 | 0.059 | 0.015 | −0.038 | 0.083 | 0.642 |
| CARCFAT | DOPEY | 0.195 | 0.087 | 1420 | 0.026 | 0.018 | 0.220 | 0.088 | 0.013 | 0.217 | 0.124 | 0.080 |
| PREDYG | DOPEY | 0.029 | 0.013 | 1420 | 0.026 | 0.018 | 0.033 | 0.013 | 0.013 | 0.033 | 0.019 | 0.080 |
| BFAT | DOPEY | 0.012 | 0.005 | 1409 | 0.027 | 0.021 | 0.013 | 0.005 | 0.014 | 0.013 | 0.007 | 0.090 |
| DOF | DOPEY | −0.198 | 0.097 | 1428 | 0.042 | 0.013 | −0.232 | 0.098 | 0.018 | −0.294 | 0.138 | 0.033 |
| REA | DOPEY | −0.103 | 0.058 | 1428 | 0.077 | 0.121 | −0.114 | 0.059 | 0.055 | −0.087 | 0.083 | 0.295 |
| MBS | DOPEY | 0.653 | 0.370 | 1057 | 0.077 | 0.133 | 0.609 | 0.372 | 0.102 | −0.500 | 0.522 | 0.338 |
| YG | DOPEY | 0.040 | 0.023 | 1366 | 0.083 | 0.136 | 0.044 | 0.023 | 0.061 | 0.033 | 0.033 | 0.319 |
| REAHCW | DOPEY | −0.013 | 0.008 | 1428 | 0.097 | 0.115 | −0.011 | 0.008 | 0.151 | 0.014 | 0.011 | 0.212 |
| ADJRTR | DOPEY | 4.888 | 3.310 | 1428 | 0.140 | 0.222 | 4.389 | 3.355 | 0.191 | −4.296 | 4.703 | 0.361 |
| QUALITY | DOPEY | −0.028 | 0.021 | 1419 | 0.179 | 0.099 | −0.022 | 0.021 | 0.292 | 0.049 | 0.029 | 0.093 |
| HCWVALUE | DOPEY | 0.230 | 0.189 | 1428 | 0.225 | 0.259 | 0.195 | 0.191 | 0.309 | −0.297 | 0.268 | 0.269 |
| CHOICEQG | DOPEY | 0.020 | 0.018 | 1419 | 0.270 | 0.254 | 0.016 | 0.018 | 0.374 | −0.032 | 0.026 | 0.217 |
| ADDCARCVAL | DOPEY | 1.611 | 1.467 | 1428 | 0.272 | 0.267 | 1.902 | 1.487 | 0.201 | 2.500 | 2.084 | 0.231 |
| DP | DOPEY | −0.077 | 0.074 | 1428 | 0.294 | 0.551 | −0.081 | 0.075 | 0.278 | −0.032 | 0.105 | 0.763 |
| ADG | DOPEY | 0.016 | 0.017 | 1428 | 0.336 | 0.066 | 0.010 | 0.017 | 0.545 | −0.050 | 0.024 | 0.034 |
| FRAME | DOPEY | −0.030 | 0.033 | 1428 | 0.373 | 0.011 | −0.045 | 0.034 | 0.177 | −0.135 | 0.047 | 0.004 |
| DMI | DOPEY | 10.227 | 15.169 | 1428 | 0.500 | 0.098 | 5.095 | 15.357 | 0.740 | −44.103 | 21.524 | 0.041 |
| ADJNR | DOPEY | 1.317 | 3.084 | 1428 | 0.669 | 0.049 | 2.551 | 3.121 | 0.414 | 10.601 | 4.374 | 0.015 |
| INWT | DOPEY | −0.983 | 2.511 | 1428 | 0.696 | 0.021 | −2.122 | 2.540 | 0.403 | −9.797 | 3.560 | 0.006 |
| COST | DOPEY | −0.563 | 1.773 | 1428 | 0.751 | 0.023 | −1.361 | 1.793 | 0.448 | −6.862 | 2.513 | 0.006 |
| HCW | DOPEY | −0.580 | 2.458 | 1428 | 0.814 | 0.005 | −1.901 | 2.483 | 0.444 | −11.359 | 3.480 | 0.001 |
| WT3 | DOPEY | 0.748 | 3.675 | 1428 | 0.839 | 0.006 | −1.187 | 3.713 | 0.749 | −16.631 | 5.204 | 0.001 |
| CHOICEMBS | DOPEY | 0.004 | 0.021 | 1057 | 0.868 | 0.749 | 0.005 | 0.021 | 0.797 | 0.022 | 0.030 | 0.458 |
| CALCWT | DOPEY | 0.377 | 3.672 | 1428 | 0.918 | 0.004 | −1.633 | 3.709 | 0.660 | −17.276 | 5.198 | 0.001 |
| FRAME | PAPD | −0.099 | 0.033 | 1437 | 0.003 | 0.001 | −0.086 | 0.033 | 0.011 | 0.098 | 0.046 | 0.034 |
| REA | PAPD | −0.127 | 0.058 | 1437 | 0.028 | 0.001 | −0.091 | 0.059 | 0.124 | 0.263 | 0.082 | 0.001 |
| HCW | PAPD | −4.540 | 2.453 | 1437 | 0.064 | 0.007 | −3.325 | 2.495 | 0.183 | 8.722 | 3.452 | 0.012 |
| CUTT | PAPD | −0.106 | 0.058 | 1429 | 0.067 | 0.080 | −0.091 | 0.059 | 0.123 | 0.106 | 0.082 | 0.192 |
| BFAT | PAPD | 0.010 | 0.005 | 1418 | 0.068 | 0.189 | 0.010 | 0.005 | 0.071 | 0.001 | 0.007 | 0.918 |

TABLE 23-continued

Traits, markers, allelic substitutions and effects

| Trait | Marker | Allele Substitution | | | | Fixed Effect ProbF | Additive | | | Dominance | | |
|---|---|---|---|---|---|---|---|---|---|---|---|---|
| Trait | Marker | Estimate | StdErr | DF | P-value | | Estimate | StdErr | P-value | Estimate | StdErr | P-value |
| CALCYG | PAPD | 0.045 | 0.025 | 1429 | 0.068 | 0.066 | 0.038 | 0.025 | 0.134 | −0.051 | 0.035 | 0.144 |
| CARCFAT | PAPD | 0.157 | 0.087 | 1429 | 0.073 | 0.198 | 0.160 | 0.089 | 0.074 | 0.022 | 0.123 | 0.859 |
| PREDYG | PAPD | 0.023 | 0.013 | 1429 | 0.073 | 0.198 | 0.024 | 0.013 | 0.074 | 0.003 | 0.018 | 0.859 |
| CALCWT | PAPD | −6.033 | 3.663 | 1437 | 0.100 | 0.025 | −4.473 | 3.729 | 0.230 | 11.192 | 5.160 | 0.030 |
| WT3 | PAPD | −5.546 | 3.668 | 1437 | 0.131 | 0.039 | −4.064 | 3.734 | 0.277 | 10.634 | 5.166 | 0.040 |
| COST | PAPD | −2.646 | 1.769 | 1437 | 0.135 | 0.008 | −1.697 | 1.799 | 0.346 | 6.810 | 2.489 | 0.006 |
| DMI | PAPD | −19.129 | 15.101 | 1437 | 0.205 | 0.416 | −17.968 | 15.395 | 0.243 | 8.326 | 21.302 | 0.696 |
| ADG | PAPD | −0.020 | 0.017 | 1437 | 0.239 | 0.396 | −0.017 | 0.017 | 0.305 | 0.016 | 0.023 | 0.496 |
| INWT | PAPD | −2.778 | 2.511 | 1437 | 0.269 | 0.016 | −1.469 | 2.554 | 0.565 | 9.396 | 3.534 | 0.008 |
| DP | PAPD | −0.072 | 0.073 | 1437 | 0.325 | 0.262 | −0.053 | 0.075 | 0.475 | 0.135 | 0.103 | 0.191 |
| HCWVALUE | PAPD | −0.169 | 0.188 | 1437 | 0.369 | 0.219 | −0.224 | 0.191 | 0.242 | −0.395 | 0.265 | 0.136 |
| REAHCW | PAPD | −0.006 | 0.008 | 1437 | 0.423 | 0.324 | −0.004 | 0.008 | 0.588 | 0.014 | 0.011 | 0.205 |
| DOF | PAPD | 0.066 | 0.097 | 1437 | 0.496 | 0.790 | 0.065 | 0.099 | 0.515 | −0.012 | 0.137 | 0.931 |
| CHOICEMBS | PAPD | 0.011 | 0.021 | 1063 | 0.590 | 0.803 | 0.013 | 0.022 | 0.539 | 0.011 | 0.030 | 0.701 |
| QUALITY | PAPD | 0.008 | 0.020 | 1428 | 0.679 | 0.516 | 0.013 | 0.021 | 0.540 | 0.031 | 0.029 | 0.283 |
| ADJRTR | PAPD | 1.331 | 3.283 | 1437 | 0.685 | 0.769 | 0.944 | 3.347 | 0.778 | −2.778 | 4.631 | 0.549 |
| YG | PAPD | 0.009 | 0.023 | 1375 | 0.685 | 0.812 | 0.007 | 0.023 | 0.760 | −0.016 | 0.032 | 0.616 |
| MBS | PAPD | −0.147 | 0.371 | 1063 | 0.692 | 0.924 | −0.145 | 0.381 | 0.704 | 0.012 | 0.525 | 0.982 |
| ADDCARCVAL | PAPD | 0.394 | 1.458 | 1437 | 0.787 | 0.574 | 0.102 | 1.485 | 0.945 | −2.094 | 2.055 | 0.309 |
| ADJNR | PAPD | −0.740 | 3.079 | 1437 | 0.810 | 0.822 | −1.090 | 3.138 | 0.728 | −2.513 | 4.342 | 0.563 |
| BFATRATE | PAPD | 0.000 | 0.000 | 1418 | 0.817 | 0.943 | 0.000 | 0.000 | 0.859 | 0.000 | 0.000 | 0.801 |
| CHOICEQG | PAPD | −0.001 | 0.018 | 1428 | 0.951 | 0.993 | −0.001 | 0.018 | 0.936 | −0.003 | 0.025 | 0.921 |
| FRAME | PAPD | −0.099 | 0.033 | 1437 | 0.003 | 0.001 | −0.086 | 0.033 | 0.011 | 0.098 | 0.046 | 0.034 |
| REA | PAPD | −0.127 | 0.058 | 1437 | 0.028 | 0.001 | −0.091 | 0.059 | 0.124 | 0.263 | 0.082 | 0.001 |
| HCW | PAPD | −4.540 | 2.453 | 1437 | 0.064 | 0.007 | −3.325 | 2.495 | 0.183 | 8.722 | 3.452 | 0.012 |
| CUTT | PAPD | −0.106 | 0.058 | 1429 | 0.067 | 0.080 | −0.091 | 0.059 | 0.123 | 0.106 | 0.082 | 0.192 |
| BFAT | PAPD | 0.010 | 0.005 | 1418 | 0.068 | 0.189 | 0.010 | 0.005 | 0.071 | 0.001 | 0.007 | 0.918 |
| CALCYG | PAPD | 0.045 | 0.025 | 1429 | 0.068 | 0.066 | 0.038 | 0.025 | 0.134 | −0.051 | 0.035 | 0.144 |
| CARCFAT | PAPD | 0.157 | 0.087 | 1429 | 0.073 | 0.198 | 0.160 | 0.089 | 0.074 | 0.022 | 0.123 | 0.859 |
| PREDYG | PAPD | 0.023 | 0.013 | 1429 | 0.073 | 0.198 | 0.024 | 0.013 | 0.074 | 0.003 | 0.018 | 0.859 |
| CALCWT | PAPD | −6.033 | 3.663 | 1437 | 0.100 | 0.025 | −4.473 | 3.729 | 0.230 | 11.192 | 5.160 | 0.030 |
| WT3 | PAPD | −5.546 | 3.668 | 1437 | 0.131 | 0.039 | −4.064 | 3.734 | 0.277 | 10.634 | 5.166 | 0.040 |
| COST | PAPD | −2.646 | 1.769 | 1437 | 0.135 | 0.008 | −1.697 | 1.799 | 0.346 | 6.810 | 2.489 | 0.006 |
| HCW | SREBP | 8.757 | 4.023 | 1184 | 0.030 | 0.072 | 9.859 | 4.300 | 0.022 | −7.500 | 10.316 | 0.467 |
| REA | SREBP | 0.191 | 0.096 | 1184 | 0.047 | 0.036 | 0.250 | 0.102 | 0.015 | −0.402 | 0.245 | 0.101 |
| DP | SREBP | 0.234 | 0.121 | 1184 | 0.053 | 0.128 | 0.261 | 0.129 | 0.043 | −0.189 | 0.309 | 0.540 |
| HCWVALUE | SREBP | 0.556 | 0.304 | 1184 | 0.068 | 0.102 | 0.428 | 0.325 | 0.188 | 0.868 | 0.781 | 0.266 |
| CALCWT | SREBP | 9.424 | 5.963 | 1184 | 0.114 | 0.246 | 10.679 | 6.374 | 0.094 | −8.534 | 15.293 | 0.577 |
| WT3 | SREBP | 9.292 | 5.967 | 1184 | 0.120 | 0.234 | 10.858 | 6.378 | 0.089 | −10.653 | 15.302 | 0.486 |
| CHOICEQG | SREBP | 0.039 | 0.029 | 1177 | 0.178 | 0.290 | 0.030 | 0.031 | 0.329 | 0.060 | 0.075 | 0.418 |
| FRAME | SREBP | 0.072 | 0.055 | 1184 | 0.191 | 0.091 | 0.108 | 0.059 | 0.065 | −0.247 | 0.140 | 0.079 |
| CALCYG | SREBP | −0.052 | 0.041 | 1178 | 0.210 | 0.416 | −0.058 | 0.044 | 0.185 | 0.046 | 0.106 | 0.667 |
| INWT | SREBP | 4.960 | 4.066 | 1184 | 0.223 | 0.331 | 6.267 | 4.346 | 0.150 | −8.891 | 10.427 | 0.394 |
| COST | SREBP | 3.515 | 2.903 | 1184 | 0.226 | 0.312 | 4.533 | 3.103 | 0.144 | −6.925 | 7.444 | 0.352 |
| CUTT | SREBP | 0.114 | 0.095 | 1178 | 0.231 | 0.445 | 0.129 | 0.102 | 0.203 | −0.106 | 0.246 | 0.666 |
| DMI | SREBP | 28.910 | 24.424 | 1184 | 0.237 | 0.430 | 23.949 | 26.109 | 0.359 | 33.743 | 62.638 | 0.590 |
| QUALITY | SREBP | −0.039 | 0.033 | 1177 | 0.245 | 0.337 | −0.027 | 0.036 | 0.443 | −0.078 | 0.086 | 0.363 |
| ADG | SREBP | 0.029 | 0.027 | 1184 | 0.288 | 0.561 | 0.031 | 0.029 | 0.293 | −0.012 | 0.070 | 0.867 |
| PREDYG | SREBP | −0.022 | 0.022 | 1178 | 0.312 | 0.436 | −0.015 | 0.023 | 0.505 | −0.045 | 0.056 | 0.424 |
| CARCFAT | SREBP | −0.145 | 0.144 | 1178 | 0.313 | 0.437 | −0.102 | 0.154 | 0.506 | −0.298 | 0.372 | 0.423 |
| BFAT | SREBP | −0.009 | 0.009 | 1170 | 0.318 | 0.496 | −0.007 | 0.009 | 0.474 | −0.014 | 0.023 | 0.523 |
| BFATRATE | SREBP | 0.000 | 0.000 | 1170 | 0.419 | 0.721 | 0.000 | 0.000 | 0.458 | 0.000 | 0.001 | 0.965 |
| ADJRTR | SREBP | −3.048 | 5.294 | 1184 | 0.565 | 0.663 | −4.446 | 5.659 | 0.432 | 9.506 | 13.575 | 0.484 |
| CHOICEMBS | SREBP | −0.020 | 0.035 | 897 | 0.575 | 0.625 | −0.009 | 0.038 | 0.813 | −0.073 | 0.092 | 0.429 |
| REAHCW | SREBP | 0.007 | 0.013 | 1184 | 0.605 | 0.489 | 0.012 | 0.014 | 0.387 | −0.035 | 0.033 | 0.281 |
| ADDCARCVAL | SREBP | 1.158 | 2.381 | 1184 | 0.627 | 0.568 | 2.007 | 2.545 | 0.430 | −5.779 | 6.106 | 0.344 |
| DOF | SREBP | 0.066 | 0.156 | 1184 | 0.672 | 0.564 | 0.008 | 0.166 | 0.960 | 0.392 | 0.399 | 0.326 |
| MBS | SREBP | 0.094 | 0.630 | 897 | 0.882 | 0.667 | 0.311 | 0.677 | 0.645 | −1.460 | 1.645 | 0.375 |
| ADJNR | SREBP | 0.351 | 4.898 | 1184 | 0.943 | 0.156 | 3.906 | 5.229 | 0.455 | −24.184 | 12.544 | 0.054 |
| YG | SREBP | −0.003 | 0.038 | 1132 | 0.945 | 0.996 | −0.003 | 0.040 | 0.932 | 0.006 | 0.096 | 0.951 |
| ADG | M1AFLP340 | 0.063 | 0.020 | 1400 | 0.001 | 0.003 | 0.082 | 0.026 | 0.002 | −0.036 | 0.033 | 0.276 |
| DMI | M1AFLP340 | 41.014 | 17.960 | 1400 | 0.023 | 0.069 | 46.922 | 23.773 | 0.049 | −11.368 | 29.957 | 0.704 |
| CALCWT | M1AFLP340 | 6.867 | 4.373 | 1400 | 0.117 | 0.288 | 7.470 | 5.788 | 0.197 | −1.161 | 7.294 | 0.874 |
| CHOICEMBS | M1AFLP340 | −0.036 | 0.025 | 1032 | 0.147 | 0.313 | −0.026 | 0.033 | 0.432 | −0.020 | 0.042 | 0.635 |
| WT3 | M1AFLP340 | 6.035 | 4.384 | 1400 | 0.169 | 0.388 | 5.946 | 5.803 | 0.306 | 0.170 | 7.313 | 0.981 |
| REA | M1AFLP340 | 0.088 | 0.070 | 1400 | 0.207 | 0.105 | −0.015 | 0.092 | 0.870 | 0.199 | 0.116 | 0.088 |
| HCW | M1AFLP340 | 3.580 | 2.939 | 1400 | 0.223 | 0.426 | 2.368 | 3.890 | 0.543 | 2.333 | 4.902 | 0.634 |
| CHOICEQG | M1AFLP340 | −0.026 | 0.021 | 1391 | 0.229 | 0.439 | −0.017 | 0.028 | 0.534 | −0.016 | 0.035 | 0.658 |
| QUALITY | M1AFLP340 | 0.026 | 0.024 | 1391 | 0.282 | 0.401 | 0.009 | 0.032 | 0.779 | 0.033 | 0.040 | 0.413 |
| INWT | M1AFLP340 | −3.214 | 3.000 | 1400 | 0.284 | 0.361 | −5.671 | 3.970 | 0.153 | 4.729 | 5.003 | 0.345 |
| DP | M1AFLP340 | −0.073 | 0.088 | 1400 | 0.404 | 0.110 | −0.219 | 0.116 | 0.058 | 0.282 | 0.146 | 0.054 |
| COST | M1AFLP340 | −1.647 | 2.121 | 1400 | 0.438 | 0.439 | −3.526 | 2.806 | 0.209 | 3.616 | 3.536 | 0.307 |

TABLE 23-continued

Traits, markers, allelic substitutions and effects

| Trait | Marker | Allele Substitution | | | | Fixed Effect | Additive | | | Dominance | | |
| --- | --- | --- | --- | --- | --- | --- | --- | --- | --- | --- | --- | --- |
| Trait | Marker | Estimate | StdErr | DF | P-value | ProbF | Estimate | StdErr | P-value | Estimate | StdErr | P-value |
| BFATRATE | M1AFLP340 | 0.000 | 0.000 | 1382 | 0.507 | 0.768 | 0.000 | 0.000 | 0.487 | 0.000 | 0.000 | 0.769 |
| ADJNR | M1AFLP340 | −2.046 | 3.662 | 1400 | 0.576 | 0.422 | −5.820 | 4.846 | 0.230 | 7.261 | 6.106 | 0.235 |
| FRAME | M1AFLP340 | −0.018 | 0.039 | 1400 | 0.649 | 0.885 | −0.024 | 0.052 | 0.639 | 0.013 | 0.065 | 0.847 |
| CARCFAT | M1AFLP340 | 0.043 | 0.104 | 1393 | 0.680 | 0.911 | 0.031 | 0.138 | 0.820 | 0.023 | 0.174 | 0.896 |
| PREDYG | M1AFLP340 | 0.006 | 0.016 | 1393 | 0.680 | 0.911 | 0.005 | 0.021 | 0.820 | 0.003 | 0.026 | 0.897 |
| REAHCW | M1AFLP340 | 0.004 | 0.009 | 1400 | 0.701 | 0.378 | −0.007 | 0.012 | 0.556 | 0.021 | 0.016 | 0.180 |
| BFAT | M1AFLP340 | 0.002 | 0.006 | 1382 | 0.716 | 0.922 | 0.001 | 0.008 | 0.871 | 0.002 | 0.010 | 0.861 |
| ADDCARCVAL | M1AFLP340 | 0.484 | 1.745 | 1400 | 0.781 | 0.675 | −0.789 | 2.310 | 0.733 | 2.451 | 2.910 | 0.400 |
| CALCYG | M1AFLP340 | −0.008 | 0.030 | 1393 | 0.787 | 0.582 | 0.018 | 0.040 | 0.651 | −0.050 | 0.050 | 0.315 |
| CUTT | M1AFLP340 | 0.015 | 0.069 | 1393 | 0.831 | 0.592 | −0.045 | 0.092 | 0.623 | 0.116 | 0.116 | 0.317 |
| YG | M1AFLP340 | 0.004 | 0.027 | 1338 | 0.889 | 0.329 | 0.039 | 0.036 | 0.282 | −0.068 | 0.046 | 0.138 |
| MBS | M1AFLP340 | −0.046 | 0.438 | 1032 | 0.915 | 0.314 | 0.528 | 0.578 | 0.362 | −1.118 | 0.736 | 0.129 |
| ADJRTR | M1AFLP340 | −0.185 | 3.915 | 1400 | 0.962 | 0.996 | 0.066 | 5.182 | 0.990 | −0.484 | 6.530 | 0.941 |
| HCWVALUE | M1AFLP340 | 0.003 | 0.224 | 1400 | 0.989 | 0.945 | −0.062 | 0.296 | 0.834 | 0.126 | 0.373 | 0.736 |
| DOF | M1AFLP340 | −0.001 | 0.113 | 1400 | 0.996 | 0.919 | 0.040 | 0.149 | 0.791 | −0.077 | 0.188 | 0.681 |
| ADDCARCVAL | M1AFLP345 | −4.357 | 1.818 | 1399 | 0.017 | 0.037 | −2.656 | 2.581 | 0.304 | −2.899 | 3.122 | 0.353 |
| CHOICEQG | M1AFLP345 | 0.044 | 0.022 | 1390 | 0.050 | 0.094 | 0.022 | 0.032 | 0.478 | 0.036 | 0.038 | 0.348 |
| ADG | M1AFLP345 | −0.037 | 0.021 | 1399 | 0.073 | 0.113 | −0.015 | 0.029 | 0.614 | −0.038 | 0.035 | 0.285 |
| REA | M1AFLP345 | −0.120 | 0.073 | 1399 | 0.101 | 0.146 | −0.041 | 0.103 | 0.694 | −0.135 | 0.125 | 0.282 |
| ADJRTR | M1AFLP345 | −6.657 | 4.091 | 1399 | 0.104 | 0.038 | 1.459 | 5.802 | 0.802 | −13.831 | 7.019 | 0.049 |
| CUTT | M1AFLP345 | −0.112 | 0.073 | 1392 | 0.125 | 0.120 | −0.011 | 0.103 | 0.911 | −0.171 | 0.125 | 0.170 |
| CALCYG | M1AFLP345 | 0.047 | 0.031 | 1392 | 0.130 | 0.116 | 0.003 | 0.044 | 0.948 | 0.076 | 0.054 | 0.156 |
| QUALITY | M1AFLP345 | −0.038 | 0.025 | 1390 | 0.135 | 0.214 | −0.014 | 0.036 | 0.696 | −0.040 | 0.044 | 0.356 |
| BFAT | M1AFLP345 | 0.009 | 0.007 | 1381 | 0.174 | 0.183 | 0.001 | 0.009 | 0.934 | 0.014 | 0.011 | 0.213 |
| PREDYG | M1AFLP345 | 0.022 | 0.016 | 1392 | 0.187 | 0.209 | 0.002 | 0.023 | 0.922 | 0.033 | 0.028 | 0.239 |
| CARCFAT | M1AFLP345 | 0.144 | 0.109 | 1392 | 0.187 | 0.209 | 0.015 | 0.154 | 0.921 | 0.220 | 0.187 | 0.239 |
| FRAME | M1AFLP345 | −0.044 | 0.041 | 1399 | 0.279 | 0.546 | −0.052 | 0.058 | 0.365 | 0.014 | 0.070 | 0.838 |
| YG | M1AFLP345 | 0.028 | 0.029 | 1337 | 0.328 | 0.143 | −0.022 | 0.041 | 0.593 | 0.084 | 0.049 | 0.087 |
| DMI | M1AFLP345 | −17.984 | 18.817 | 1399 | 0.339 | 0.625 | −21.160 | 26.724 | 0.429 | 5.413 | 32.329 | 0.867 |
| REAHCW | M1AFLP345 | −0.009 | 0.010 | 1399 | 0.366 | 0.385 | 0.001 | 0.014 | 0.917 | −0.018 | 0.017 | 0.296 |
| HCW | M1AFLP345 | −2.719 | 3.074 | 1399 | 0.377 | 0.676 | −2.663 | 4.365 | 0.542 | −0.095 | 5.281 | 0.986 |
| INWT | M1AFLP345 | 2.741 | 3.134 | 1399 | 0.382 | 0.546 | 0.629 | 4.450 | 0.888 | 3.599 | 5.384 | 0.504 |
| CHOICEMBS | M1AFLP345 | 0.021 | 0.026 | 1033 | 0.406 | 0.416 | −0.005 | 0.037 | 0.882 | 0.046 | 0.044 | 0.303 |
| DP | M1AFLP345 | −0.066 | 0.092 | 1399 | 0.473 | 0.751 | −0.088 | 0.130 | 0.498 | 0.038 | 0.157 | 0.808 |
| COST | M1AFLP345 | 1.373 | 2.216 | 1399 | 0.536 | 0.784 | 0.659 | 3.148 | 0.834 | 1.218 | 3.808 | 0.749 |
| CALCWT | M1AFLP345 | −2.746 | 4.578 | 1399 | 0.549 | 0.832 | −2.331 | 6.502 | 0.720 | −0.709 | 7.866 | 0.928 |
| HCWVALUE | M1AFLP345 | 0.134 | 0.234 | 1399 | 0.566 | 0.835 | 0.093 | 0.332 | 0.779 | 0.070 | 0.402 | 0.862 |
| ADJNR | M1AFLP345 | −2.005 | 3.834 | 1399 | 0.601 | 0.352 | 3.199 | 5.442 | 0.557 | −8.870 | 6.584 | 0.178 |
| WT3 | M1AFLP345 | −1.318 | 4.589 | 1399 | 0.774 | 0.931 | −0.179 | 6.517 | 0.978 | −1.940 | 7.884 | 0.806 |
| MBS | M1AFLP345 | 0.120 | 0.455 | 1033 | 0.792 | 0.418 | −0.476 | 0.647 | 0.462 | 1.014 | 0.783 | 0.195 |
| BFATRATE | M1AFLP345 | 0.000 | 0.000 | 1381 | 0.827 | 0.837 | 0.000 | 0.000 | 0.812 | 0.000 | 0.000 | 0.579 |
| DOF | M1AFLP345 | 0.018 | 0.118 | 1399 | 0.879 | 0.988 | 0.014 | 0.167 | 0.931 | 0.006 | 0.203 | 0.977 |
| HCWVALUE | UCP2INT2 | −0.542 | 0.219 | 1529 | 0.013 | 0.019 | −0.799 | 0.291 | 0.006 | 0.480 | 0.358 | 0.180 |
| QUALITY | UCP2INT2 | 0.055 | 0.024 | 1519 | 0.021 | 0.048 | 0.037 | 0.032 | 0.247 | 0.034 | 0.039 | 0.391 |
| MBS | UCP2INT2 | −0.880 | 0.433 | 1117 | 0.042 | 0.104 | −1.135 | 0.592 | 0.055 | 0.455 | 0.722 | 0.529 |
| CHOICEQG | UCP2INT2 | −0.035 | 0.021 | 1519 | 0.094 | 0.075 | −0.007 | 0.028 | 0.816 | −0.053 | 0.034 | 0.124 |
| CHOICEMBS | UCP2INT2 | −0.038 | 0.025 | 1117 | 0.124 | 0.182 | −0.015 | 0.034 | 0.667 | −0.042 | 0.041 | 0.308 |
| ADJRTR | UCP2INT2 | −5.548 | 3.820 | 1529 | 0.147 | 0.343 | −6.183 | 5.079 | 0.224 | 1.186 | 6.246 | 0.849 |
| REA | UCP2INT2 | −0.084 | 0.068 | 1529 | 0.214 | 0.182 | −0.166 | 0.090 | 0.067 | 0.151 | 0.111 | 0.173 |
| DMI | UCP2INT2 | −16.805 | 17.577 | 1529 | 0.339 | 0.004 | −65.391 | 23.294 | 0.005 | 90.700 | 28.646 | 0.0016 |
| ADJNR | UCP2INT2 | 3.182 | 3.582 | 1529 | 0.374 | 0.644 | 4.134 | 4.762 | 0.385 | −1.778 | 5.856 | 0.761 |
| REAHCW | UCP2INT2 | −0.008 | 0.009 | 1529 | 0.386 | 0.206 | 0.004 | 0.012 | 0.711 | −0.023 | 0.015 | 0.121 |
| CUTT | UCP2INT2 | −0.055 | 0.067 | 1521 | 0.413 | 0.678 | −0.036 | 0.089 | 0.687 | −0.036 | 0.110 | 0.745 |
| CALCYG | UCP2INT2 | 0.022 | 0.029 | 1521 | 0.441 | 0.729 | 0.017 | 0.038 | 0.650 | 0.009 | 0.047 | 0.847 |
| DOF | UCP2INT2 | −0.063 | 0.110 | 1529 | 0.566 | 0.637 | −0.137 | 0.147 | 0.352 | 0.137 | 0.180 | 0.449 |
| HCW | UCP2INT2 | −1.573 | 2.845 | 1529 | 0.580 | 0.001 | −10.494 | 3.767 | 0.005 | 16.653 | 4.632 | 0.0003 |
| CALCWT | UCP2INT2 | −1.936 | 4.251 | 1529 | 0.649 | 0.001 | −15.577 | 5.627 | 0.006 | 25.464 | 6.920 | 0.0002 |
| WT3 | UCP2INT2 | −1.788 | 4.252 | 1529 | 0.674 | 0.003 | −14.280 | 5.633 | 0.011 | 23.319 | 6.927 | 0.0008 |
| DP | UCP2INT2 | −0.033 | 0.084 | 1529 | 0.691 | 0.819 | −0.070 | 0.112 | 0.534 | 0.068 | 0.138 | 0.623 |
| ADG | UCP2INT2 | −0.005 | 0.019 | 1529 | 0.781 | 0.023 | −0.051 | 0.025 | 0.045 | 0.085 | 0.031 | 0.0064 |
| FRAME | UCP2INT2 | −0.009 | 0.038 | 1529 | 0.818 | 0.059 | −0.087 | 0.050 | 0.083 | 0.147 | 0.062 | 0.0178 |
| BFATRATE | UCP2INT2 | 0.000 | 0.000 | 1510 | 0.826 | 0.975 | 0.000 | 0.000 | 0.847 | 0.000 | 0.000 | 0.967 |
| YG | UCP2INT2 | −0.005 | 0.027 | 1460 | 0.850 | 0.586 | 0.020 | 0.037 | 0.580 | −0.046 | 0.045 | 0.309 |
| INWT | UCP2INT2 | −0.437 | 2.908 | 1529 | 0.881 | 0.033 | −7.057 | 3.858 | 0.068 | 12.358 | 4.744 | 0.0093 |
| CARCFAT | UCP2INT2 | 0.011 | 0.101 | 1521 | 0.916 | 0.985 | 0.023 | 0.134 | 0.865 | −0.023 | 0.165 | 0.890 |
| PREDYG | UCP2INT2 | 0.002 | 0.015 | 1521 | 0.917 | 0.985 | 0.003 | 0.020 | 0.865 | −0.003 | 0.025 | 0.890 |
| COST | UCP2INT2 | 0.188 | 2.046 | 1529 | 0.927 | 0.035 | −4.441 | 2.714 | 0.102 | 8.640 | 3.338 | 0.0097 |
| BFAT | UCP2INT2 | 0.000 | 0.006 | 1510 | 0.974 | 0.988 | 0.001 | 0.008 | 0.939 | −0.002 | 0.010 | 0.877 |
| ADDCARCVAL | UCP2INT2 | 0.021 | 1.707 | 1529 | 0.990 | 0.356 | −2.126 | 2.268 | 0.349 | 4.008 | 2.790 | 0.151 |
| YG | GHREL | 0.107 | 0.035 | 1446 | 0.002 | 0.005 | 0.177 | 0.069 | 0.011 | 0.090 | 0.077 | 0.244 |
| CALCYG | GHREL | 0.092 | 0.038 | 1505 | 0.015 | 0.048 | 0.119 | 0.075 | 0.111 | 0.035 | 0.083 | 0.674 |
| CUTT | GHREL | −0.213 | 0.088 | 1505 | 0.016 | 0.048 | −0.282 | 0.173 | 0.104 | −0.089 | 0.193 | 0.645 |

TABLE 23-continued

Traits, markers, allelic substitutions and effects

| Trait | Marker | Allele Substitution | | | | Fixed Effect | Additive | | | Dominance | | |
| --- | --- | --- | --- | --- | --- | --- | --- | --- | --- | --- | --- | --- |
| Trait | Marker | Estimate | StdErr | DF | P-value | ProbF | Estimate | StdErr | P-value | Estimate | StdErr | P-value |
| PREDYG | GHREL | 0.045 | 0.020 | 1505 | 0.023 | 0.075 | 0.052 | 0.039 | 0.178 | 0.010 | 0.043 | 0.819 |
| CARCFAT | GHREL | 0.298 | 0.132 | 1505 | 0.024 | 0.075 | 0.350 | 0.260 | 0.179 | 0.066 | 0.290 | 0.819 |
| REA | GHREL | −0.187 | 0.089 | 1513 | 0.036 | 0.110 | −0.183 | 0.176 | 0.298 | 0.006 | 0.196 | 0.978 |
| BFAT | GHREL | 0.016 | 0.008 | 1494 | 0.041 | 0.125 | 0.017 | 0.016 | 0.281 | 0.001 | 0.018 | 0.942 |
| CHOICEQG | GHREL | 0.041 | 0.027 | 1503 | 0.134 | 0.261 | 0.073 | 0.055 | 0.185 | 0.041 | 0.061 | 0.504 |
| REAHCW | GHREL | −0.017 | 0.012 | 1513 | 0.161 | 0.344 | −0.025 | 0.023 | 0.289 | −0.011 | 0.026 | 0.685 |
| COST | GHREL | −3.578 | 2.691 | 1513 | 0.184 | 0.222 | 1.528 | 5.317 | 0.774 | 6.597 | 5.924 | 0.266 |
| BFATRATE | GHREL | 0.000 | 0.000 | 1494 | 0.187 | 0.210 | 0.000 | 0.000 | 0.717 | 0.000 | 0.000 | 0.240 |
| DP | GHREL | −0.146 | 0.111 | 1513 | 0.188 | 0.117 | 0.156 | 0.219 | 0.476 | 0.390 | 0.244 | 0.110 |
| FRAME | GHREL | −0.064 | 0.050 | 1513 | 0.201 | 0.438 | −0.052 | 0.098 | 0.594 | 0.015 | 0.110 | 0.894 |
| QUALITY | GHREL | −0.037 | 0.031 | 1503 | 0.232 | 0.474 | −0.051 | 0.063 | 0.415 | −0.018 | 0.070 | 0.799 |
| INWT | GHREL | −4.138 | 3.823 | 1513 | 0.279 | 0.305 | 3.022 | 7.555 | 0.689 | 9.249 | 8.418 | 0.272 |
| ADJNR | GHREL | −4.170 | 4.710 | 1513 | 0.376 | 0.504 | 1.985 | 9.308 | 0.831 | 7.951 | 10.372 | 0.443 |
| HCW | GHREL | −3.091 | 3.734 | 1513 | 0.408 | 0.447 | 3.031 | 7.379 | 0.681 | 7.909 | 8.223 | 0.336 |
| ADG | GHREL | 0.016 | 0.025 | 1513 | 0.517 | 0.680 | −0.009 | 0.050 | 0.855 | −0.033 | 0.055 | 0.553 |
| CHOICEMBS | GHREL | 0.016 | 0.033 | 1106 | 0.630 | 0.778 | 0.047 | 0.068 | 0.491 | 0.039 | 0.075 | 0.603 |
| ADDCARCVAL | GHREL | −1.031 | 2.252 | 1513 | 0.647 | 0.849 | −2.345 | 4.452 | 0.598 | −1.697 | 4.960 | 0.732 |
| ADJRTR | GHREL | 1.830 | 5.032 | 1513 | 0.716 | 0.898 | −0.652 | 9.947 | 0.948 | −3.206 | 11.083 | 0.772 |
| CALCWT | GHREL | −1.916 | 5.580 | 1513 | 0.731 | 0.843 | 2.575 | 11.029 | 0.815 | 5.802 | 12.290 | 0.637 |
| DOF | GHREL | −0.048 | 0.145 | 1513 | 0.738 | 0.816 | 0.086 | 0.286 | 0.765 | 0.173 | 0.318 | 0.587 |
| WT3 | GHREL | −1.752 | 5.582 | 1513 | 0.754 | 0.822 | 3.410 | 11.033 | 0.757 | 6.668 | 12.294 | 0.588 |
| DMI | GHREL | −5.458 | 23.046 | 1513 | 0.813 | 0.969 | −8.763 | 45.554 | 0.847 | −4.270 | 50.760 | 0.933 |
| MBS | GHREL | 0.118 | 0.579 | 1106 | 0.838 | 0.573 | 1.199 | 1.194 | 0.315 | 1.364 | 1.317 | 0.301 |
| HCWVALUE | GHREL | 0.015 | 0.288 | 1513 | 0.959 | 0.851 | 0.293 | 0.569 | 0.607 | 0.359 | 0.634 | 0.571 |
| REA | NPYINT2 | −0.150 | 0.058 | 1504 | 0.009 | 0.017 | −0.164 | 0.059 | 0.005 | 0.095 | 0.081 | 0.238 |
| QUALITY | NPYINT2 | −0.053 | 0.020 | 1494 | 0.009 | 0.011 | −0.059 | 0.021 | 0.004 | 0.043 | 0.028 | 0.127 |
| CHOICEQG | NPYINT2 | 0.043 | 0.018 | 1494 | 0.014 | 0.017 | 0.048 | 0.018 | 0.007 | −0.036 | 0.025 | 0.148 |
| CALCYG | NPYINT2 | 0.054 | 0.024 | 1496 | 0.029 | 0.015 | 0.063 | 0.025 | 0.012 | −0.065 | 0.034 | 0.057 |
| CUTT | NPYINT2 | −0.121 | 0.057 | 1496 | 0.033 | 0.017 | −0.142 | 0.058 | 0.014 | 0.150 | 0.079 | 0.059 |
| MBS | NPYINT2 | 0.726 | 0.364 | 1097 | 0.047 | 0.015 | 0.879 | 0.371 | 0.018 | −1.083 | 0.511 | 0.034 |
| REAHCW | NPYINT2 | −0.015 | 0.008 | 1504 | 0.048 | 0.077 | −0.017 | 0.008 | 0.032 | 0.012 | 0.011 | 0.269 |
| YG | NPYINT2 | 0.037 | 0.023 | 1436 | 0.098 | 0.253 | 0.037 | 0.023 | 0.107 | 0.003 | 0.032 | 0.931 |
| FRAME | NPYINT2 | −0.052 | 0.032 | 1504 | 0.110 | 0.094 | −0.061 | 0.033 | 0.064 | 0.067 | 0.045 | 0.140 |
| CHOICEMBS | NPYINT2 | 0.030 | 0.021 | 1097 | 0.153 | 0.228 | 0.034 | 0.021 | 0.112 | −0.028 | 0.029 | 0.339 |
| ADJNR | NPYINT2 | −4.330 | 3.033 | 1504 | 0.154 | 0.168 | −5.062 | 3.090 | 0.102 | 5.256 | 4.244 | 0.216 |
| ADDCARCVAL | NPYINT2 | −1.866 | 1.447 | 1504 | 0.198 | 0.122 | −2.316 | 1.474 | 0.116 | 3.233 | 2.024 | 0.110 |
| DOF | NPYINT2 | 0.089 | 0.094 | 1504 | 0.345 | 0.418 | 0.072 | 0.096 | 0.454 | 0.122 | 0.132 | 0.355 |
| ADJRTR | NPYINT2 | −2.922 | 3.238 | 1504 | 0.367 | 0.626 | −3.145 | 3.300 | 0.341 | 1.598 | 4.532 | 0.725 |
| CARCFAT | NPYINT2 | 0.077 | 0.085 | 1496 | 0.368 | 0.083 | 0.111 | 0.087 | 0.202 | −0.243 | 0.119 | 0.041 |
| PREDYG | NPYINT2 | 0.011 | 0.013 | 1496 | 0.370 | 0.084 | 0.017 | 0.013 | 0.203 | −0.036 | 0.018 | 0.041 |
| BFAT | NPYINT2 | 0.005 | 0.005 | 1485 | 0.379 | 0.076 | 0.007 | 0.005 | 0.206 | −0.015 | 0.007 | 0.037 |
| WT3 | NPYINT2 | −3.150 | 3.613 | 1504 | 0.383 | 0.485 | −3.735 | 3.681 | 0.311 | 4.198 | 5.056 | 0.407 |
| BFATRATE | NPYINT2 | 0.000 | 0.000 | 1485 | 0.391 | 0.022 | 0.000 | 0.000 | 0.733 | 0.000 | 0.000 | 0.009 |
| HCW | NPYINT2 | −1.973 | 2.422 | 1504 | 0.415 | 0.686 | −2.117 | 2.469 | 0.391 | 1.028 | 3.391 | 0.762 |
| CALCWT | NPYINT2 | −2.317 | 3.614 | 1504 | 0.522 | 0.619 | −2.838 | 3.683 | 0.441 | 3.741 | 5.057 | 0.460 |
| DP | NPYINT2 | −0.042 | 0.072 | 1504 | 0.561 | 0.504 | −0.027 | 0.073 | 0.707 | −0.102 | 0.100 | 0.309 |
| COST | NPYINT2 | −0.941 | 1.740 | 1504 | 0.589 | 0.863 | −0.924 | 1.774 | 0.602 | −0.117 | 2.436 | 0.962 |
| ADG | NPYINT2 | −0.009 | 0.016 | 1504 | 0.597 | 0.613 | −0.011 | 0.016 | 0.497 | 0.019 | 0.023 | 0.403 |
| INWT | NPYINT2 | −1.254 | 2.473 | 1504 | 0.612 | 0.856 | −1.367 | 2.520 | 0.588 | 0.811 | 3.461 | 0.815 |
| HCWVALUE | NPYINT2 | 0.043 | 0.187 | 1504 | 0.819 | 0.393 | 0.092 | 0.190 | 0.630 | −0.352 | 0.261 | 0.178 |
| DMI | NPYINT2 | −1.142 | 14.774 | 1504 | 0.938 | 0.987 | −1.546 | 15.057 | 0.918 | 2.896 | 20.679 | 0.889 |
| QUALITY | SCD | 4162 | 0.040 | 0.013 | 0.003 | 0.009 | −0.031 | 0.018 | 0.087 | 0.015 | 0.023 | 0.506 |
| CHOICEQG | SCD | 4267 | −0.036 | 0.013 | 0.005 | 0.014 | 0.025 | 0.018 | 0.154 | −0.019 | 0.022 | 0.381 |
| BFAT | SCD | 4177 | −0.011 | 0.004 | 0.008 | 0.010 | 0.017 | 0.006 | 0.003 | 0.010 | 0.007 | 0.145 |
| REA | SCD | 4243 | 0.068 | 0.040 | 0.090 | 0.029 | −0.145 | 0.055 | 0.008 | −0.139 | 0.068 | 0.041 |
| YIELD | SCD | 4168 | −0.031 | 0.020 | 0.120 | 0.152 | 0.053 | 0.027 | 0.054 | 0.039 | 0.034 | 0.246 |

Example 8

Figure 9:
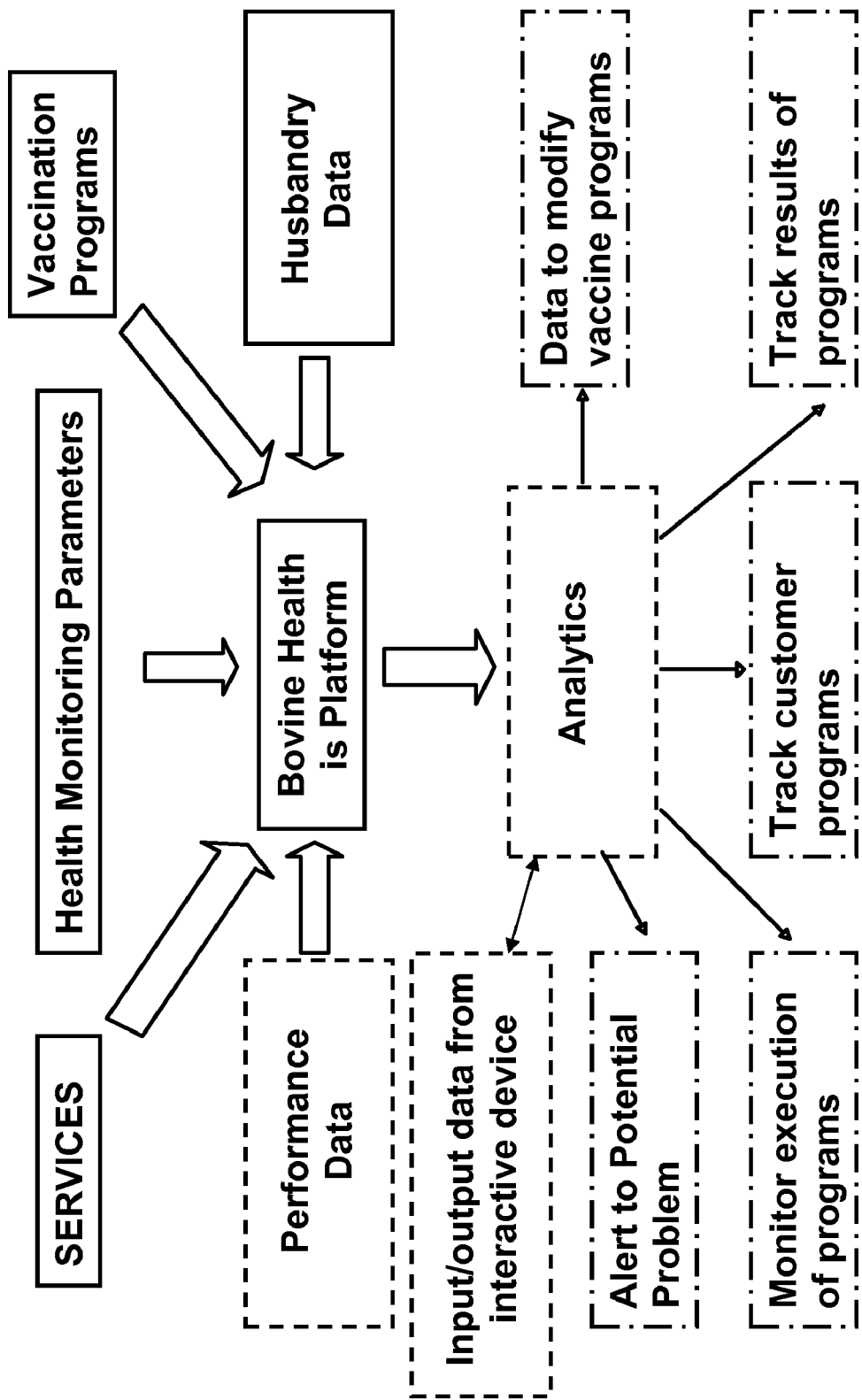
FIG. 9 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 9 shows a flowchart of the input of data and the output of results from the analysis and correlation of the data pertaining to the breeding, veterinarian histories and performance requirements of a group of animals such as from bovines. The flowchart illustrated in FIG. 9 further indicate the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 10:
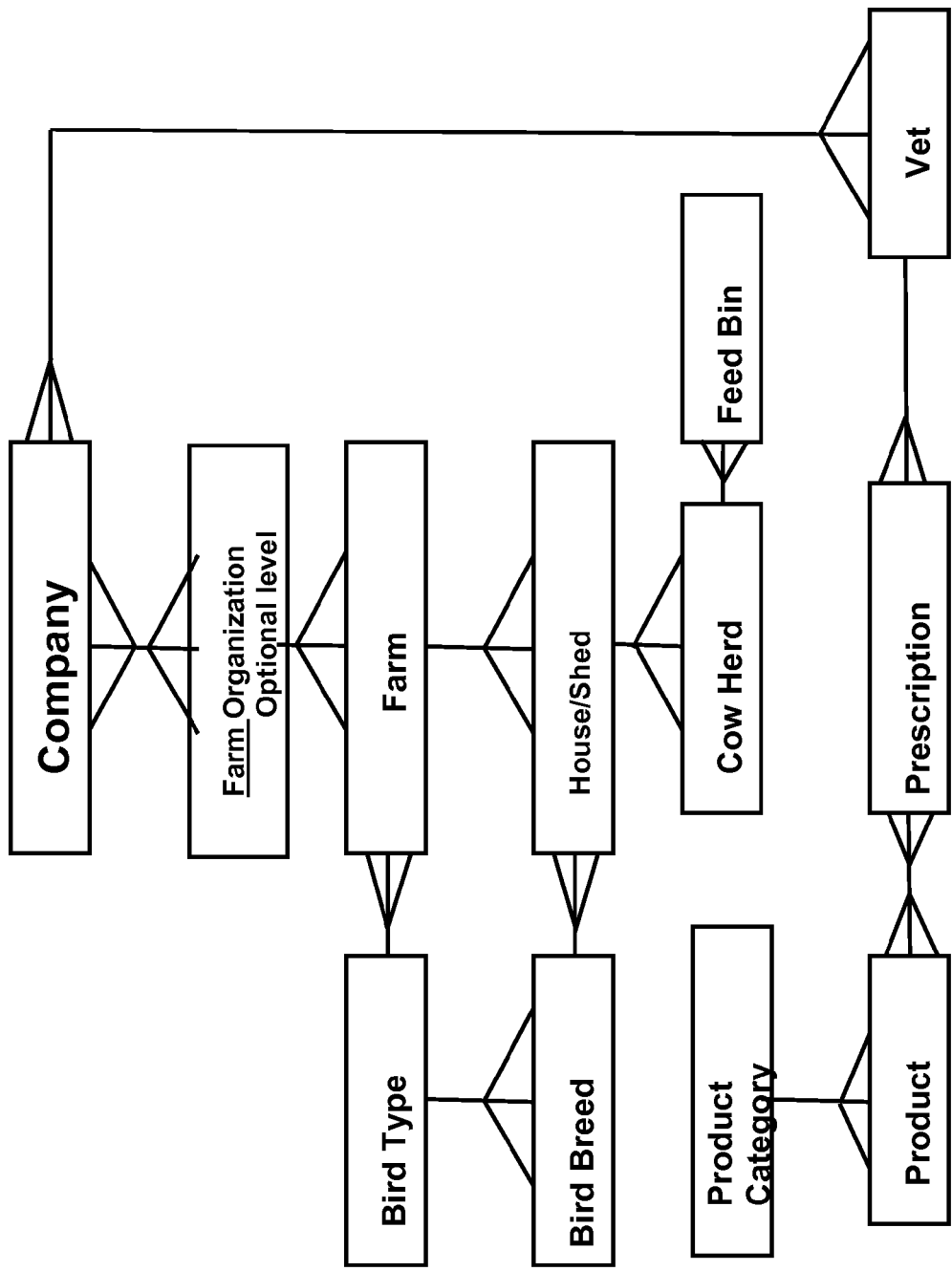
FIG. 10 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

FIG. 10 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 11A:
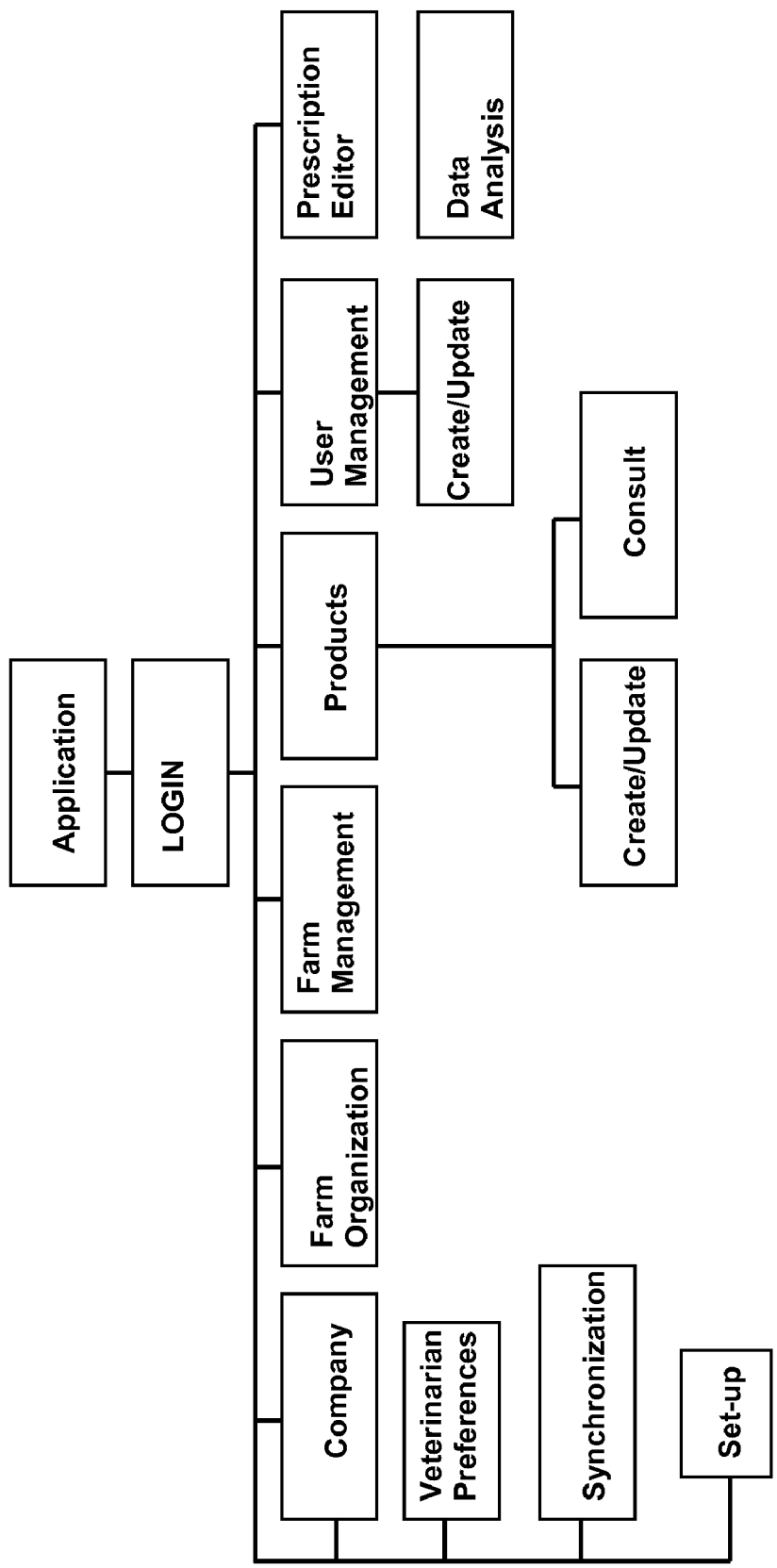
FIG. 11A illustrates the flow of events in the use of the portable computer-based system for data entry on the breeding and rearing of a herd of cows.
Figure 11B:
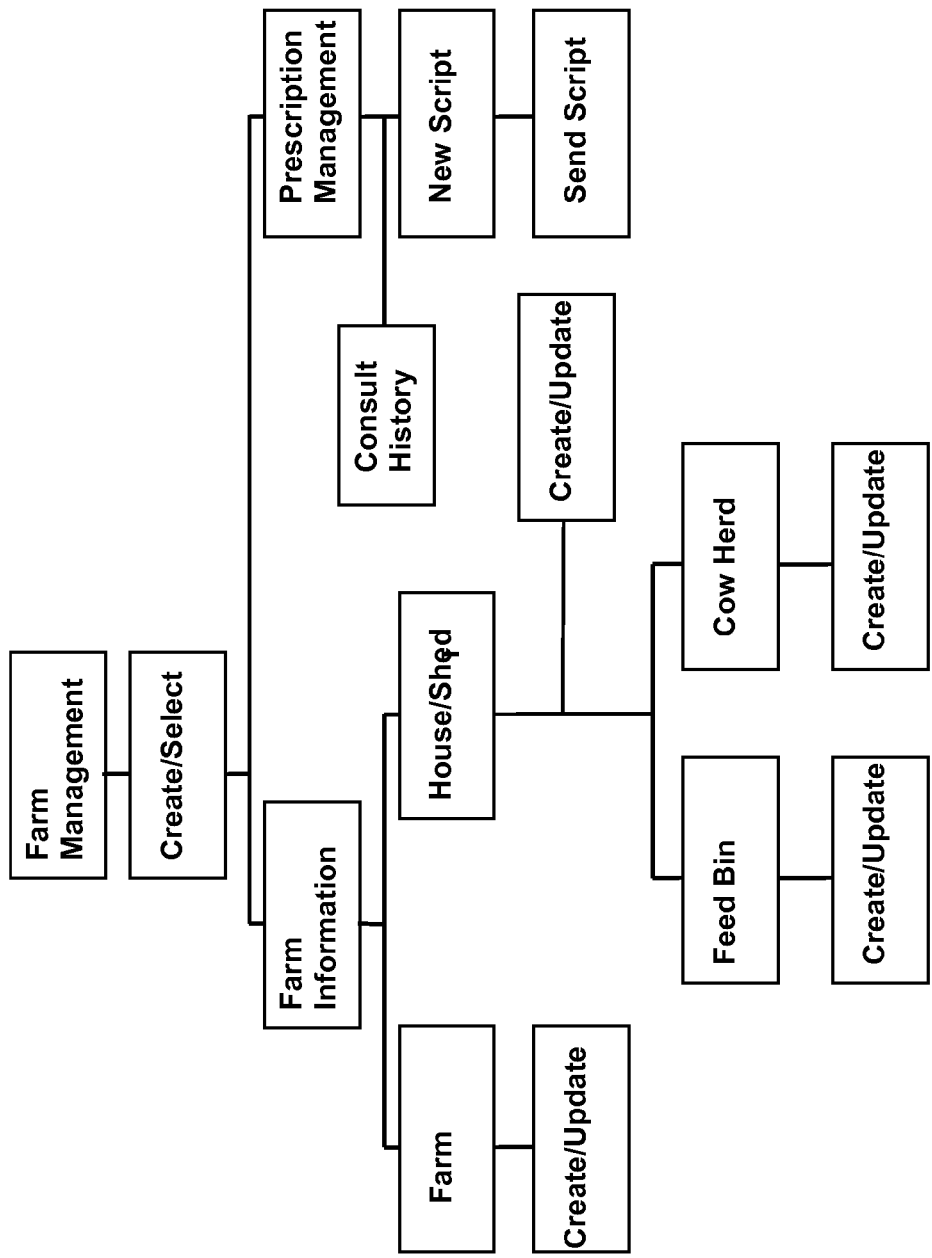
FIG. 11B illustrates the flow of events through the subroutines related to data entry concerning farm management.
Figure 11C:
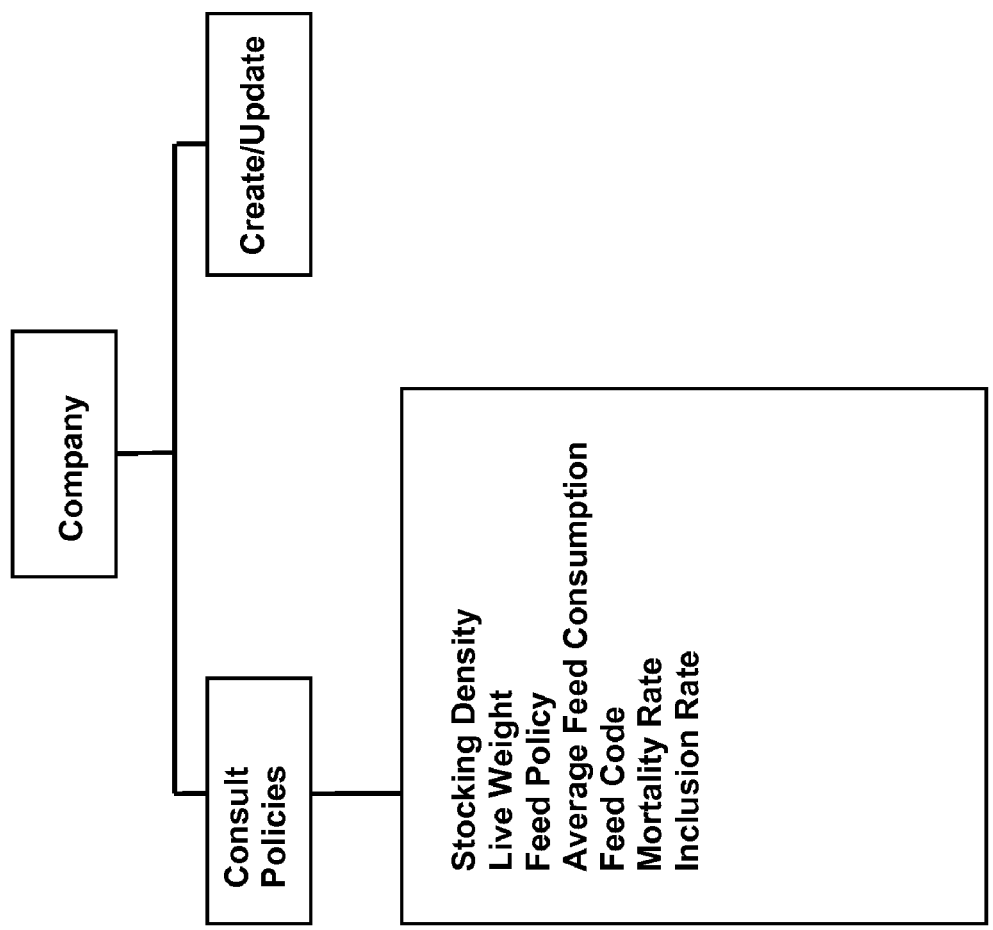
FIG. 11C illustrates the flow of events through the subroutines related to data entry concerning data specific to a company.

FIG. 11A illustrates the flow of events in the use of the portable computer-based system for data entry on the breeding and rearing of a herd of cows. FIG. 11B illustrates the flow of events through the sub-routines related to data entry concerning farm management. FIG. 11 C illustrates the flow of events through the sub-routines related to data entry concerning data specific to a company.

Figure 12:
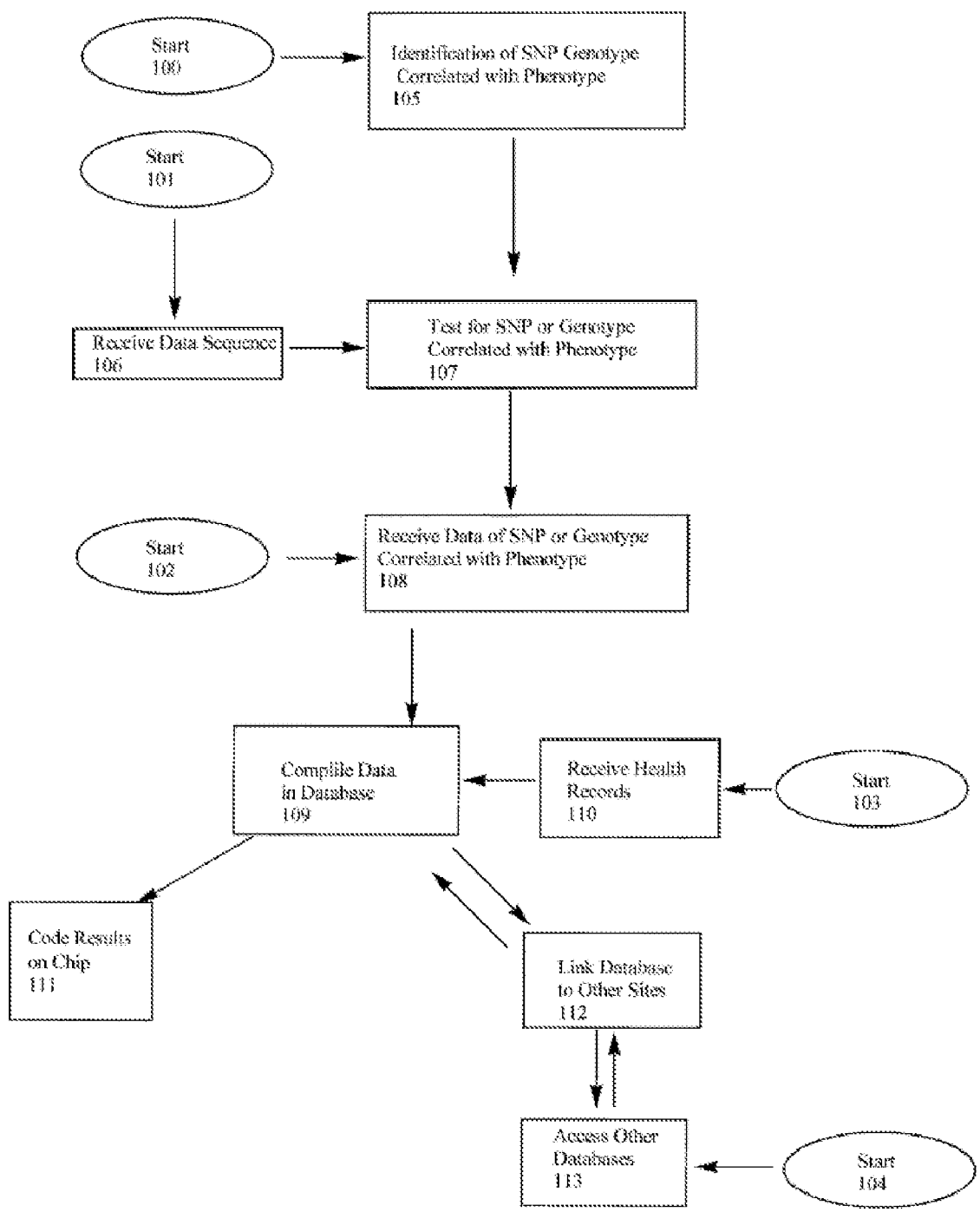
FIG. 12 illustrates a flow chart of the input of data and the output of results from the analysis and the correlation of the data pertaining to the breeding, veterinarian histories, and performance requirements of a group of animals.

FIG. 12 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub grouping animals according to genotype wherein the animals of each sub-group have a similar polymorphism in a GHR, ghrelin, leptin, NPY or UCP2 gene comprising:
   (a) determining the genotype of each animal to be sub-grouped by determining the presence of a single nucleotide polymorphism in the GHR, ghrelin, leptin, NPY or UCP2 gene, and
   (b) segregating individual animals into sub-groups wherein each animal in a subgroup has a similar polymorphism in the GHR, ghrelin, leptin, NPY or UCP2 gene.

2. A method for sub grouping animals according to genotype wherein the animals of each sub-group have a similar genotype in the GHR, ghrelin, leptin, NPY or UCP2 gene comprising:
   (a) determining the genotype of each animal to be sub-grouped by determining the presence of a single nucleotide polymorphism(s) of interest in the GHR, ghrelin, leptin, NPY or UCP2 gene,
   (b) segregating individual animals into sub-groups depending on whether the animals have, or do not have, the single nucleotide polymorphism(s) of interest in the GHR, ghrelin, leptin, NPY or UCP2 gene.

3. The method of paragraphs 1 or 2, wherein the single nucleotide polymorphism(s) of interest is selected from the group consisting of an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene and a C to G substitution at position 213 in intron 2 of the UCP2 gene.

4. A method for sub grouping animals according to genotype wherein the animals of each sub-group have a similar genotype in the GHR, ghrelin, leptin, NPY or UCP2 gene comprising:
   (a) determining the genotype of each animal to be sub-grouped by determining the presence of an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene or a C to G substitution at position 213 in intron 2 of the UCP2 gene, and
   (b) segregating individual animals into sub-groups depending on whether the animals have, or do not have, an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene or a C to G substitution at position 213 in intron 2 of the UCP2 gene single nucleotide polymorphism in the GHR, ghrelin, leptin, NPY or UCP2 gene.

5. A method for identifying an animal having a desirable phenotype relating to certain feed intake, growth rate, body weight, carcass merit and composition, and milk yield, as compared to the general population of animals of that species, comprising determining the presence of a single nucleotide polymorphism in the GHR, ghrelin, leptin, NPY or UCP2 gene of the animal, wherein the polymorphism is selected from the group consisting of an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene or a C to G substitution at position 213 in intron 2 of the UCP2 gene, wherein the presence of either an A to G substitution at the 300 nucleotide position in intron 4 of the GHR gene, an A to G substitution in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene or a C to G substitution at position 213 in intron 2 of the UCP2 gene single nucleotide polymorphism is indicative of a desirable phenotype relating to certain feed intake, growth rate, body weight, carcass merit and composition, and milk yield.

6. The method of any one of paragraphs 1 to 5 wherein the animal is a bovine.

7. The method of any one of paragraphs 1 to 7 wherein the GHR, ghrelin, leptin, NPY or UCP2 gene is a bovine GHR, ghrelin, leptin, NPY or UCP2 gene.

8. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

9. The method according to paragraph 8, wherein the computer system is an interactive system whereby modifications to the output of the computer-assisted method may be correlated according to the input from the interactive device.

10. The method according to paragraph 8, further comprising the steps of inputting into the programmed computer diagnostic data related to the health of the cow or herd of cows; and correlating the diagnostic data to the breeding and veterinary histories of the cow or herd of cows.

11. The method according to paragraph 8, wherein the veterinary data comprises a vaccination record for a cow or herd of cows.

12. The method according to paragraph 10 wherein the health data is selected from the group consisting of husbandry condition data, herd history, and food safety data.

13. The method according to paragraph 8, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

14. The method according to paragraph 8, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

15. The computer-assisted method according to paragraph 8 for optimizing efficiency of feed lots for livestock comprising outputting to the output device the breeding and veterinary history of the bovine or herd of bovines and feeding the animal(s) a diet based upon their breeding and veterinary histories, thereby optimizing efficiency of feed lots for the bovine or herd of bovines.

16. A method of transmitting data comprising transmission of information from such methods according to paragraph 8, selected from the group consisting of telecommunication, telephone, video conference, mass communication, a presentation, a computer presentation, a POWERPOINT™ presentation, internet, email, and documentary communication.

17. An interactive computer system according to paragraph 8 for tracking breeding and welfare histories of poultry comprising breeding and veterinarian data corresponding to a bovine or herd of bovines, and wherein the computer system is configured to allow the operator thereof to exchange data with the device or a remote database.

18. The interactive computer system according to paragraph 17, wherein the input and output devices are a personal digital assistant or a pocket computer.

19. A method of doing business for tracking breeding and welfare histories of livestock comprising breeding and veterinarian data corresponding to one or more livestock animals comprising providing to a user the computer system of paragraph 17.

20. A method of doing business for tracking breeding and welfare histories of livestock comprising breeding and veterinarian data corresponding to one or more livestock animals comprising providing to a user the computer system of paragraph 18.

21. The method of doing business according to paragraph 19, further comprising providing the animal owner or customer with sample collection equipment, such as swabs and vials useful for collecting samples from which genetic data may be obtained, and wherein the vials are optionally packaged in a container which is encoded with identifying indicia.

22. The method of doing business according to paragraph 8, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

23. The method of any one of paragraphs 8 to 22 wherein the data comprises presence or absence of one or more of a single nucleotide polymorphism(s) of interest in the GHR, ghrelin, leptin, NPY or UCP2 gene.

24. The method of paragraph 23 wherein the single nucleotide polymorphism(s) of interest is selected from the group consisting of an A to G substitution at the 300 nucleotide position in intron 4 of the GHR gene, an A to G substitution at position 212 in intron 3 of the ghrelin gene, a C to T mutation at position 528 in the leptin gene, a C to T mutation at position 321 in the leptin gene, an A to G substitution at the 666 nucleotide position in intron 2 of the NPY gene, an A to G substitution at position 812 of exon 4 in the UCP2 gene and a C to G substitution at position 213 in intron 2 of the UCP2 gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a higher average daily gain (ADG), a higher final weight (FW), a higher dry matter intake (DMI), a higher metabolic mid-weight (MMW), a higher slaughter weight (SW), and a higher loin muscle area (LMA), as compared to a general population of bovine animals, comprising the steps of:

(a) obtaining a biological sample from said bovine animal, wherein the sample comprises nucleic acids comprising the bovine growth hormone receptor (GHR) gene;

(b) detecting in said nucleic acids the presence of a single nucleotide polymorphism (SNP) in the GHR gene, wherein the SNP is a G in both alleles of the GHR gene at the position corresponding to position 300 of SEQ ID NO: 1; and (c) correlating the G in both alleles of the GHR gene to higher ADG, FW, DMI, MMW, SW, and LMA, thereby identifying said bovine animal.

2. A method for producing a population of bovine animals having a higher number of offspring with a higher average daily gain (ADG), a higher final weight (FW), a higher dry matter intake (DMI), a higher metabolic mid-weight (MMW), a higher slaughter weight (SW), and a higher loin muscle area (LMA), as compared to a general population of bovine animals, comprising the steps of:

(a) obtaining a biological sample from each bovine animal from a general population of bovine animals, wherein the sample comprises nucleic acids comprising the bovine growth hormone receptor (GHR) gene;

(b) detecting in said nucleic acids the presence of a single nucleotide polymorphism (SNP) in the GHR gene, wherein the SNP is a G in both alleles of the GHR gene at the position corresponding to position 300 of SEQ ID NO: 1;

(c) segregating individual bovine animals into sub-groups depending on whether the animals have, or do not have, a G in either or both alleles of the GHR gene at the position corresponding to position 300 of SEQ ID NO: 1; and (d) continuously breeding only animals that are heterozygous or homozygous for the G in the GHR gene at the position corresponding to position 300 of SEQ ID NO: 1, thereby producing the population of bovine animals.

* * * * *